United States Patent [19]

Patten et al.

[11] Patent Number: 5,416,089
[45] Date of Patent: May 16, 1995

[54] POLYCYCLIC AND HETEROCYCLIC CHROMOPHORES FOR BIS-IMIDE TUMORICIDALS

[75] Inventors: Arthur D. Patten; Gregory Pacofsky, both of Wilmington, Del.; Steven P. Seitz, Swarthmore, Pa.; Emeka A. Akamike, Bear, Del.; Robert J. Cherney, Newark, Del.; Robert F. Kaltenbach, III; Michael J. Orwat, both of Wilmington, Del.

[73] Assignee: The Du Pont Merck Pharmaceutical Company, Wilmington, Del.

[21] Appl. No.: 80,862

[22] Filed: Jun. 24, 1993

[51] Int. Cl.⁶ ............................................. A61K 31/47
[52] U.S. Cl. ................................... 514/284; 514/280; 546/62; 546/70; 546/58; 546/54; 546/47; 549/384; 549/382
[58] Field of Search ............ 546/62, 70; 514/280, 514/284

[56] References Cited

U.S. PATENT DOCUMENTS

| | | | |
|---|---|---|---|
| 4,841,052 | 6/1989 | Harnisch et al. | 546/99 |
| 4,874,863 | 10/1989 | Brana et al. | 546/100 |
| 5,086,059 | 2/1992 | Ardecky et al. | 514/284 |
| 5,206,249 | 4/1993 | Sun | 514/296 |
| 5,206,250 | 4/1993 | Sun | 514/296 |
| 5,290,931 | 3/1994 | Himeno et al. | 546/41 |

FOREIGN PATENT DOCUMENTS

| | | | |
|---|---|---|---|
| 46-37180 | 11/1971 | Japan | 546/64 |
| 46-37181 | 11/1971 | Japan | 546/64 |
| WO9217453 | 10/1992 | WIPO | |

OTHER PUBLICATIONS

El-Nagger et al., Chem. Abstracts 1982, 99, 88558r.
Horiguchi et al., Chem. Abstracts 1972, 76, 87174a.
Horiguchi et al. Chem. Abstracts 1972, 76, 871756.

*Primary Examiner*—Donald G. Daus
*Attorney, Agent, or Firm*—Gerald J. Boudreaux

[57] ABSTRACT

Anticancer compounds of formula I:

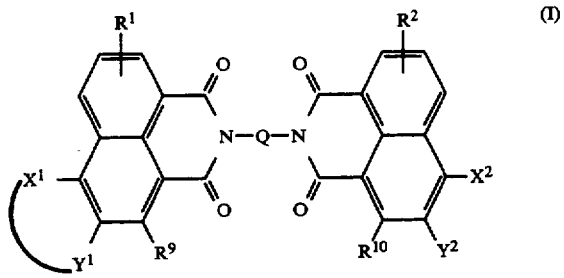

and pharmaceutically acceptable salts thereof, wherein:
$R^1$, $R^2$ and $R^3$ are independently selected H, $CH_3$, $NH_2$, $NO_2$, and CN;
$R^9$ and $R^{10}$ are H or alkyl or halo, $X^1$ and $Y^1$ or $X^2$ and $Y^2$, when present, join together to form, independently, a six membered 1N heterocycle substituted with 1-2 $R^3$; or the group:

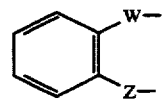

wherein one of W or Z is C=O and the other is C=O, NH, S or O;
or when $X^2$ and $Y^2$ are not joined together and when $R^2$ is in the 4-position, then $X^2$ and $R^2$ may join together to form an ethylene bridge; are disclosed.

15 Claims, No Drawings

POLYCYCLIC AND HETEROCYCLIC CHROMOPHORES FOR BIS-IMIDE TUMORICIDALS

FIELD OF THE INVENTION

This invention relates to bis-imide derivatives of tri- and tetraamines of formula I:

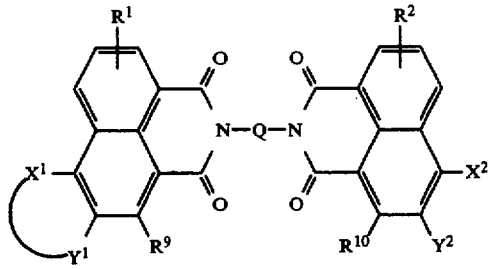

pharmaceutical compositions containing them, and methods of using them to treat cancer, particularly solid tumors, in mammals.

BACKGROUND OF THE INVENTION

R. J. Ardecky, A. D. Patten, and J-H Sun, U.S. Pat. No. 5,086,059, issued Feb. 4, 1992, disclose anticancer agents of formula:

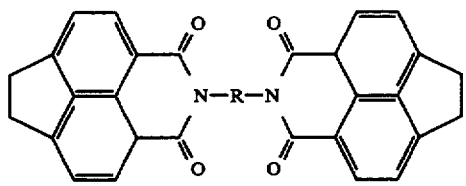

Harnisch et al, U.S. Pat. No. 4,841,052, issued Jun. 20, 1989, disclose fluorescent quenchers of formula:

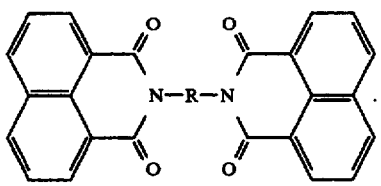

El-Nagger et al., Chem Abstr. 1983, 99, 88558r, disclose compounds of formula:

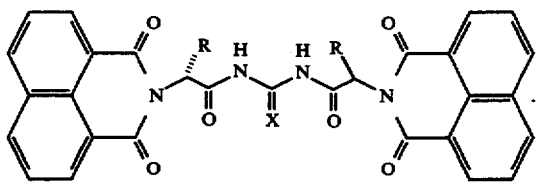

Brana et al., U.S. Pat. No. 4,874,863, issued Oct. 17, 1989, disclose anticancer agents of formula:

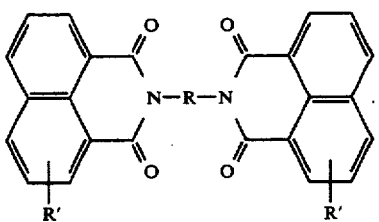

Horiguchi et al., Chem Abstr. 1972, 76, 87174a, disclose fluorescent whitening agents of formula:

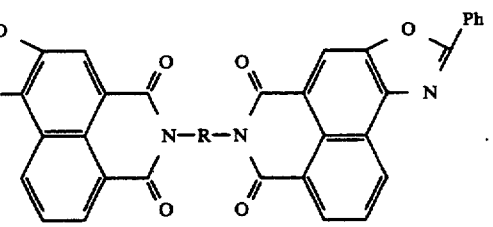

DETAILED DESCRIPTION OF THE INVENTION

There is provided by this invention bis-imides of formula (I):

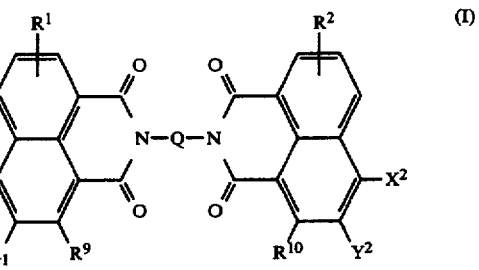

and pharmaceutically acceptable salts thereof, wherein: $R^1$, $R^2$, $R^3$, $R^9$ and $R^{10}$ are independently selected at each occurrence from the group:
  H, $C_1$-$C_4$ alkyl, $OR^4$, $S(O)_q R^4$, N $(R^4)_2$, $NO_2$, CN, F, Cl, Br, I, Ph, $CF_3$, and $NHC(O)R^4$;
$R^4$ is independently selected at each occurrence from the group:
  H, $C_1$-$C_4$ alkyl, Ph, and $CH_2$Ph;
$X^1$ and $Y^1$ join together to form:
  a benzene ring substituted with 1-4 $R^3$;
  a five membered heterocycle containing 1-2 N, NH, O or S atoms and substituted with 1-2 $R^3$;
  a six membered heterocycle containing 1-2 N and substituted with 1-2 $R^3$; or the group:

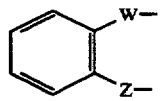

wherein one of W or Z is C=O and the other is C=O, NH, S or O;
$X^2$ and $Y^2$ are optionally present and when present may join together to form:
  a benzene ring substituted with 1-4 $R^3$;

a five membered heterocycle containing 1-2 N, NH, O or S atoms and substituted with 1-2 $R^3$;

a six membered heterocycle containing 1-2 N and substituted with 1-2 $R^3$; or the group:

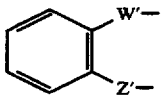

wherein one of W' or Z' is C=O and the other is C=O, NH, S or O; or when $X^2$ and $Y^2$ are not joined together and when $R^2$ is in the 4-position, then $X^2$ and $R^2$ may join together to form an ethylene bridge;

Q is:

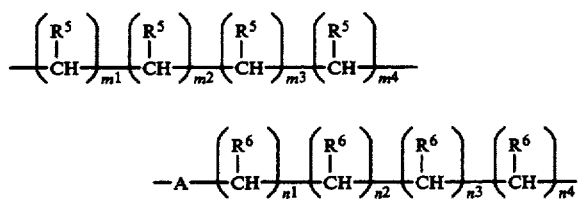

wherein A is $NR^8$ or

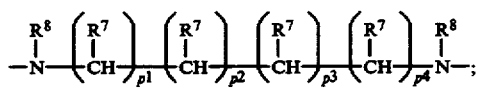

$R^5$, $R^6$, and $R^7$ are independently selected at each occurrence from the group:

H, $C_1$-$C_3$ alkyl, allyl, or $CH_2G$, wherein G is OH, $OCH_3$, $CH_2SCH_3$, $(CH_2)_qNH_2$ and phenyl;

$R^8$ is independently selected at each occurrence from the group:

H, $C_1$-$C_3$ alkyl and allyl;

$m^1$, $m^2$, $m^3$, and $m^4$ are independently 0-1, provided that at least two of $m^1$, $m^2$, $m^3$, and $m^4$ are 1;

$n^1$, $n^2$, $n^3$, and $n^4$ are independently 0-1, provided that at least two of $n^1$, $n^2$, $n^3$, and $n^4$ are 1;

$p^1$, $p^2$, $p^3$, and $p^4$ are independently 0-1, provided that at least two of $p^1$, $p^2$, $p^3$, and $p^4$ are 1; and q is independently at each occurrence 0-2.

Preferred compounds of this invention are those compounds of formula (I) wherein:

$R^1$, $R^2$ and $R^3$ are independently selected at each occurrence from the group:

H, $CH_3$, $NH_2$, $NO_2$, and CN;

$R^9$ and $R^{10}$ are H;

$X^1$ and $Y^1$ join together to form:

a six membered heterocycle containing 1 N and substituted with 1-2 $R^3$; or the group:

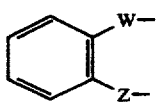

wherein one of W or Z is C=O and the other is C=O, NH, S or O;

$X^2$ and $Y^2$ are optionally present and when present may join together to form:

a six membered heterocycle containing 1 N and substituted with 1-2 $R^3$; or the group:

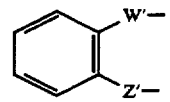

wherein one of W' or Z' is C=O and the other is C=O, NH, S or O; or when $X^2$ and $Y^2$ are not joined together and when $R^2$ is in the 4-position, then $X^2$ and $R^2$ may join together to form an ethylene bridge;

More preferred compounds of this invention are those preferred compounds wherein:

$R^1$ and $R^2$ are independently selected at each occurrence from the group:

H, $NH_2$ and $NO_2$;

$X^1$ and $Y^1$ join together to form:

a six membered heterocycle containing 1 N and substituted with 1-2 $R^3$;

$X^2$ and $Y^2$ are optionally present and when present join together to form:

a six membered heterocycle containing 1 N and substituted with 1-2 $R^3$; or when $X^2$ and $Y^2$ are not joined together and when $R^2$ is in the 4-position, then $X^2$ and $R^2$ may join together to form an ethylene bridge.

$R^5$ and $R^6$ are independently selected at each occurrence from the group:

H, $CH_3$, $CH_2CH_3$ and $CH_2CH_2SCH_3$;

$R^8$ is independently selected at each occurrence from the group:

H and $CH_3$; and the sum of the values of $m^1$, $m^2$, $m^3$, $m^4$, $n^1$, $n^2$, $n^3$, and $n^4$ is 4-7.

Most preferred compounds of this invention are those more preferred compounds wherein:

$R^3$ is independently selected from the group:

H and $CH_3$;

$R^7$ is independently selected from the group:

H, $CH_3$, $CH_2CH_3$ and $CH_2CH_2SCH_3$; and

Q is selected from the group:

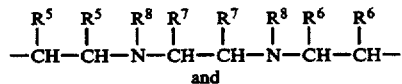

and

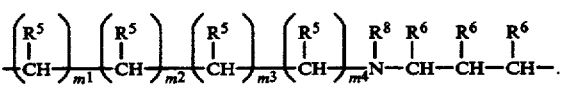

Specifically preferred compounds of this invention are those compounds of formula (I) which are:

(R,R)-1,2-bis-[2-(3-Nitro-5-azaphenanthrene-1,10-dicarboximido)propylamino]ethane Dihydromethanesulfonate;

(R,R)-1,2-bis-[2-(3-Nitro-7-methyl-5-azaphenanthrene-1,10-dicarboximido)propylamino]ethane Dihydromethanesulfonate;

(S,S)-1,2-bis-[2-(3-Nitro-5-azaphenanthrene-1,10-dicarboximido)-1-methylethylamino]ethane Dihydromethanesulfonate;

(R,R)-1,2-bis-[2-(3-Nitro-7-methyl-5-azaphenanthrene-1,10-dicarboximido)propylamino]-(R)-1-methylethane Dihydromethanesulfonate;

4-[3-(3-Nitro-5-azaphenanthrene-1,10-dicarbox-
imido)propylamino]-1-(3-nitronaphthalene-1,8-
dicarboximido)butane Hydromethanesulfonate;

(R,R)-1-[2-(5-Azaphenanthrene-1,10-dicarboximido)-
propylamino]-2-[2-(3-nitronaphthalene-1,8-dicar-
boximido)propylamino]ethane Dihydromethane-
sulfonate;

4-[3-(8-Azaphenanthrene-1,10-dicarboximido)-
propylamino]-1-(3 -nitronaphthalene-1,8-dicarbox-
imido)butane Hydromethanesulfonate;

(R,R)-1-[2-(3-Nitro-7-methyl-5-azaphenanthrene-
1,10-dicarboximido)propylamino]-2-[2-(3-nitro
naphthalene-1,8-dicarboximido)propylamino]e-
thane Dihydromethanesulfonate;

(R,R)-1-[2-(6-Azaphenanthrene-1,10-dicarboximido)-
propylamino]-2-[2-(3-nitronaphthalene-1,8-dicar-
boximido)propylamino]ethane Dihydromethane-
sulfonate;

(R,R)-1-[3-Nitro-6-azaphenanthrene-1,10-dicarbox-
imido)propylamino]-2-[2-(3-nitronaphthalene-1,8-
dicarboximido)propylamino]ethane Dihydrome-
thanesulfonate.

It should be recognized that the above-identified groups of compounds are preferred embodiments of this invention, but that their description herein is in no way intended to limit the overall scope of this invention.

This invention also provides pharmaceutical compositions consisting of suitable pharmaceutical carrier and an amount of one or more of the above-described compounds as needed to effectively treat cancer. Still further, this invention provides a method of treating cancer in a mammal comprised of administering to the mammal a therapeutically effective amount of one or more of the above-described compounds.

The compounds herein described may have asymmetric centers. All chiral, enantiomeric, diastereomeric, and racemic forms are included in the present invention. Thus, the compounds of Formula (I) may be provided in the form of an individual stereoisomer, a non-racemic stereoisomer mixture, a racemic mixture, or a disastereomeric mixture.

When any variable occurs more than one time in any constituent or in formula (I), or any other formula herein, its definition on each occurrence is independent of its definition at every other occurrence. Also, combinations of substituents and/or variables are permissible only if such combinations result in stable compounds.

As used herein, the term "symmetrical" when used in reference to a compound of formula (I) means that the compound has equivalent substituent pairs: $R^1$, $R^2$; $X^1$ and $Y^1$, $X^2$ and $Y^2$; and $R^9$, $R^{10}$. That is, compounds of formula (I) wherein $R^1=R^2$, $X^1$ and $Y^1=X^2$ and $Y^2$, and $R^9=R^{10}$ are "symmetrical" compounds of formula (I). As used herein, the term "unsymmetrical" when used in reference to a compound of formula (I) means that at least one of the substituent pairs, $R^1$, $R^2$; $X^1$ and $Y^1$, $X^2$ and $Y^2$; and $R^9$, $R^{10}$, does not contain equivalent groups. Thus, for example, a compound of formula (I) wherein $R^1=R^2$, $X^1$ and $Y^1=X^2$ and $Y^2$, and $R^9$ does not $=R^{10}$ is an "unsymmetrical" compound of formula (I); similarly, a compound of formula (I) wherein $R^1$ does not $=R^2$, $X^1$ and $Y^1$ do not $=X^2$ and $Y^2$, and $R^9=R^{10}$ is an "unsymmetrical" compound of formula (I); etc.

As used herein, "alkyl" is intended to include both branched and straight-chain saturated aliphatic hydrocarbon groups having the specified number of carbon atoms.

The term "substituted", as used herein, means that one or more hydrogen atom(s) on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, the terms "pharmaceutically acceptable salts" and "pharmaceutically suitable salts" refer to derivatives of the disclosed compounds that are modified by making acid or base salts. Examples include, but are not limited to, mineral or organic acid salts of basic residues such as amines; alkali or organic salts of acidic residues such as carboxylic acids. Pharmaceutically acceptable salts of the compounds of the invention can be prepared by reacting the free acid or base forms of these compounds with an appropriate amount of the desired base or acid in water or in an organic solvent, or in a mixture of the two; generally, nonaqueous media like diethyl ether, ethyl acetate, ethanol, isopropanol, tetrahydrofuran, methylene chloride or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

As used herein, the term "therapeutically effective amount" means that amount of a drug or pharmaceutical agent that will elicit the biological or medical response of a tissue, system, animal or human subject that is being sought by a clinician or researcher.

As used herein the term "cancer" refers to leukemia and solid tumors in man, and, in particular, tumors of the breast and colon.

SYNTHESIS

The compounds of the present invention may be prepared according to the following schemes and examples, using appropriate materials and are further exemplified by the specific examples which follow. Those skilled in the art will readily understand that known variations of the conditions and processes of the following preparative procedures can be used to prepare those compounds. Compounds of the present invention can also be prepared using methods known in the art of organic synthesis. The references cited below are all incorporated herein by reference.

Symmetrical compounds of formula (I) can be prepared by condensing a polycyclic aromatic anhydride of formula 2 with a polyamine of formula 3 in a suitable solvent, such as ethanol, propanol, tetrahydrofuran, dioxane, or dimethylformamide, at temperatures ranging from ambient to the solvent's boiling point. The free base of the bis-imide derivative can be isolated from this reaction mixture or the mixture can be acidified with an appropriate mineral or organic acid to produce a pharmaceutically acceptable salt. The materials are generally obtained by filtration of the reaction mixture. The salts can also be prepared by acidifying a suspension or solution of the isolated free base in ethanol or dichloromethane with the appropriate acid and collecting the thus formed solid by filtration. In some cases, the free base requires purification by column chromatography before its salt can be prepared.

The polyamines are commercially available or can be prepared according to Bergeron, R. J. *Accs. Chem. Res.* 1986, 19, 105, or as described in PCT Application No. PCT/US92/02134 (WO 92/17453).

Scheme 1
Synthesis of Symmetrical Compounds of Formula (I)

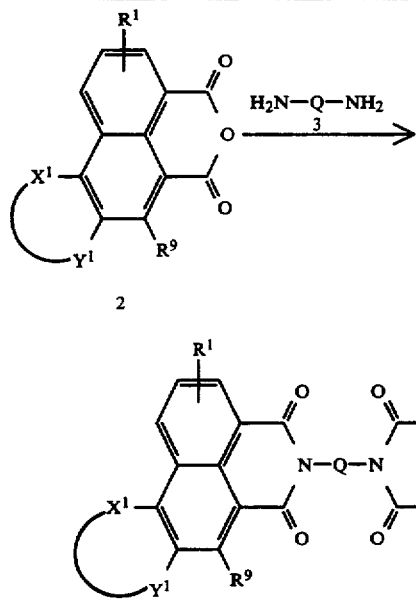

Unsymmetrical compounds of formula (I) can be prepared by reacting a polyamine, 3, with equimolar amounts of two different anhydrides, 2 and 5, and separating the statistical mixture of products by column chromatography as shown in Scheme 2.

Scheme 2
Synthesis of Unsymmetrical Compounds of Formula (I)

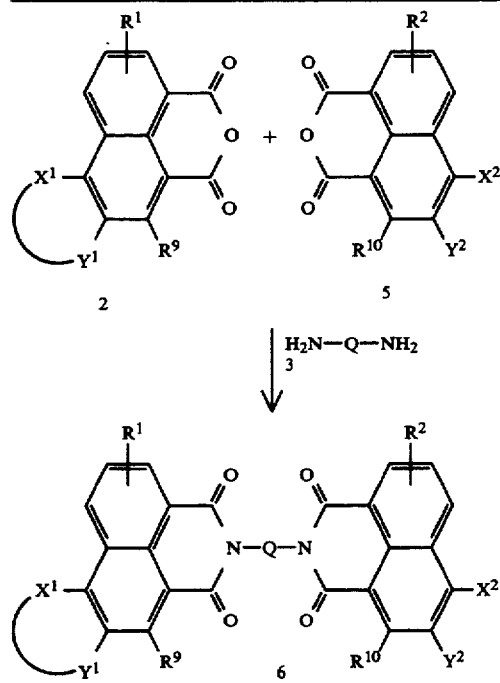

Unsymmetrical compounds of formula (I) can also be prepared by reacting a suitable mono-imide, prepared as described herein, or as described in U.S. patent application Ser. No. 08/016,555, with one equivalent of an anhydride. For example, Scheme 3 shows the synthesis of an unsymmetrical compound of formula (I) from reaction of polycyclic anhydride, 2, with mono-imide, 8, to afford 6 which is an unsymmetrical compound of formula (I). Of course, 6 can also be prepared from reaction of the corresponding mono-imide of 2 with 5 in an analogous fashion.

Scheme 3
Synthesis of Unsymmetrical Compounds of Formula (I)

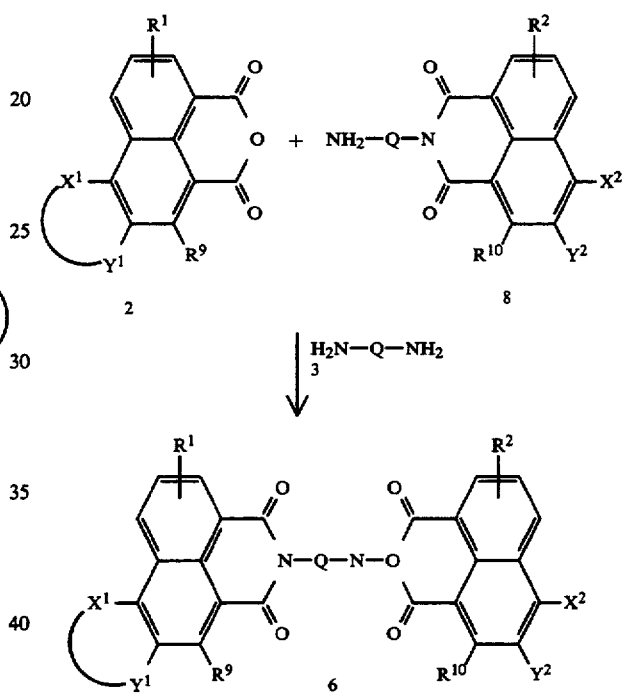

The polycyclic anhydrides utilized for the preparation of the compounds provided by this invention can themselves be prepared by a number of routes, some of which are exemplified here. For example, derivatives of the 5- and 8-azaphenanthrenedicarboxylic anhydrides can be prepared from 5-aminoacenaphthene, 10, 4-aminonaphthalic anhydride, 13, and 3-aminonaphthalic anhydride, 14, as shown in Scheme 4, by a variety of ring forming reactions (Jones, G. in Chemistry of Heterocyclic Compounds, Volume 32, 1977, Weissberger, A.; Taylor, E. C. Editors.; Jones, G. in Comprehensive Heterocyclic Chemistry, Volume 2, 1984, 395, Katritzky, A. R.; Rees, C. W. Editors). The 5 -azaacephenanthrene derivatives, 11, can be oxidized with sodium dichromate to the desired anhydride derivatives, 12. The 5-, 6-, 7-, and 8-azaphenanthrenedicarboxylic anhydrides can be nitrated selectively to give the 3-nitro derivatives, as shown for the 5-aza derivative. These methods are depicted in Scheme 4.

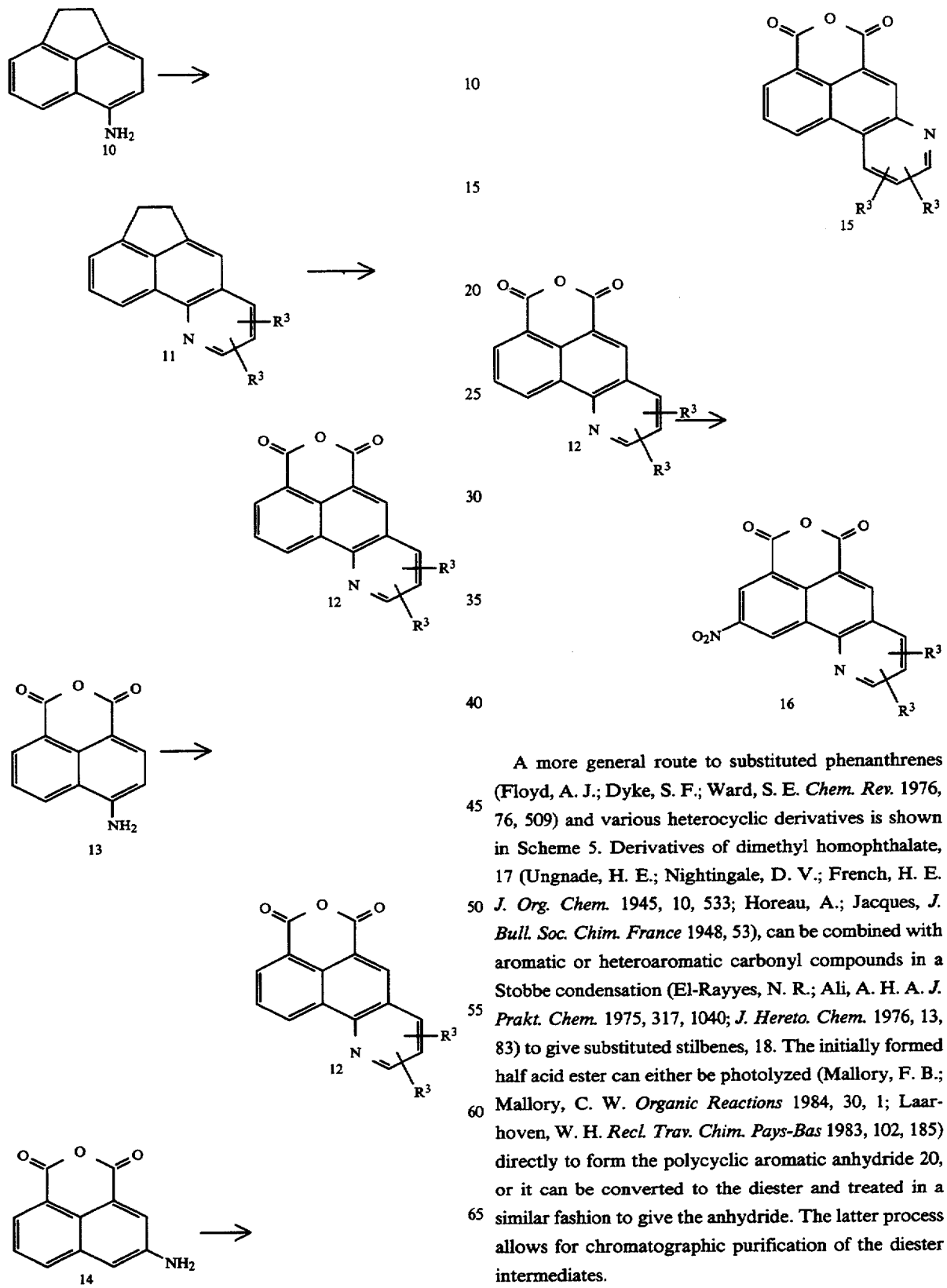

A more general route to substituted phenanthrenes (Floyd, A. J.; Dyke, S. F.; Ward, S. E. *Chem. Rev.* 1976, 76, 509) and various heterocyclic derivatives is shown in Scheme 5. Derivatives of dimethyl homophthalate, 17 (Ungnade, H. E.; Nightingale, D. V.; French, H. E. *J. Org. Chem.* 1945, 10, 533; Horeau, A.; Jacques, J. *Bull. Soc. Chim. France* 1948, 53), can be combined with aromatic or heteroaromatic carbonyl compounds in a Stobbe condensation (El-Rayyes, N. R.; Ali, A. H. A. *J. Prakt. Chem.* 1975, 317, 1040; *J. Hereto. Chem.* 1976, 13, 83) to give substituted stilbenes, 18. The initially formed half acid ester can either be photolyzed (Mallory, F. B.; Mallory, C. W. *Organic Reactions* 1984, 30, 1; Laarhoven, W. H. *Recl. Trav. Chim. Pays-Bas* 1983, 102, 185) directly to form the polycyclic aromatic anhydride 20, or it can be converted to the diester and treated in a similar fashion to give the anhydride. The latter process allows for chromatographic purification of the diester intermediates.

Scheme 5
Photocyclization Route to Polycyclic Anhydrides.

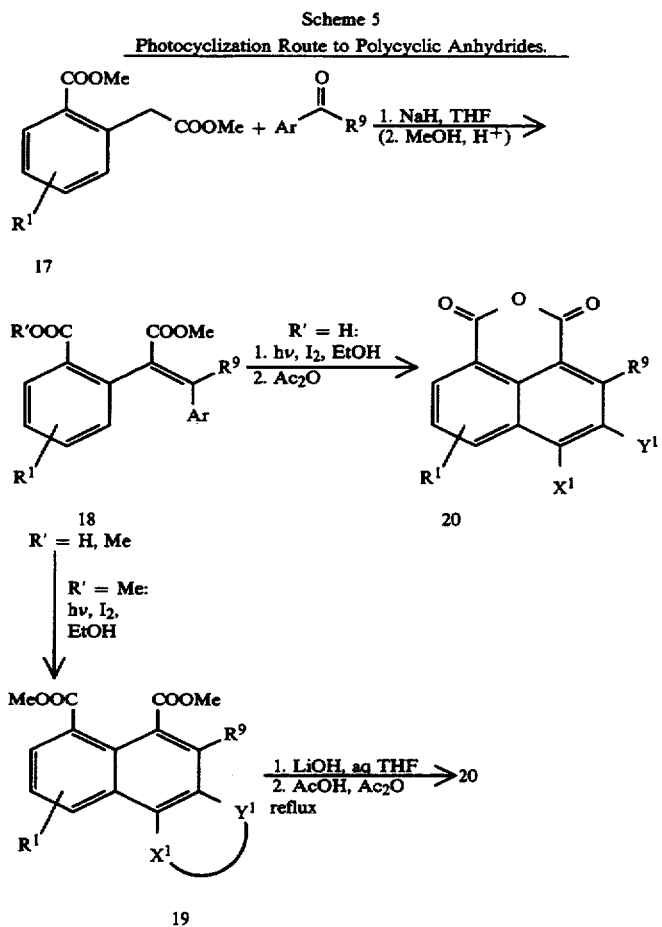

A similar route to polycyclic anhydrides involves the use of ortho-bromo aromatic or heteroaromatic aldehydes, 21, in Stobbe condensations with dimethyl homophthalate derivatives, 17. The stilbene diesters, 22, formed in this process can be converted to the polycyclic systems, 23, using a palladium catalyzed coupling reaction (Ames, D. E.; Opalko, A. *Tetrahedron* 1984, 40, 1919), as shown in Scheme 6. These diesters can be converted as above to the anhydrides 24. This route is advantageous when the condensation components contain functionality that is not compatible with the photocyclization reaction, specifically, nitro groups.

Scheme 6
Palladium Cyclization Route to Polycyclic Anhydrides

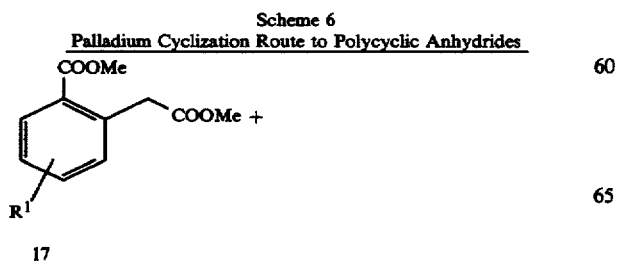

-continued
Scheme 6
Palladium Cyclization Route to Polycyclic Anhydrides

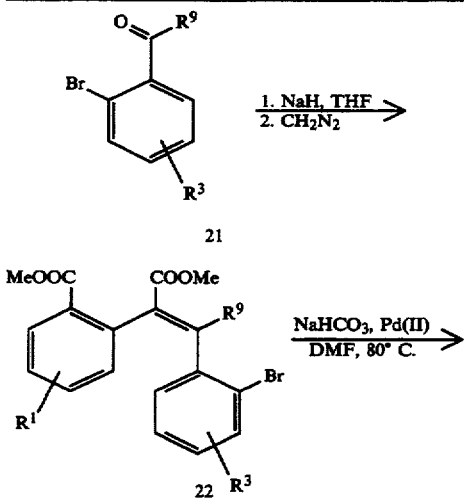

Scheme 6
Palladium Cyclization Route to Polycyclic Anhydrides

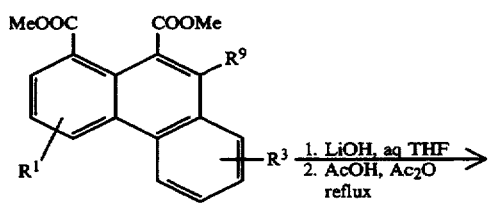

23

1. LiOH, aq THF
2. AcOH, Ac$_2$O reflux
→

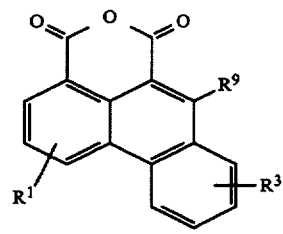

24

Scheme 7
Synthesis of 8-Substituted Phenanthrene Anhydrides.

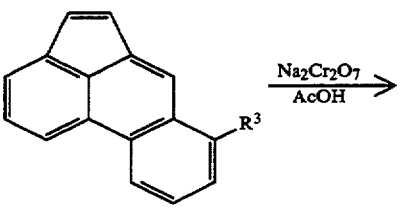

27

$\xrightarrow{\text{Na}_2\text{Cr}_2\text{O}_7}{\text{AcOH}}$

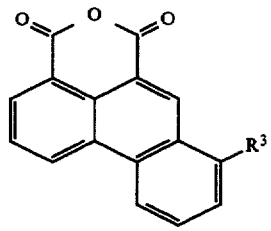

28

8-Substituted phenanthrene compounds can also be made from the known ketone 25 (Scott, L. T.; Reinhardt, G.; Roelofs, N.H. *J. Org. Chem.* 1985, 50, 5886), as shown in Scheme 7. The ketone can be converted to the olefin derivative 26 either by addition of a nucleophile to the ketone and eliminating the alcohol formed or by making an enol derivative of the ketone. This material can be made fully aromatic by treatment with 2,3-dichloro-5,6-dicyano-1,4-benzoquinone (DDQ) and converted to the anhydride 28 by oxidation with sodium dichromate.

Along with the photocyclization method, fused 5-membered ring heterocyclic anhydrides can be prepared as shown in Scheme 8. Fused imidazole anhydrides, 30, can be prepared by reduction of 3-nitro-4-acylaminonaphthalic anhydrides, 29, with stannous chloride and cyclization of the intermediate amino amides (Sachs, F.; Mosebach, G. *Chem. Bet.* 1911, 44, 2852). Fused thiazole compounds, 32, can be prepared by bromination of 3-acylaminonaphthalic anhydrides, 31, and treatment of the resulting 4-bromo derivatives with Lawesson's Reagent (Mylari, B. L.; et al. *J. Med. Chem.* 1991, 34, 108).

Scheme 7
Synthesis of 8-Substituted Phenanthrene Anhydrides.

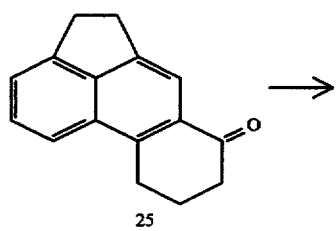

25

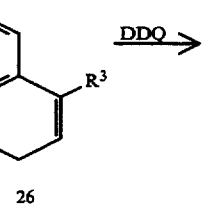

26

$\xrightarrow{\text{DDQ}}$

Scheme 8
Synthesis of 5-Membered Ring Heterocyclic Anhydrides.

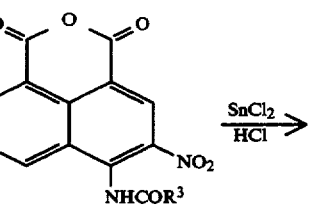

29

$\xrightarrow[\text{HCl}]{\text{SnCl}_2}$

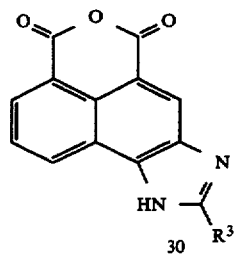

30

Scheme 8
Synthesis of 5-Membered Ring Heterocyclic Anhydrides.

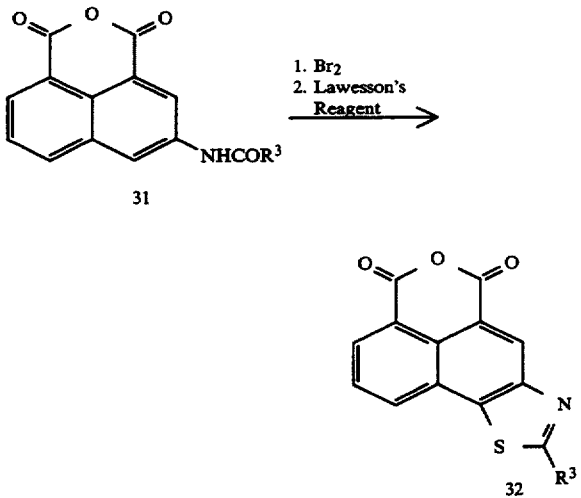

The pentacyclic anhydrides shown in Scheme 9 can be prepared by literature routes (33: Kasai, T.; Ando, H.; Tsuruoka, S. *Kogyo Kagaku Zasshi* 1968, 71, 1871, *Chem. Abstr.* 1969, 70, 77657x; Akiyoshi, S.; Tsuge, O. *Kogyo Kagaku Zasshi* 1956, 59, 455, *Chem. Abstr.* 1958, 52, 3754b; Peters, A. T.; Rowe, F. M. *J. Soc. Dyers Colour.* 1943, 59, 52. 34, 35: Nishi, H.; Ehashi, S. *Kogyo Kagaku Zasshi* 1970, 73, 2425, *Chem. Abstr.* 1971, 75, 5761). The thia derivatives can be prepared using methodology similar to that employed for the aza compounds, 34 and 35.

Scheme 9
Pentacyclic Anhydrides.

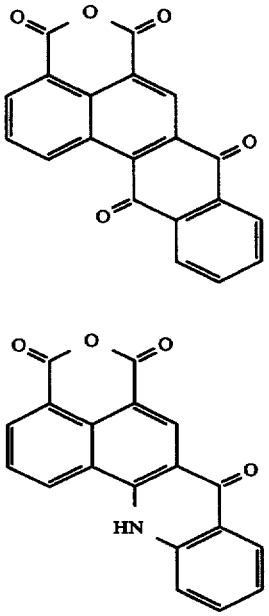

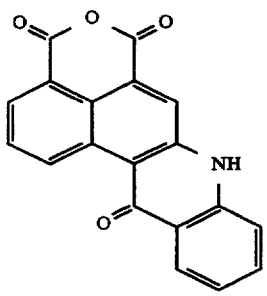

EXAMPLES

The invention can be further understood by referring to the following examples. However, the following examples and preparations are for illustrative purposes only and are not to be construed as limiting the invention.

General Experimental:

NMR spectra were recorded on a Varian VXR-300S spectrometer at a digital resolution of ±0.4 Hz. Infrared spectra were recorded on a Perkin-Elmer Model 1600 FT-IR spectrometer. Low resolution mass spectra (MS) were recorded on a Hewlet Packard 5988A with a particle beam LC/MS interface or a Finnegan MAT 8230 mass spectrometer. High resolution mass spectra (HRMS) were recorded on a VG 70-VSE mass spectrometer. Melting points are uncorrected. Percentage yields are by weight, equivalents refer to molar ratios, and percentages of solvent mixtures are by volume.

General Procedure for the Preparation of bis-Imides and their Salts:

A mixture of the anhydride (1 equivalent) and the polyamine (0.52 equivalents) is heated at reflux in ethanol (0.1M) for 4–48 h. The solid is filtered from the hot mixture and dried to give the free base. The crude material is purified if necessary by heating at reflux in ethanol, filtering the hot suspension, and drying the solid. In some cases, the free base must be purified by column chromatography on silica gel using dichloromethane-methanol mixtures as elutants. The free base is suspended in ethanol (0.1M) and methanesulfonic acid (1.1 equivalents for monoamines, 2.2 equivalents for diamines) is added. This mixture is heated at reflux for 4–24 h. The suspension is cooled to room temperature and the solid is collected on a frit, washed with ethanol, and dried. The crude solid is purified by heating at reflux in ethanol (0.1M). The suspension is filtered hot, and the collected solid is dried to give the bis-imide salt.

Example 1

4-[3-(5-Azaphenanthrene-1,10-dicarboximido) propylamino]-1-(5-azaphenanthrene-1,10-dicarboximido)butane Hydromethanesulfonate 5-Azaphenanthrene-1,10-dicarboxylic anhydride (Zinke, A.; Raith, E. *Monatsh. Chem.* 1919, 40, 271) was condensed with spermidine to give the free base (99%): mp 186°–189° C.; $^1$H NMR (TFA-d, 300 MHz) δ 2.18–2.33 (m, 4H), 2.55–2.66 (m, 2H), 3.53–3.65 (m, 4H), 4.55–4.71 (m, 4H), 7.38–7.53 (m, 1H), 8.41–8.63 (m, 4H), 9.14–9.28 (m, 2H), 9.45–9.60 (m, 6H), 9.61–9.70 (m, 2H);

MS (CI, NH$_3$) m/e (%) 608 (M+H$^+$, 100). The free base was converted to the monomethanesulfonate salt (83%): mp 252°–257° C. (dec); $^1$H NMR (DMSO-d$_6$, 300 MHz) δ 1.68–1.85 (m, 4H), 2.05–2.14 (m, 2H), 2.31 (s, 3H), 2.98–3.15 (m, 4H), 4.13–4.25 (m, 4H), 7.90 (dd, 2H, J=8.0, 4.4 Hz), 8.09 (dd, 2H, J=7.7, 7.3 Hz), 8.28–8.38 (m, 2H), 8.63 (d, 2H, J=7.3 Hz), 8.84 (d, 2H, J=7.6 Hz), 9.04 (s, 2H), 9.23–9.29 (m, 2H), 9.51 (d, 2H, J=8.0 Hz); MS (CI, NH$_3$) m/e (%) 608 (M+H$^+$ free base, 100), 594 (8), 551 (6), 508 (5).

Example 2

Part A: 3-Nitro-5-azaphenanthrene-1,10-dicarboxylic Anhydride

5-Azaphenanthrene-1,10-dicarboxylic anhydride (17.0 g, 68.2 mmol) was dissolved in concentrated sulfuric acid (70 mL) and sodium nitrate (2.90 g, 34.1 mmol) was added to the warm solution. This mixture was heated to 65° C. and three additional aliquots of sodium nitrate (2.90 g, 34.1 mmol) were added after 5, 22, and 30 h. Each aliquot caused about a 20° C. temperature rise, with the temperature stabilizing again at about 65° C. The solution was heated for an additional 14 h after the last addition. The clear orange solution was cooled to room temperature and poured into water (500 mL), washing the residue from the reaction flask with water (5×40 mL). The aqueous suspension was allowed to cool to room temperature. The suspended solid was collected on a frit, washed with water (2×50 mL), and dried. This cream colored solid was heated at reflux in acetic acid (100 mL) containing acetic anhydride (10 mL) for 2 h and cooled to room temperature. The solid was collected on a frit, washed with acetic acid (25 mL) and ether (2×25 mL), and dried to give 18.31 g (91%) of the nitro compound as a cream colored solid: mp 268°–269° C.; $^1$H NMR (DMSO-d$_6$, 300 MHz) δ 8.05 (dd, 1H, J=8.0, 4.4 Hz), 8.97 (dd, 1H, J=8.0, 1.5 Hz), 9.11 (d, 1H, J=2.2 Hz), 9.33–9.40 (m, 2H), 10.16 (d, 1H, J=2.2 Hz); MS (CI, CH$_4$) m/e (%) 295 (M+H$^+$, 100), 265 (6), 250 (5).

Part B: 2-[3-(3-Nitro-5-azaphenanthrene-1,10-dicarboximido)ethylamino]-1-(3-nitro-5-azaphenanthrene-1,10-dicarboximido)ethane Hydromethanesulfonate 3-Nitro-5-azaphenanthrene-1,10-dicarboxylic anhydride was condensed with diethylenetriamine to give the free base (93%): mp 276° C. (dec); $^1$H NMR (TFA-d, 300 MHz) δ 3.90–4.04 (br m, 4H), 4.79–4.93 (br m, 4H), 8.55 (dd, 2H, J=7.5, 6.8 Hz), 9.36 (s, 2H), 9.50–9.63 (m, 4H), 9.54 (s, 2H), 10.35 (s, 2H); MS (CI, NH$_3$) m/e (%) 656 (M+H$^+$, 100), 626 (12), 611 (4), 380 (6), 337 (10), 319 (2). The free base was converted to the monomethanesulfonate salt (42%): mp 272°–275° C. (dec); $^1$H NMR (DMSO-d$_6$, 300 MHz) δ 2.30 (s, 3H), 3.38–3.53 (br m, 4H), 4.39–4.48 (br m, 4H), 8.04 (dd, 2H, J=8.1, 4.4 Hz ), 8.62 (br s, 2H), 8.95 (dd, 2H, J=8.1, 1.5 Hz), 9.10 (d, 2H, J=2.6 Hz ), 9.27 (s, 2H), 9.36 (dd, 2H, J=4.4, 1.5 Hz), 10.15 (d, 2H, J=2.6 Hz ); MS (CI, NH$_3$) m/e (%) 656 (M+H$^+$ free base, 100), 626 (10), 337 (11), 319 (5), 294 (4).

Example 3

3-[2-(3-Nitro-5-azaphenanthrene-1,10-dicarboximido)ethylamino]-1-(3-nitro-5-azaphenanthrene-1,10-dicarboximido)propane Hydromethanesulfonate 3-Nitro-5-azaphenanthrene-1,10-dicarboxylic anhydride was condensed with N-(2-aminoethyl)-1,3-propanediamine to give the free base (96%): mp 257° C. (dec); $^1$H NMR (TFA-d, 300 MHz) δ 2.46–2.59 (br m, 2H), 3.53–3.63 (br m, 2H), 3.86–3.95 (br m, 2H), 4.50–4.60 (br m, 2H), 4.89–4.98 (br m, 2H), 8.54–8.65 (m, 2H), 9.33 (br s, 1H), 9.53–9.70 (m, 6H), 9.73 (br s, 1H), 10.35 (br s, 1H), 10.45 (br s, 1H); MS (CI, NH$_3$) m/e (%) 670 (M+H$^+$, 100) 640 (8) 624 (6) 613 (7), 432 (9), 404 (7), 394 (18), 351 (22), 337 (12). The free base was converted to the monomethanesulfonate salt (60%): mp 263°–265° C. (dec); $^1$H NMR (DMSO-d$_6$, 300 MHz) δ 2.03–2.15 (br m, 2H), 2.32 (s, 3H), 3.14–3.25 (br m, 2H), 3.30–3.45 (br m, obscured by water), 4.21 (br t, 2H, J=6.6 Hz), 4.39–4.48 (br m, 2H), 7.98–8.06 (m, 2H), 8.58 (br s, 2H), 8.95 (s, 1H), 8.98 (s, 1H), 9.10 (s, 2H), 9.26 (d, 2H, J=8.1 Hz), 9.30–9.38 (m, 2H), 10.12 (d, 1H, J=2.2 Hz), 10.15 (d, 1H, J=1.9 Hz); MS (CI, NH$_3$) m/e (%) 670 (M+H$^+$ free base, 100), 640 (8), 625 (6), 375 (5), 351 (7), 327 (7), 294 (6).

Example 4

3-[3-(3-Nitro-5-azaphenanthrene-1,10-dicarboximido)propylamino]-1-(3-nitro-5-azaphenanthrene-1,10-dicarboximido)propane Hydromethanesulfonate 3-Nitro-5-azaphenanthrene-1,10-dicarboxylic anhydride was condensed with 3,3'-iminobispropylamine to give the free base (95%): mp 228° C. (dec); $^1$H NMR (TFA-d, 300 MHz) δ 2.48–2.61 (br m, 4H), 3.45–3.60 (br m, 4H), 4.58–4.70 (br m, 4H), 7.60 (br s, 1H), 8.58 (dd, 2H, J=7.5, 6.8 Hz), 9.56 (d, 2H, J=6.8 Hz), 9.60 (s, 2H), 9.64 (d, 2H, J=7.5 Hz), 9.71 (s, 2H), 10.41 (s, 2H); MS (CI, NH$_3$) m/e (%) 684 (M+H$^+$, 100), 654 (31), 624 (6), 389 (79), 351 (13), 294 (32), 264 (14), 96 (20). The free base was converted to the monomethanesulfonate salt (59%): mp 285°–286° C. (dec); $^1$H NMR (DMSO-d$_6$, 300 MHz) δ 2.03–2.15 (br m, 4H), 2.33 (s, 3H), 3.05–3.19 (br m, 4H), 4.20 (br t, 4H, J=6.6 Hz), 7.98 (dd, 2H, J=8.4, 4.4 Hz), 8.40–8.55 (br s, 2H), 8.88 (dd, 2H, J=8.1, 1.5 Hz), 9.02 (d, 2H, J=2.6 Hz), 9.14 (s, 2H), 9.29 (dd, 2H, J=4.4, 1.5 Hz), 10.00 (d, 2H, J=2.6 Hz); MS (CI, NH$_3$) m/e (%) 684 (M+H$^+$ free base, 92), 654 (13), 627 (10), 389 (100), 351 (15), 294 (37).

Example 5

4-[3-(3-Nitro-5-azaphenanthrene-1,10-dicarboximido)propylamino]-1-(3-nitro-5-azaphenanthrene-1,10-dicarboximido)butane Hydromethanesulfonate 3-Nitro-5-azaphenanthrene-1,10-dicarboxylic anhydride was condensed with spermidine to give the free base (100%): mp 127°–128° C. (dec); $^1$H NMR (TFA-d, 300 MHz) δ 1.98–2.13 (m, 4H), 2.34–2.46 (m, 2H), 3.33–3.45 (m, 4H), 4.35–4.51 (m, 4H), 7.20–7.35 (m, 1H), 8.51 (dd, 2H, J=8.1, 5.8 Hz), 9.43–9.58 (m, 6H), 9.60–9.66 (m, 2H), 10.35 (d, 2H, J=1.1 Hz); MS (CI, NH$_3$) m/e (%) 698 (M+H$^+$, 100), 403 (10), 351 (10), 294 (11). The free base was converted to the monomethanesulfonate salt (73%): mp 298°–301° C. (dec); $^1$H NMR (DMSO-d$_6$, 300 MHz) δ 1.71–1.88 (m, 4H), 2.05–2.16 (m, 2H), 2.32 (s, 3H), 3.03–3.20 (m, 4H), 4.13–4.25 (m, 4H), 7.97 (dd, 1H, J=8.1, 4.4 Hz), 7.98 (dd, 1H, J=8.4, 4.4 Hz), 8.36–8.48 (m, 1H), 8.88 (dd, 1H, J=8.1, 2.9 Hz), 8.89 (dd, 1H, J=8.4, 2.9 Hz), 9.00–9.03 (m, 2H), 9.13 (s, 1H), 9.15 (s, 1H), 9.99 (dd, 2H, J=6.6, 2.6 Hz); MS (CI, NH$_3$) m/e (%) 698 (M+H$^+$ free base, 100), 668 (16), 653 (7), 403 (44), 351 (24), 294 (20).

Example 6

1,2-bis-[2-(3-Nitro-5-azaphenanthrene-1,10-dicarboximido)ethylamino]ethane Dihydromethanesulfonate 3-Nitro-5-azaphenanthrene-1,10-dicarboxylic anhydride was condensed with triethylenetetramine to give the free base (96%): mp 230°–235° C. (dec); $^1$H NMR (TFA-d, 300 MHz) δ 3.81–3.90 (br m, 4H), 3.90–4.00 (br m, 4H), 4.73–4.83 (br m, 4H), 8.53 (dd, 2H, J=7.5, 6.8 Hz), 9.48 (s, 2H), 9.46–9.59 (m, 4H), 9.63 (s, 2H), 10.35 (s, 2H); MS (CI, NH$_3$) m/e (%) 699 (M+H$^+$, 100), 681 (13), 449 (14), 380 (25), 337 (89). The free base was converted to the di-methanesulfonate salt (81%): mp 284.5°–287° C. (dec); $^1$H NMR (TFA-d, 300 MHz) δ 3.20 (s, 6H), 4.02–4.10 (br m, 4H), 4.15–4.20 (m, 4H), 4.94–5.01 (br m, 4H), 8.72 (dd, 2H, J=8.4, 5.5 Hz), 9.68 (s, 2H), 9.71–9.78 (m, 4H), 9.87 (d, 2H, J=2.2 Hz), 10.60 (d, 2H, J=1.8 Hz); MS (CI, NH$_3$) m/e (%) 699 (M+H$^+$ free base, 21), 681 (23), 449 (5), 380 (29), 360 (42), 337 (100).

Example 7

(S,S)-1,2-bis-[2-(3-Nitro-5-azaphenanthrene-1,10-dicarboximido) propylamino]ethane Dihydromethanesulfonate 3-Nitro-5-azaphenanthrene-1,10-dicarboxylic anhydride was condensed with (S, S)-1,2-bis-(2-aminopropylamino)ethane (U.S. patent application Ser. No. 92/02134) to give the free base, which was converted directly to the di-methanesulfonate salt (48%): mp 220°–222° C. (dec); $^1$H NMR (DMSO-d$_6$, 300 MHz) δ 1.62 (d, 6H, J=6.9 Hz), 2.26 (s, 6H), 3.25–3.38 (br m, 4H), 3.40–3.55 (br m, obscured by water), 3.85–4.03 (br m, 2H), 5.45–5.58 (br m, 2H), 8.00–8.08 (m, 2H), 8.74–8.89 (br m, 2H), 8.97 (d, 2H, J=8.1 Hz ), 9.10 (d, 2H, J=0.8 Hz ), 9.25 (s, 2H), 9.37 (d, 2H, J=2.9 Hz), 10.13 (br s, 2H); MS (FAB) m/e (% ) 727 (M+H$^+$ free base, 100), 711 (17), 334 (96), 307 (19), 288 (25). [α]$_D^{25}$+46.69° (c=0.604 g/dL, DMSO).

Example 8

(R,R)-1,2-bis-[2-(3-Nitro-5-azaphenanthrene-1,10-dicarboximido)propylamino]ethane Dihydromethanesulfonate 3-Nitro-5-azaphenanthrene-1,10-dicarboxylic anhydride (11.08 g, 37.6 mmol) was heated at reflux in dioxane (160 mL) and a solution of (R,R)-1,2-bis-(2-aminopropylamino) ethane (U.S. patent application Ser. No. 92/02134) (3.34 g, 19.2 mmol) in dioxane (30 mL) was added. This mixture was heated for 2 h and cooled. Triethylamine (13.1 mL, 94.0 mmol) and chlorotrimethylsilane (10.5 mL, 82.7 mmol) were added. The orange mixture was heated at reflux for 3 h, cooled to room temperature, and poured into water (500 mL), rinsing the flask with water (50 mL). The orange, suspended solid was collected on a frit and dried. This material was suspended in 95% aqueous ethanol (375 mL) and methanesulfonic acid (2.7 mL, 41.4 mmol) was added. The tan suspension was heated at reflux for 18 h, cooled to room temperature, and filtered. The collected solid was washed with ethanol (2×50 mL) and dried to give 14.69 g of a flight orange solid. The crude salt was suspended in dichloromethane (200 mL) and neutralized by the addition of triethylamine (10 mL). The cloudy brown mixture was applied to an 8×22 cm column and flash chromatographed using a base solvent of 0.1% triethylamine in dichloromethane and eluting initially with 2% added methanol and increasing gradually to 4% added methanol. The free base was obtained as a light brown/orange solid (9.24 g), after the elution of some orange impurities. The free base was suspended in dichloromethane (200 mL) containing methanesulfonic acid (1.7 mL, 26.8 mmol) and stirred at room temperature for 3 days. The yellow suspension was filtered, the collected solid was washed with dichloromethane (50 mL), and dried. This material was heated at reflux in ethanol (150 mL) for 3 h and filtered hot. The collected solid was washed with ethanol (50 mL) and dried, including 5 days at 100° C. under vacuum, to give 10.11 g (58%) of a tan solid: mp 211°–215° C. (dec); $^1$H NMR (TFA-d, 300 MHz) δ 1.82 (d, 6H, J=7.0 Hz), 3.05 (s, 6H), 3.73 (br d, 2H, J=12.1 Hz), 3.91–4.09 (m, 4H), 4.45 (dd, 2H, J=12.8, 9.9 Hz), 5.79–5.92 (m, 2H), 8.59 (dd, 2H, J=8.0, 5.9 Hz), 9.50 (s, 2H), 9.60 (d, 2H, J=8.8 Hz), 9.63 (d, 2H, J=5.5 Hz), 9.70 (d, 2H, J=1.1 Hz), 10.45 (d, 2H, J=1.4 Hz); MS (CI, NH$_3$) m/e (%) 727 (M+H$^+$ free base, 82), 709 (100), 707 (36), 697 (12), 377 (18), 374 (53), 351 (78), 349 (32), 333 (77); [α]$_D^{25}$−30.07° (C=0.616 g/dL, DMSO). Anal. Calculated for C$_{40}$H$_{38}$N$_8$O$_8$S$_2$: C, 52.28; H, 4.17; N, 12.19; S, 6.98. Found: C, 52.23; H, 4.13; N, 12.15; S, 6.94.

Example 9

Part A: 3-Amino-5-azaphenanthrene-1,10-dicarboxylic Anhydride Hydrochloride

A suspension of 3-nitro-5-azaphenanthrene-1,10-dicarboxylic anhydride (2.00 g, 6.8 mmol) in 66% aqueous ethanol (39 mL) was heated to about 60° C. in a mechanically stirred 250 mL three-necked flask. Sodium dithionite (3.43 g, 19.7 mmol) was added in portions over 30 min and the mixture was heated at reflux for 1 h. The orange suspension was cooled to room temperature and diluted with water (150 mL). The suspended, orange solid was collected on a frit, washed with water (50 mL), and dried. The solid was heated on a steam bath in concentrated hydrochloric acid (20 mL) for 10 min and filtered hot to remove an undissolved solid (mainly unreacted nitro compound). The filtrate was cooled to room temperature and poured into water (50 mL). The precipitated orange solid was collected on a frit, washed with water (2×10 mL), and dried. This material was heated in concentrated hydrochloric acid (20 mL) and worked up as above to give 0.81 g (39%) of an orange solid: mp >304° C.; $^1$H NMR (DMSO-d$_6$, 300 MHz) δ 5.55 (br s, 2H), 7.81 (dd, 1H, J=8.0, 4.4 Hz), 7.96 (d, 1H, J=2.2 Hz), 8.60 (d, 1H, J=2.5 Hz), 8.66 (s, 1H), 8.70 (dd, 1H, J=8.0, 1.5 Hz), 9.13 (dd, 1H, J=4.4, 1.5 Hz); MS (CI, CH$_4$) m/e (%) 265 (M+H$^+$, 100).

Part B: 4-[3-(3-Amino-5-azaphenanthrene-1,10-dicarboximido)-propylamino]-1-(3-amino-5-azaphenanthrene-1,10-dicarboximido)butane Trihydromethanesulfonate 3-Amino-5-azaphenanthrene-1,10-dicarboxylic anhydride hydrochloride was condensed with spermidine and the initially collected solid was suspended in 0.1M sodium hydroxide solution and filtered to give the free base (62%): mp 263°–267° C. (dec); $^1$H NMR (TFA-d, 300 MHz) δ 1.95–2.18 (br m, 4H), 2.38–2.53 (br m, 2H), 3.33–3.53 (br m, 4H), 4.38–4.56 (br m, 4H), 7.34 (br s, 1H), 8.50–8.60 (m, 2H), 9.27 (d, 2H, J=6.2 Hz), 9.46 (br s, 1H), 9.48 (br s, 1H), 9.52 (s, 1H), 9.55 (s, 1H), 9.62 (d, 2H, J=7.7 Hz), 9.83 (br s, 2H); MS (CI, NH$_3$) m/e (%)

638 (M+H+, 100), 373 (3), 264 (5), 210 (3), 193 (14), 176 (4). The free base was reacted with methanesulfonic acid (3.1 equivalents) to give the tri-methanesulfonate salt (13%): mp 285°-288° C. (dec); $^1$H NMR (DMSO-$d_6$, 300 MHz) δ 1.63-1.78 (br m, 4H), 1.96-2.08 (br m, 2H), 2.36 (s, 9H), 2.93-3.08 (br m, 4H), 4.06-4.18 (m, 4H), 7.79 (dd, 2H, J=8.1, 4.4 Hz), 7.98-8.02 (m, 2H), 8.22-8.34 (br m, 1H), 8.58-8.62 (m, 4H), 8.70 (dd, 2H, J=8.1, 1.5 Hz), 9.11 (dd, 2H, J=4.4, 1.5 Hz); MS (CI, NH$_3$) m/e (%) 638 (M+H+ free base, 100), 373 (3), 321 (3), 303 (2), 264 (5).

Example 10

Part A: 7-Methyl-5-azaphenanthrene-1,10-dicarboxylic Anhydride

A mixture of 4-amino-1,8-naphthalic anhydride (Okazaki, M.; Ishikawa, N. *Yuki Gosei Kagaku Kyokai Shi* 1956, 14, 398; *Chem. Abstr.* 1957, 51, 8051c) (28.0 g, 131 mmol), ferrous sulfate heptahydrate (7.20 g, 25.8 mmol), concentrated sulfuric acid (13 mL, 234 mmol), and nitrobenzene (27.0 mL, 262 mmol) in acetic acid (260 mL) was heated to reflux. Methallylidene diacetate (43.5 mL, 262 mmol) was added dropwise over a period of 2.5 h using an addition funnel. After the addition was complete, the reaction mixture was heated for 1.5 h and poured into a beaker of ice/water (500 mL). The aqueous solution was further diluted to 800 mL with water, stirred for 1 h and filtered by suction. The residue was washed with water and dried in vacuo to obtain 32.3 g of a dark brown solid. The crude solid was heated at reflux in acetic acid (80 mL) and filtered hot to obtain 15.63 g (44%) of a light brown solid: mp >290° C.; MS m/e 264 (M+H+); $^1$H NMR (DMSO-$d_6$, 300 MHz) δ 2.60 (s, 3H), 8.10 (t, 1H), 8.60 (s, 1H), 8.62 (s, 1H), 9.01 (s, 1H), 9.12 (d, 1H), 9.45 (d, 1H).

Part B:
4-[3-(7-Methyl-5-azaphenanthrene-1,10-dicarboximido)propylamino]-1-(7-methyl-5-azaphenanthrene-1,10-dicarboximido)butane Hydromethanesulfonate 7-Methyl-5-azaphenanthrene-1,10-dicarboxylic anhydride was condensed with spermidine to give the free base (25%): mp 268°-272° C.; MS m/e 636 (M+H+); $^1$H NMR (TFA-d, 300 MHz) δ 2.04 (br m, 4H), 2.50 (m, 2H), 2.90 (s, 6H), 3.70 (m, 4H), 4.50 (m, 4H), 7.30 (br s, 1H), 8.30 (br s, 2H), 9.02 (d, 2H), 9.20 (br s, 2H), 9.30-9.50 (br m, 6H). The free base was converted to the mono-methanesulfonate salt (25%): mp 198°-200° C.; MS m/e 636 (M+H+); $^1$H NMR (TFA-d, 300 MHz) δ 2.10 (br m, 4H), 2.50 (m, 2H), 2.90 (s, 6H), 3.10 (br s, 3H), 3.48 (m, 4H), 4.50 (m, 4H), 7.30 (t, 1H), 8.30 (br s, 2H), 9.08 (d, 2H), 9.20-9.50 (m, 8H).

Example 11

Part A: 8-Nitro-10-azaacephenanthrene

A mixture of 5-aminoacenaphthene (Grabe, C. *Liebigs Ann. der Chemie* 1903, 327, 77) (5.0 g, 29.5 mmol) and sodium nitromalondialdehyde monohydrate (Fanta, P. E. *Org. Syntheses Coll.* vol. 4 1963, 844) (5.51 g, 35 mmol) in acetic acid (140 mL) was stirred for 1 h at room temperature and aniline hydrochloride (5.21 g, 40.2 mmol) was added. This mixture was stirred for 10 min and heated at reflux for 2 h. Phosphorous oxychloride (3 mL, 32.2 mmol) was added and heating was continued for 3 h. The resulting mixture was cooled to room temperature and poured into ice/water (200 mL). The aqueous mixture was neutralized with 2M sodium hydroxide solution and extracted with dichloromethane. The extracts were dried over sodium sulfate and condensed to dryness. The condensed product was purified using flash chromatography (20% hexane/dichloromethane, silica gel) to obtain a fluffy, bright yellow solid, 3.20 g (43%): MS m/e 251 (M+H+); $^1$H NMR (CD2Cl$_2$, 300 MHz) δ 3.48-3.55 (m, 4H), 7.56 (s, 1H), 7.68 (d, J=7.0 Hz, 1H), 7.77 (t, J=7.8 Hz, 1H), 8.79 (d, J=8.1 Hz, 1H), 8.94 (d, J=2.5 Hz, 1H), 9.65 (d, J=2.5 Hz, 1H).

Part B: 7-Nitro-5-azaphenanthrene-1,10-dicarboxylic Anhydride

8-Nitro-10-azaacephenanthrene (3.0 g, 24 mmol) was heated to 70° C. in acetic acid (100 mL) and sodium dichromate dihydrate (18.0 g, 60.4 mmol) was added. The reaction mixture was heated at reflux for 4 h and poured into ice/water. The precipitated solid was collected and dried in vacuo to obtain 1.64 g (34%) of a yellow solid. The crude material was heated at reflux in a mixture of acetic acid (25 mL) and acetic anhydride (5 mL) for 3 h. The mixture was filtered hot and the collected solid was dried in vacuo to give 0.90 g (17%) of a light brown solid: mp 290°-292° C.; MS m/e 312 (M+NH$_4$+); $^1$H NMR (DMSO-$d_6$, 300 MHz) δ 8.19 (t, J=4.0 Hz, 1H), 8.73 (d, J=7.3 Hz, 1H), 9.33 (s, 1H), 9.54 (d, J=8.0 Hz, 1H), 9.80 (d, J=2.5 Hz, 1H), 9.90 (d, J=2.0 Hz, 1H).

Part C:
4-[3-(7-Nitro-5-azaphenanthrene-1,10-dicarboximido)propylamino]-1-(7-nitro-5-azaphenanthrene-1,10-dicarboximido)butane Hydromethanesulfonate 7-Nitro-5-azaphenanthrene-1,10-dicarboxylic anhydride was reacted with spermidine to give the free base (75%): MS m/e 698 (M+H+); $^1$H NMR (TFA-d, 300 MHz) δ 2.19 (br s, 4H), 2.50 (m, 2H), 3.50 (br s, 4H), 4.55 (m, 4H), 7.45 (br s, 1H), 8.51 (t, 2H), 9.20 (m, 2H), 9.60 (d, 2H), 9.61 (d, 2H), 10.45 (s, 2H), 10.65 (s, 2H). The free base was converted to the monomethanesulfonate salt (92%): mp 228°-230° C.; MS m/e 698 (M+H+); $^1$H NMR (TFA-d, 300 MHz) δ 2.19 (br m, 4H), 2.50 (m, 2H), 3.15 (s, 3H), 3.50 (br m, 4H), 4.55 (m, 4H), 7.38 (br s, 1H), 8.28 (t, 2H), 9.20 (m, 2H), 9.60 (d, 2H), 9.61 (d, 2H), 10.45 (s, 2H), 10.65 (s, 2H).

Example 12

Part A:
3-Nitro-7-methyl-5-azaphenanthrene-1,10-dicarboxylic Anhydride

7-Methyl-5-azaphenanthrene-1,10-dicarboxylic anhydride was nitrated as in example 2, part A at 110° C. to give the nitrated derivative (78%): mp 261°-262° C.; $^1$H NMR (CDCl$_3$, 300 MHz) δ 2.72 (s, 3H), 8.32 (m, 1H), 9.12 (s, 1H), 9.16 (d, 1H, J=2.2 Hz), 9.45 (d, 1H, J=2.2 Hz), 10.45 (d, 1H, J=2.2 Hz); MS (CI, NH$_3$) m/e (%) 326 (M+NH$_4$+, 3), 309 (M+H+, 16), 279 (M+H+—NO, 100).

Part B:
4-[3-(3-Nitro-7-methyl-5-azaphenanthrene-1,10-dicarboximido)propylamino]-1-(3-nitro-7-methyl-5-azaphenanthrene-1,10-dicarboximido)butane Hydromethanesulfonate 3-Nitro-7-methyl-5-azaphenanthrene-1,10-dicarboxylic anhydride was condensed with spermidine to give the free base (47%): mp 224°-228° C.; MS m/e 726

(M+H+); ¹H NMR (TFA-d, 300 MHz) δ 2.14 (br m, 4H), 2.47–2.49 (m, 2H), 2.94 (s, 6H), 3.48 (m, 4H), 4.50–4.56 (m, 4H), 7.40 (br s, 1H), 9.37 (br s, 2H), 9.44 (br s, 2H), 9.53 (d, 2H), 9.70 (d, 2H), 10.36 (br s, 2H). The free base was converted to the monomethanesulfonate salt (51%): mp >280° C.; MS m/e 726 (M+H+); 1H NMR (TFA-d, 300 MHz) δ 2.10 (br m, 4H), 2.50 (m, 2H), 2.95 (s, 6H), 3.20 (s, 3H), 3.45 (m, 4H), 4.50 (m, 4H), 7.40 (br s, 1H), 9.42 (br s, 4H), 9.52 (d, 2H), 9.70 (d, 2H), 10.40 (br s, 2H); HRMS Calculated for $C_{39}H_{31}N_7O_8$: 726.2312. Found: 726.2329.

Example 13

(R,R)-1,2-bis-[2-(3-Nitro-7-methyl-5-azaphenanthrene-1,10-dicarboximido)propylamino]ethane Dihydromethanesulfonate 3-Nitro-7-methyl-5-azaphenanthrene-1,10-dicarboxylic anhydride (14.98 g, 48.6 mmol) was suspended in dioxane (220 mL) and heated to reflux. A solution of (R,R)-1,2-bis-(2-aminopropylamino)ethane (U.S. patent application Ser. No. 92/02134) (4.32 g, 24.8 mmol) in dioxane (30 mL) was added and the mixture was heated for 5 h. The orange suspension was cooled to room temperature and triethylamine (16.9 mL, 121.5 mmol) and chlorotrimethylsilane (13.6 mL, 106.9 mmol) were added. This mixture was heated at reflux for 3 h, cooled to room temperature, and poured into water (700 mL), rinsing the flask with water (50 mL). The suspended solid was collected on a frit, washed with water (2×100 mL), and partially dried. This material was heated at reflux in 95% aqueous ethanol (500 mL) containing methanesulfonic acid (3.5 mL, 53.5 mmol) for 18 h in a 1L, 3-necked, mechanically stirred flask, gradually changing from a dark orange to a light yellow color. The yellow solid was collected from the hot suspension, washed with ethanol (2×100 mL), and dried. The crude material was heated successively in 95% aqueous ethanol (500 mL), 95% aqueous acetonitrile (500 mL), 95% aqueous isopropanol (500 mL), acetonitrile (500 mL), and chloroform (500 mL), each time the solid was collected from the hot suspension, washed with the main solvent (25 mL), and dried. This material was suspended in ether (100 mL), filtered, and the resulting solid was heated at reflux in ethanol (150 mL) containing methanesulfonic acid (0.1 mL) for 3 h and filtered hot. The solid was washed with ethanol (2×25 mL) and dried, including 3 days at 85° C. under high vacuum to give 11.85 g (51%) of a yellow solid: mp 221°–223.5° C. (dec); 1H NMR (TFA-d, 300 MHz) δ 1.85 (d, 6H, J=6.6 Hz), 3.02 (s, 6H), 3.08 (s, 6H), 3.74 (br d, 2H, J=12.4 Hz), 3.92–4.12 (m, 4H), 4.44 (dd, 2H, J=12.4, 10.2 Hz), 5.84–5.95 (br m, 2H), 9.39 (s, 2H), 9.45 (s, 2H), 9.47 (s, 2H), 9.70 (s, 2H), 10.43 (s, 2H); MS (CI, NH3) m/e (%) 755 (M+H+ free base, 45), 737 (75), 388 (34), 365 (43), 347 (55), 131 (100); $[\alpha]_D^{25}$ −30.36° (C=0.606 g/dL, DMSO).

Example 14

Part A: Methyl α-[(4-Pyridyl)methylene]-(2-carboxyphenyl)acetate

Dimethyl homophthalate (Sheehan, J. C.; O'Neil, R. C. *J. Am. Chem. Soc.* 1950, 72, 4614) (13.25 g, 63.7 mmol) was dissolved in dry tetrahydrofuran (120 mL). Pyridine-4-carboxaldehyde (6.1 mL, 63.7 mmol) was added and the resultant solution cooled to 0° C. under nitrogen. Sodium hydride (2.8 g of a 60% oil dispersion, 70.0 mmol) was added in portions. When the addition was complete, the reaction was allowed to warm to room temperature and was stirred for one hour. The reaction was diluted with ether (200 mL) and filtered. The residue was dissolved in water (250 mL) and the pH adjusted to 5 with 1 N aqueous oxalic acid. The precipitate was collected and dried in vacuo using a phosphorus pentoxide trap. The stilbene product was isolated as a colorless solid (14.28 g, 79%): ¹H NMR (300 MHz, CD$_{30}$D) δ 8.31 (2H, d), 8.16 (1H, dd), 7.49 (2H, m), 7.29 (1H, s), 7.05 (1H, d), 6.97 (2H, d), 3.72 (3H, s) ; MS (CH$_4$ CI) m/e 284 (M+H), 312 (M+C$_2$H$_5$), 324 (M+C$_3$H$_5$).

Part B: 6-Azaphenanthrene-1,10-dicarboxylic Anhydride

Methyl α-[(4-pyridyl)methylene]-(2-carboxyphenyl)acetate (147.6 mg, 0.522 mmol) was suspended in absolute ethanol (200 mL) in a quartz reaction flask. Iodine (136.1 mg, 0.537 mmol) was added and the vessel was flushed with nitrogen. The reaction was photolyzed for two hours using a Rayonet photochemical reactor (Model RPR-100, circa 35 watts at 254 nm). A solution of sodium hydroxide (1.1 mL, 1.0 N, 1.1 mmol) was added followed by saturated sodium bisulfite (0.5 mL). The solvent was removed on a rotary evaporator and the residue suspended in water (5.0 mL). The solid was collected by filtration and washed with water. After standing overnight, an additional crop of solid was isolated from the mother liquor. The combined solids were suspended in acetic anhydride (2.0 mL) and heated on a steam bath for approximately 15 min. The solution was allowed to stand at room temperature overnight. The product anhydride was isolated by filtration and washed with ethyl acetate. Removal of residual solvent in vacuo provided the desired product (73.3 mg, 56%): ¹H NMR (300 MHz, CDCl$_3$) δ 10.22 (1H, s), 9.23 (1H, d), 8.99 (1H, s), 8.98 (1H, d), 8.76 (1H, d), 8.10 (1H, t), 8.01 (1H, d); MS (CH$_4$ CI) m/e 250 (M+H), 278 (M+C$_2$H$_5$), 290 (M+C$_3$H$_5$); HRMS Calculated for $C_{15}H_7NO_3$: 249.0426. Found: 249.0433.

Part C: 4-[3-(6-Azaphenanthrene-1,10dicarboximido)-propylamino]-1-(6-azaphenanthrene-1,10-dicarboximido)butane Trihydromethanesulfonate 6-Azaphenanthrene-1,10-dicarboxylic anhydride was condensed with spermidine to give the free base, which was converted directly to the trimethanesulfonate salt by reaction with methanesulfonic acid (4 equivalents) (45%): mp 190°–195° C.; ¹H NMR (300 MHz, TFA-d) δ 10.57 (2H, s), 9.38–9.34 (4H, s+d, J=8.8 Hz), 9.00 (4H, m), 8.84 (2H, d, J=7.4 Hz), 8.40 (2H, t, J=7.7 Hz), 7.24 (1H, m), 4.58–4.51 (2H, m), 4.50–4.40 (2H, m), 3.54–3.43 (4H, m), 3.17 (9H, s), 2.54–2.45 (2H, m), 2.18–2.10 (4H, m); MS (NH$_3$ CI) m/e 608 (M+H); IR (Nujol) 3500 (br), 1707, 1666, 1211, 1153, 1040 cm$^{-1}$.

Example 15

Part A: 7-Azaphenanthrene-1,10-dicarboxylic Anhydride

As described in example 14, the following compounds were prepared from dimethyl homophthalate and pyridine-3-carboxaldehyde:
Methyl α-[(3-pyridyl)methylene]-(2-carboxyphenyl)acetate: ¹H NMR (300 MHz, CDCl$_3$) δ 8.43 (1H, d), 8.38 (1H, s), 8.21 (1H, m), 7.78 (1H, s), 7.49 (2H, m), 7.10 (3H, m), 3.75 (3H, s); MS (CH$_4$ CI) m/e 284

(M+H), 312 (M+C$_2$H$_5$), 324 (M+C$_3$H$_5$); HRMS Calculated for C$_{16}$H$_{13}$NO$_4$: 283.0844. Found: 283.0845.

7-Azaphenanthrene-1,10-dicarboxylic anhydride was obtained along with the 5-aza isomer from the photolysis of methyl α-[(3-pyridyl)methylene]-(2-carboxyphenyl)acetate. They were separated by chromatography on silica gel using isopropanol/chloroform as the elutant: $^1$H NMR (300 MHz, CDCl$_3$) δ 9.56 (1H, s), 9.13 (1H, s), 9.09 (1H, d), 9.04 (1H, d), 8.81 (1H, d), 8.52 (1H, d), 8.07 (1H, t); MS (CH$_4$ CI) m/e 250 (M+H), 278 (M+C$_2$H$_5$), 290 (M+C$_3$H$_5$).

Part B:
4-[3-(7-Azaphenanthrene-1,10-dicarboximido)-propylamino]-1-(7-azaphenanthrene-1,10-dicarboximido)butane 2.5-Hydromethanesulfonate 7-Azaphenanthrene-1,10-dicarboxylic anhydride was condensed with spermidine to give the free base, which was converted directly to the 2.5-methanesulfonate salt by reaction with methanesulfonic acid (4 equivalents): mp 265°–272° C. (dec).

Example 16

Part A: 3-Nitro-7-azaphenanthrene-1,10-dicarboxylic Anhydride

7-Azaphenanthrene-1,10-dicarboxylic anhydride was nitrated in a similar fashion to the 5-aza derivative, Example 2, part A: $^1$H NMR (300 MHz, CDCl$_3$) δ 10.16 (1H, s), 9.83 (1H, s), 9.44 (1H, s), 9.16 (3H, m) ; MS (CH$_4$ CI) m/e 295 (M+H), 323 (M+C$_2$H$_5$), 335 (M+C$_3$H$_5$).

Part B:
4-[3-(3-Nitro-7-azaphenanthrene-1,10-dicarboximido)-propylamino]-1-(3-nitro-7-azaphenanthrene-1,10-dicarboximido)butane 2.6-Hydromethanesulfonate 3-Nitro-7-azaphenanthrene-1,10-dicarboxylic anhydride was condensed with spermidine to give the free base, which was converted directly to the 2.6-methanesulfonate salt by reaction with methanesulfonic acid (4 equivalents): mp 195°–200° C.; $^1$H NMR (300 MHz, TFA-d) δ 10.24 (2H, d, J=1.8 Hz), 10.15 (2H, s), 9.80 (2H, d, J=1.8 Hz), 9.76 (2H, d, J=1.1 Hz), 9.57 (2H, d, J=5.2 Hz), 9.23 (2H, d, J=6.2 Hz), 7.30 (1H, m), 4.59–4.54 (2H, m), 4.53–4.48 (2H, m), 3.53–3.44 (4H, m), 3.16 (7.8H, s), 2.54–2.48 (2H, m), 2.19–2.14 (4H, m); MS (NH$_3$ CI) m/e 698 (M+H); IR (KBr) 3490 (br), 3000 (br), 1711, 1666, 1515, 1345, 1209, 1192, 1059 cm$^{-1}$.

Example 17

4-[3-(8-Azaphenanthrene-1,10-dicarboximido)-propylamino]-1-(8-azaphenanthrene-1,10-dicarboximido)butane Hydromethanesulfonate 8-Azaphenanthrene-1,10-dicarboxylic anhydride (Peters, A. T.; Bide, M. J. *Dyes and Pigments* 1985, 6, 349) was condensed with spermidine to give the free base (53%): mp 241°–249° C. (dec); $^1$H NMR (TFA-d, 300 MHz) δ 2.13–2.33 (br m, 4H), 2.48–2.68 (br m, 2H), 3.45–3.60 (m, 4H), 4.50–4.68 (br m, 4H), 8.38–8.48 (br m, 2H), 8.55–8.66 (br m, 2H), 9.05–9.15 (br m, 2H), 9.38–9.63 (br m, 6H), 10.13–10.23 (br m, 2H); MS (CI, NH$_3$) m/e (%) 608 (M+H$^+$, 100), 572 (5), 358 (2). The free base was converted to the mono-methanesulfonate salt (86%): mp 243°–247° C. (dec); $^1$H NMR (DMSO-d$_6$, 300 MHz) δ 1.63–1.81 (br m, 4H), 1.98–2.10 (m, 2H), 2.94–3.10 (br m, 4H), 2.30 (s, 3H), 4.13 (t, 2H, J=6.6 Hz), 4.16 (t, 2H, J=6.6 Hz), 7.97 (dd, 2H, J=8.4, 4.0 Hz), 8.09 (t, 2H, J=7.7 Hz), 8.25–8.36 (br m, 2H), 8.60 (d, 2H, J=7.3 Hz), 9.18 (d, 2H, J=4.1 Hz), 9.33 (d, 2H, J=8.5 Hz), 9.44 (d, 2H, J=8.4 Hz); MS (CI, NH$_3$) m/e (%) 608 (M+H$^+$ free base, 100), 358 (5), 306 (3), 249 (7).

Example 18

Part A: 3-Nitro-8-azaphenanthrene-1,10-dicarboxylic Anhydride

As above for example 2, part A, 8-azaphenanthrene-1,10-dicarboxylic anhydride (7.62 g, 30.6 mmol) was nitrated in concentrated sulfuric acid (30 mL) at 110° C. by the addition of sodium nitrate (6.50 g, 76.5 mmol) in five portions over 31 h. The acid solution was poured into water (300 mL), rinsing the residue from the reaction flask with water (4×25 mL). The aqueous suspension was neutralized to about pH 4 with concentrated sodium hydroxide solution and sodium acetate (5 g) was added as a buffer. The precipitated solid was collected on a frit and dried. The crude material was heated at reflux in acetic acid (70 mL) and acetic anhydride (10 mL) for 4 h and the suspension was cooled to room temperature. The brown solid was collected on a frit, washed with acetic acid (20 mL), and dried to give 5.94 g (66%) of the nitro compound: mp >300° C.; $^1$H NMR (CDCl$_3$, 300 MHz) δ 7.97 (dd, 1H, J=9.0, 4.5 Hz), 9.16 (d, 1H, J=9.0 Hz), 9.33 (d, 1H, J=4.5 Hz), 9.42 (s, 1H), 9.48 (d, 1H, J=1.5 Hz), 9.87 (d, 1H, J=1.5 Hz); MS (CI, CH$_4$) m/e (%) 295 (M+H$^+$, 100), 250 (4), 121 (6), 103 (4), 93 (19).

Part B:
4-[3-(3-Nitro-8-azaphenanthrene-1,10-dicarboximido)-propylamino]-1-(3-nitro-8-azaphenanthrene-1,10-dicarboximido)butane Hydromethanesulfonate 3-Nitro-8-azaphenanthrene-1,10-dicarboxylic anhydride was condensed with spermidine to give the free base (93%): mp >300° C.; $^1$H NMR (TFA-d, 300 MHz) δ 2.06–2.18 (br m, 4H), 2.40–2.53 (br m, 2H), 3.40–3.53 (br m, 4H), 4.43–4.58 (br m, 4H), 7.25–7.35 (br m, 1H), 8.58–8.66 (m, 2H), 9.44–9.53 (br s, 2H), 9.61 (br d, 2H, J=4.5 Hz), 9.64–9.70 (br s, 2H), 10.18 (br s, 2H), 10.23 (br d, 2H, J=8.2 Hz); MS (CI, NH$_3$) m/e (%) 698 (M+H$^+$, 50), 446 (10), 403 (65), 351 (62), 294 (100), 264 (21). The free base was converted to the mono-methanesulfonate salt (84%): mp 212°–215° C. (dec); $^1$H NMR (DMSO-d$_6$, 300 MHz) δ 1.70–1.86 (br m, 4H), 2.03–2.15 (br m, 2H), 2.32 (s, 3H), 2.99–3.16 (m, 4H), 4.09–4.24 (m, 4H), 7.94–8.01 (m, 2H), 8.33–8.48 (br m, 1H), 8.88 (s, 2H), 9.02 (s, 2H), 9.22 (br s, 2H), 9.55 (dd, 2H, J=7.7, 1.1 Hz), 9.93 (d, 2H, J=2.6 Hz); MS (CI, CH$_4$) m/e (%) 698 (M+H$^+$ free base, 60), 668 (4), 403 (42), 365 (35), 351 (52), 294 (100).

Example 19

1,2-bis-[2-(3-Nitro-8-azaphenanthrene-1,10-dicarboximido)ethylamino]ethane Dihydromethanesulfonate 3-Nitro-8-azaphenanthrene-1,10-dicarboxylic anhydride was condensed with triethylenetetramine to give the free base (81%): mp >295° C.; $^1$H NMR (TFA-d, 300 MHz) δ 3.88–3.95 (br m, 4H), 3.98–4.04 (m, 4H), 4.80–4.88 (br m, 4H), 8.68 (dd, 2H, J=9.1, 5.5 Hz), 9.54 (d, 2H, J=5.5 Hz), 9.60 (s, 2H), 9.69 (d, 2H, J=2.2 Hz), 10.25 (d, 2H, J=2.2 Hz), 10.29 (dd, 2H, J=8.8, 0.8 Hz); MS (CI, NH$_3$) m/e (%) 699 (M+H$^+$, 19), 681 (9), 449 (16), 380 (26), 354 (23), 337 (100). The free base was converted to the di-methanesulfonate salt (28%): mp 267°-270° C. (dec); $^1$H NMR (TFA-d, 300 MHz) δ 3.21 (s, 6H), 4.09–4.18 (br m, 4H), 4.20–4.26 (br m, 4H), 5.00–5.09 (br m, 4H), 8.80–8.88 (m, 2H), 9.72 (d, 2H, J=4.5 Hz), 9.78 (s, 2H), 9.88 (s, 2H), 10.40 (s, 2H), 10.45 (d, 2H, J=8.2 Hz); MS (CI, NH$_3$) m/e (%) 699 (M+H$^+$ free base, 22), 681 (7), 656 (15), 380 (24), 337 (100), 319 (24), 294 (27).

Example 40

4-[3-(Phenanthrene-1,10-dicarboximido)propylamino]-1-(phenanthrene-1,10-dicarboximido)butane Hydromethanesulfonate Phenanthrene-1,10-dicarboxylic anhydride (Fieser, L. F.; Peters, M. A. *J. Am. Chem. Soc.* 1932, 54, 4373) was condensed with spermidine and the free base was converted to the mono-methanesulfonate salt: MS (CI) m/e (%) 606 (M+H$^+$, 100); $^1$H NMR (TFA-d, 300 MHz) δ 9.15 (m, 4H), 8.69 (m, 4H), 8.20 (m, 2H), 8.00 (m, 4H), 7.80 (m, 2H), 7.30 (m, 2H), 4.50 (m, 4H), 3.50 (m, 4H), 3.20 (s, 3H), 2.45-(m, 2H), 2.19 (m, 4H).

Example 41

Part A: 6-Methylphenanthrene-1,10-dicarboxylic Anhydride

As described in example 14, the following compounds were prepared from dimethyl homophthalate and p-tolualdehyde:

Methyl α-[(4-methylphenyl)methylene]-(2-carboxyphenyl)acetate: $^1$H NMR (300 MHz, CDCl$_3$) δ 8.24 (1H, br d), 7.80 (1H, s), 7.48 (2H, m), 7.15 (1H, d), 6.94 (2H, d), 6.83 (2H, d), 3.73 (3H, s), 2.25 (3H, s) ; MS (CH$_4$ CI) m/e 265 (M+H—MeOH), 279 (M+H—H$_2$O), 293 (M+C$_2$H$_5$—MeOH), 297 (M+H), 305 (M+C$_3$H$_5$—MeOH), 325 (M+C$_2$H$_5$).

6-Methylphenanthrene-1,10-dicarboxylic anhydride: $^1$H NMR (300 MHz, CDCl$_3$) δ 9.05 (1H, d), 8.98 (1H, s), 8.65 (1H, d), 8.54 (1H, s), 8.07 (1H, d), 7.94 (1H, t), 7.65 (1H, d), 2.73 (3H, s).

Part B:
4-[3-(6-Methylphenanthrene-1,10-dicarboximido)-propylamino]-1-(6-methylphenanthrene-1,10-dicarboximido)butane Hydromethanesulfonate 6-Methylphenanthrene-1,10-dicarboxylic anhydride was condensed with spermidine and the free base was converted directly to the monomethanesulfonate salt: mp 165°-170° C.

Example 42

Part A:
7-Hydroxy-7-methyl-7,8,9,10-tetrahydroacephenanthrene

Methylmagnesium iodide in ether (1.51 mL of 3.0M) was added slowly to an ice bath cooled suspension of 7,8,9,10-tetrahydroacephenanthren-7-one (Scott, L. T.; Reinhardt, G.; Roelofs, N. H. *J. Org. Chem.* 1985, 50, 5886) (0.25 g, 1.13 mmol) in ether (10 mL). The bath was removed and the reaction mixture was allowed to warm to room temperature over 1.5 h. The reaction mixture was again cooled to 0° C. and quenched with saturated aqueous ammonium chloride solution. The reaction mixture was concentrated under reduced pressure. The resulting solid was purified via flash chromotography to give 0.17 g (62%) of a crystalline solid: MS (CI) m/e (%) 239 (M+H$^+$, 100); $^1$H NMR (CDCl$_3$, 300 MHz) δ 7.64 (d, 1H, J=8.0 Hz), 7.57 (s, 1H), 7.46 (t, 1H, J=8.4 Hz), 7.28 (d, 1H, J=6.6 Hz), 3.37 (s, 4H), 3.08 (m, 2H), 2.02 (m, 4H), 1.80 (s, 1H), 1.63 (s, 3H).

Part B: 7-Methyl-9,10-dihydroacephenanthrene

A solution of 7-hydroxy-7-methyl-7,8,9,10-tetrahydroacephenanthrene (0.15 g, 0.64 mmol) and camphorsulfonic acid (0.02 g, 0.064 mmol) in toluene (20 mL) was heated at reflux for 1 h. The reaction was allowed to cool and was diluted with ethyl acetate (20 mL). The organic solution was washed with saturated aqueous sodium carbonate solution (3×15 mL) and water (3×15 mL), dried over magnesium sulfate, and concentrated under reduced pressure. The reaction product was purified by flash chromatography to give 0.13 g (92%) of the product: MS (CI) m/e (%) 221 (M+H$^+$, 100); $^1$H NMR (CDCl$_3$, 300 MHz) δ 7.69 (d, 1H, J=8.4 Hz), 7.44 (dd, 1H, J=7.0, 8.4 Hz), 7.32 (s, 1H), 7.21 (d, 1H, J=6.9 Hz), 5.94 (m, 1H), 3.38 (s, 4H), 3.09 (t, 2H, J=8.5 Hz), 2.52 (m, 2H), 2.16 (m, 3H).

Part C: 7-Methylacephenanthrylene

A solution of 7-methyl-9,10-dihydroacephenanthrene (0.13 g, 0.59 mmol) and dichlorodicyanoquinone (0.27 g, 1.18 mmol) in dioxane (10 ml) was heated at reflux for 0.5 h. The reaction mixture was allowed to cool and was diluted with ethyl acetate (50 mL) and water (20 mL). The organic layer was separated, washed with water (3×20 mL) and brine solution (3×20 mL), dried (MgSO$_4$), and concentrated under reduced pressure. The resulting solid was purified by flash chromatography to give 0.07 g (57%) of the product: $^1$H NMR (CDCl$_3$, 300 MHz) δ 8.54 (d, 1H, J=8.0 Hz), 8.40 (dd, 1H, J=7.3, 6.9 Hz), 8.24 (s, 1H), 7.66 (m, 2H), 7.58 (dd, 1H, J=8.4, 7.3 Hz), 7.46 (d, 1H, J=7.3 Hz), 7.20 (d, 1H, J=5.1 Hz), 7.16 (d, 1H, J=5.4 Hz), 2.82 (s, 3H).

Part D: 8-Methylphenanthrene-1,10-dicarboxylic Anhydride

A suspension of 7-methylacephenanthrylene (0.56 g, 2.59 mmol) and sodium dichromate dihydrate (2.70 g, 9.07 mmol) in glacial acetic acid (10 mL) was heated at reflux for 4 h. The reaction mixture was allowed to cool and the resulting solid was collected by suction filtration. The solid was dried to give 0.56 g (80%) of the anhydride: MS (CI) m/e (%) 263 (M+H$^+$, 100); $^1$H NMR (DMSO-d$_6$, 300 MHz) δ 9.55 (d, 1H, J=8.8 Hz), 9.04 (s, 1H), 8.89 (d, 1H, J=8.5 Hz), 8.55 (d, 1H, J=7.4 Hz), 7.75 (d, 1H, J=7.3 Hz), 2.87 (s, 3H).

Part E:
4-[3-(8-Methylphenanthrene-1,10-dicarboximido)-propylamino]-1-(8-methylphenanthrene-1,10-dicarboximido)butane Hydromethanesulfonate 8-Methylphenanthrene-1,10-dicarboxylic anhydride was condensed with spermidine to give the free base: MS (CI) m/e (%) 634 (M+H$^+$, 100); $^1$H NMR (TFA-d, 300 MHz) δ 9.06 (m, 4H), 8.56 (m, 3H), 8.44 (m, 1H), 7.71 (m, 7H), 7.30 (m, 1H), 4.45 (m, 4H), 3.45 (m, 4H), 2.76 (s, 3H), 2.74 (s, 3H), 2.51 (m, 2H), 2.11 (m, 4H). The free base was converted to the mono-methanesulfonate salt: mp 273°-275° C.; MS (CI) m/e (%) 634 (M+H$^+$, 100); $^1$H NMR (TFA-d, 300 MHz) δ 9.31 (s, 1H), 9.19 (s, 1H), 9.12 (d, 1H, J=8.4 Hz), 9.03 (d, 1H, J=8.4 Hz), 8.66 (m, 3H), 8.53 (d, 1H, J=8.0 Hz), 7.91 (m, 4H), 7.70 (d, 1H, J=7.3 Hz), 7.62 (d, 1H, J=7.3 Hz), 7.38 (br s, 2H), 4.61 (m, 2H), 4.49 (m, 2H), 3.55 (m, 4H), 3.20 (s, 3H), 2.84 (s, 3H), 2.83 (s, 3H), 2.59 (m, 2H), 2.20 (m, 4H).

Example 43

Part A: 9-Methylphenanthrene-1,10-dicarboxylic Anhydride

As described in example 14, the following compounds were prepared from dimethyl homophthalate and acetophenone:

Methyl α-(1-phenylethylidene)-(2-carboxyphenyl)acetate: $^1$H NMR (300 MHz, CDCl$_3$) mixture of E/Z isomers δ 11.30 (1H, br s), 8.22+8.03 (1H, d), 7.80–6.80 (8H, m), 3.74+3.46 (3H, s), 2.70+1.95 (3H, s); MS (CH$_4$ CI) m/e 265 (M+H—MeOH), 279 (M+H—H$_2$O), 293 (M+C$_2$H$_5$—MeOH), 297 (M+H), 305 (M+C$_3$H$_5$—MeOH), 325 (M+C$_2$H$_5$).

9-Methylphenanthrene-1,10-dicarboxylic anhydride: $^1$H NMR (300 MHz, CDCl$_3$) δ 9.03 (1H, d), 8.76 (1H, d), 8.64 (1H, d), 8.50 (1H, d), 7.88 (3H, m), 3.35 (3H, s); MS (CH$_4$ CI) m/e 263 (M+H), 291 (M+C$_2$H$_5$), 303 (M+C$_3$H$_5$).

Part B:

4-[3-(9-Methylphenanthrene-1,10-dicarboximido)-propylamino]-1-(9-methylphenanthrene-1,10-dicarboximido)butane Hydromethanesulfonate 9-Methylphenanthrene-1,10-dicarboxylic anhydride was condensed with spermidine and the free base was converted directly to the monomethanesulfonate salt: mp 271°–274° C. (dec).

Example 44

Part A:

6-(Trifluoromethyl)phenanthrene-1,10-dicarboxylic Anhydride

As described in example 14, the following compounds were prepared from dimethyl homophthalate and p-(trifluoromethyl)benzaldehyde:

Methyl α-([4-(trifluoromethyl)phenyl]methylene)-(2-carboxyphenyl)acetate: $^1$H NMR (300 MHz, CDCl$_3$) δ 8.24 (1H, m), 7.83 (1H, s), 7.51 (2H, m), 7.40 (2H, d), 7.08 (3H, m), 3.76 (3H, s); MS (CH$_4$ CI) m/e 319 (M+H—MeOH), 331, 333 (M+H—H$_2$O), 347 (M+C$_2$H$_5$—MeOH), 351 (M+H), 359 (M+C$_3$H$_5$—MeOH), 379 (M+C$_2$H$_5$).

6-(Trifluoromethyl)phenanthrene-1,10-dicarboxylic anhydride: $^1$H NMR (300 MHz, CDCl$_3$) δ 9.13 (1H, d), 9.08 (1H, s), 9.04 (1H, s), 8.76 (1H, d), 8.34 (1H, d), 8.08 (2H, overlapping t and d) ; MS (CH$_4$ CI) m/e 317 (M+H), 345 (M+C$_2$H$_5$), 357 (M+C$_3$H$_5$).

Part B:

4-(3-[6-(Trifluoromethyl)phenanthrene-1,10-dicarbox-imido)propylamino)-1-[6-(trifluoromethyl)phenanthrene-1,10-dicarboximido]butane Hydromethanesulfonate 6-(Trifluoromethyl)phenanthrene-1,10-dicarboxylic anhydride was condensed with spermidine and the free base was converted directly to the monomethanesulfonate salt: mp 310°–312° C.

Example 45

Part A:

9-(Trifluoromethyl)phenanthrene-1,10-dicarboxylic Anhydride

As described in example 14, the following compounds were prepared from dimethyl homophthalate and 2,2,2-trifluoroacetophenone:

Methyl α-(1-phenyl-2,2,2-trifluoroethylidene)-(2-carboxyphenyl)acetate: $^1$H NMR (300 MHz, CDCl$_3$) mixture of E/Z isomers δ 8.23+8.14 (1H, d), 7.90–7.20 (8H, m), 3.83+3.37 (3H, s); MS (CH$_4$ CI) m/e 301, 331 (M+H—HF), 351 (M+H), 359 (M+C$_2$H$_5$—HF), 371 (M+C$_3$H$_5$—HF), 379 (M+C$_2$H$_5$).

9-(Trifluoromethyl)phenanthrene-1,10-dicarboxylic anhydride: $^1$H NMR (300 MHz, CDCl$_3$) δ 9.10 (1H, d), 8.83 (1H, d), 8.72 (1H, d), 8.53 (1H, br d), 8.07 (1H, t), 7.97 (1H, t), 7.87 (1H, t).

Part B:

4-(3-[9-(Trifluoromethyl)phenanthrene-1,10-dicarbox-imido]propylamino)-1-[9-(trifluoromethyl)phenanthrene-1,10-dicarboximido]butane Hydromethanesulfonate 9-(Trifluoromethyl)phenanthrene-1,10-dicarboxylic anhydride was condensed with spermidine and the free base was converted directly to the monomethanesulfonate salt: mp 235°–237° C.

Example 46

Part A: 6,9-Dimethylphenanthrene-1,10-dicarboxylic Anhydride

As described in example 14, the following compounds were prepared from dimethyl homophthalate and 4'-methylacetophenone:

Methyl α-[1-(4-methylphenyl)ethylidene]-(2-carboxyphenyl)acetate: $^1$H NMR (300 MHz, CDCl$_3$) mixture of E/Z isomers δ 8.16+7.99 (1H, d), 7.70–6.80 (7H, m), 3.67+3.43 (3H, s), 2.63+2.38 (3H, s), 2.20+1.88 (3H, s); MS (CH$_4$ CI) m/e 279 (M+H—MeOH), 307 (M+C$_2$H$_5$—MeOH), 311 (M+H), 319 (M+C$_3$H$_5$—MeOH), 339 (M+C$_2$H$_5$).

6, 9-Dimethylphenanthrene-1,10-dicarboxylic anhydride: $^1$H NMR (300 MHz, CDCl$_3$) δ 9.02 (1H, d), 8.63 (1H, d), 8.54 (1H, s), 8.39 (1H, d), 7.86 (1H, t), 7.65 (1H, d), 3.33 (3H, s), 2.71 (3H, s); MS (CH$_4$ CI) m/e 277 (M+H), 305 (M+C$_2$H$_5$), 317 (M+C$_3$H$_5$).

Part B:

4-[3-(6,9-Dimethylphenanthrene-1,10-dicarboximido)-propylamino]-1-(6,9-dimethylphenanthrene-1,10-dicarboximido)butane Hydromethanesulfonate 6,9-Dimethylphenanthrene-1,10-dicarboxylic anhydride was condensed with spermidine and the free base was converted directly to the monomethanesulfonate salt: mp 219°–222° C. (dec).

Example 47

Part A: 6-Ethylphenanthrene-1,10-dicarboxylic Anhydride

As described in example 14, the following compounds were prepared from dimethyl homophthalate and 4-ethylbenzaldehyde:

Methyl α-[(4-ethylphenyl)methylene]-(2-carboxyphenyl)acetate: $^1$H NMR (300 MHz, CDCl$_3$) δ 8.22 (1H, d), 7.81 (1H, s), 7.48 (2H, m), 7.17 (1H, d), 3.73 (3H, s), 2.55 (2H, q), 1.15 (3H, t); MS (CH$_4$ CI) m/e 279 (M+H—MeOH), 293 (M+H—H$_2$O), 307 (M+C$_2$H$_5$—MeOH), 311 (M+H), 319 (M+C$_3$H$_5$—MeOH), 339 (M+C$_2$H$_5$).

6-Ethylphenanthrene-1,10-dicarboxylic anhydride: $^1$H NMR (300 MHz, CDCl$_3$) δ 9.06 (1H, d), 8.96 (1H, s), 8.65 (1H, d), 8.54 (1H, s), 8.08 (1H, d), 7.93 (1H, t), 7.67 (1H, d), 3.01 (2H, q), 1.44 (3H, t).

Part B:
4-[3-(6-Ethylphenanthrene-1,10-dicarboximido)-propylamino]-1-(6-ethylphenanthrene-1,10-dicarboximido)butane Hydromethanesulfonate 6-Ethylphenanthrene-1,10-dicarboxylic anhydride was condensed with spermidine and the free base was converted directly to the monomethanesulfonate salt: mp 197°–199° C.

Example 48
Part A: 9-Phenylphenanthrene-1,10-dicarboxylic Anhydride

As described in example 14, the following compounds were prepared from dimethyl homophthalate and benzophenone:

Methyl α-(diphenylmethylene)-(2-carboxyphenyl)acetate: $^1$H NMR (300 MHz, CDCl$_3$) δ 8.00 (1H, d), 7.40–7.20 (7H, m), 7.14 (1H, d), 7.05 (3H, m), 6.92 (2H, m), 3.43 (3H, s); MS (NH$_3$ CI) m/e 359 (M+H), 376 (M+NH$_4$).

9-Phenylphenanthrene-1,10-dicarboxylic anhydride: $^1$H NMR (300 MHz, CDCl$_3$) δ 9.14 (1H, d), 8.83 (1H, d), 7.97 (1H, t), 7.92 (1H, m), 7.70–7.50 (6H, m), 7.28 (2H, m); MS (CH$_4$ CI) m/e 325 (M+H), 353 (M+C$_2$H$_5$), 365 (M+C$_3$H$_5$); HRMS Calculated for C$_{22}$H$_{12}$O$_3$: 324.0787. Found: 324.0785.

Part B:
4-[3-(9-Phenylphenanthrene-1,10-dicarboximido)-propylamino]-1-(9-phenylphenanthrene-1,10-dicarboximido)butane Hydromethanesulfonate 9-Phenylphenanthrene-1,10-dicarboxylic anhydride was condensed with spermidine and the free base was converted directly to the monomethanesulfonate salt: mp 158°–161° C.

Example 49
Part A: 6-Cyanophenanthrene-1,10-dicarboxylic Anhydride

As described in example 14, the following compounds were prepared from dimethyl homophthalate and 4-cyanobenzaldehyde:

Methyl α-[(4-cyanophenyl)methylene]-(2-carboxyphenyl)acetate: $^1$H NMR (300 MHz, CDCl$_3$) mixture of E/Z isomers δ 8.20 (1H, m), 7.80 (1H, s), 7.50 (2H, m), 7.40 (2H, d), 7.05 (3H, m), 3.72 (3H, s); MS (CH$_4$ CI) m/e 276 (M+H—MeOH), 290 (M+H—H$_2$O), 308 (M+H), 336 (M+C$_2$H$_5$), 348 (M+C$_3$H$_5$).

6-Cyanophenanthrene-1,10-dicarboxylic anhydride: $^1$H NMR (300 MHz, CDCl$_3$) δ 9.09 (1H, d), 9.05 (1H, s), 8.78 (1H, d), 8.31 (1H, d), 8.09 (1H, t), 8.01 (1H, d).

Part B:
4-[3-(6-Cyanophenanthrene-1,10-dicarboximido)-propylamino]-1-(6-cyanophenanthrene-1,10-dicarboximido)butane Hydromethanesulfonate 6-Cyanophenanthrene-1,10-dicarboxylic anhydride was condensed with spermidine and the free base was converted directly to the monomethane sulfonate salt: mp >320° C.; $^1$H NMR (300 MHz, TFA-d) δ 9.31 (2H, d, J=4.7 Hz), 9.23 (2H, d, J=8.1 Hz), 9.21 (2H, s), 8.84 (2H, d, J=7.4 Hz), 8.43 (2H, dd, J=8.2, 4.0 Hz), 8.18–8.07 (4H, m), 7.28 (1H, m), 4.60–4.56 (2H, m), 4.55–4.50 (2H, m), 3.55–3.43 (4H, m), 3.13 (3H, s), 2.56–2.48 (2H, m), 2.21–2.10 (4H, m); MS (NH$_3$ CI) m/e 656 (M+H); IR (KBr) 3500 br, 2229, 1702, 1660, 1618, 1599, 1362, 1208, 784 cm$^{-1}$.

Example 50
Part A: Methyl α-[(2-Bromophenyl)methylene]-(2-carboxy-4-nitrophenyl)acetate Dimethyl 4-nitrohomophthalate (Ghosh, C. K.; Mukherjee, K. K. *J. Ind. Chem. Soc.* 1976, 53, 662) (5 g, 0.02 tool) in THF (20 mL) was added to a suspension of sodium hydride (0.85 g of 60% disp., 0.021 mol) in THF (30 mL) with stirring at 0° C. under nitrogen. The resulting solution was stirred for 5–10 min and 2-bromobenzaldehyde (2.3 mL, 0.02 mol) was added in one portion. The cooling bath was removed after 10 min and the reaction was stirred at room temperature until the mixture solidified. The solid was dissolved in water and extracted with dichloromethane (2×). The aqueous phase was acidified and reextracted 3× with fresh portions of dichloromethane. The latter extracts were combined, washed with water and brine, dried over anhydrous magnesium sulfate, filtered, and evaporated. The residue crystallized on standing to give 5.62 g (70%) of off-white product: $^1$H NMR (300 MHz, CDCl$_3$) δ 3.90 (3H, s), 6.66 (1H, d), 7.09 (1H, t), 7.16–7.23 (3H, m), 7.69 (1H, d), 7.86 (1H, s), 8.24 (1H, dd), 8.68 (1H, d); MS m/e 423–425 (M+NH$_4$$^+$).

Part B: Methyl α-[(2-Bromophenyl)methylene]-(2-methoxycarbonyl-4-nitrophenyl)acetate A solution of methyl α-[(2-bromophenyl)methylene]-(2-carboxy-4-nitrophenyl)acetate (5 g, 0.012 mol) in 2:1 THF/ether (150 mL) was treated at 0° C. with an ethereal solution of 2 equivalents of diazomethane. After 1 h, excess diazomethane was quenched by dropwise addition of glacial acetic acid. The resulting solution was washed with saturated sodium bicarbonate solution and brine, dried over anhydrous magnesium sulfate, filtered, and evaporated. The diester was chromatographed on silica gel (hexane/ethyl acetate 9:1) to give the pure product as a colorless syrup in 82% yield: IR (KBr) 1730, 1526, 1348, 1260 (br) cm$^{-1}$; $^1$H NMR (300 MHz, CDCl$_3$) δ 3.78 (3H, s), 3.94 (3H, s), 6.63 (1H, d), 6.95 (1H, t), 7.07 (1H, t), 7.14 (1H, t), 7.58 (1H, d), 8.03 (1H, s), 8.14 (1H, dd), 8.88 (1H, m); MS m/e 437–439 (M+NH$_4$$^+$), 420–422 (M+H$^+$).

Part C: 1,10-Di(methoxycarbonyl)-3-nitrophenanthrene

A mixture of methyl α-[(2-bromophenyl)methylene]-(2-methoxycarbonyl-4-nitrophenyl)acetate (1.2 g, 2.8 mmol), sodium bicarbonate (0.5 g, 6.1 mmol), and bis (triphenylphosphine) palladium diacetate (0.22 g, 0.5 mmol) in dry DMF (12 mL) was heated for 36 h in an 80° C. oil bath with stirring under nitrogen. The reaction was cooled to room temperature and poured into a mixture of brine and ethyl acetate. The phases were separated and the aqueous layer was extracted with ethyl acetate (2×). The combined extracts were washed with 1M hydrochloric acid (2×), water, and brine, dried over anhydrous magnesium sulfate, filtered, and evaporated. The residue was recrystallized from hot ethyl acetate to give the cyclized product (0.43 g, 45%): IR (KBr) 1735, 1712, 1515, 1345 cm$^{-1}$; $^1$H NMR (300 MHz, CDCl$_3$) δ 3.96 (3H, s), 3.98 (3H, s), 7.79 (1H, t), 7.90 (1H, t), 8.05 (1H, d), 8.53 (1H, s), 8.76 (1H, d), 8.84 (1H, d), 9.74 (1H, d); MS m/e 357 (M+NH$_4$+). Unreacted starting material could be recovered from the mother liquor.

Part D: 3-Nitrophenanthrene-1,10-dicarboxylic Anhydride

A suspension of 1,10-di(methoxycarbonyl)-3-nitrophenanthrene in THF (25 mL) and 1M lithium hydroxide (10 mL) was heated at reflux overnight. The reaction was cooled to room temperature, poured into water, and extracted with dichloromethane (2×). The aqueous phase was acidified to pH 2 with 1M hydrochloric acid. The resulting solid was collected by filtration, washed with dichloromethane and water, and dried to give the product as a mixture of diacid and anhydride (0.2 g, 73%): IR (KBr) 1783, 1741, 1704, 1520, 1345 cm$^{-1}$; MS m/e 311 (M+NH$_4$+), 281 (M+NH$_4$+—NO), 264 (M+H+—NO).

The crude diacid (150 mg, 4.8 mmol) was heated for 6 h in a mixture of glacial acetic acid (0.9 mL), acetic anhydride (0.1 mL), and dioxane (1 mL). The mixture was cooled to room temperature and filtered. The solid was washed with hexane and dried under vacuum to give the anhydride as a light yellow solid (0.13 g, 91%): IR (KBr) 1784, 1741, 1518, 1345 cm$^{-1}$; $^1$H NMR (300MHz, CDCl$_3$) δ 7.98 (1H, t), 8.09 (1H, t), 8.53 (1H, d), 9.02 (1H, d), 9.24 (1H, d), 9.29 (1H, s), 10.03 (1H, d); MS m/e 311 (M+NH$_4$+), 281 (M+NH$_4$+—NO).

Part E: 4-[3-(3-Nitrophenanthrene-1,10-dicarboximido)-propylamino]-1-(3-nitrophenanthrene-1,10-dicarboximido)butane Hydromethanesulfonate 3-Nitrophenanthrene-1,10-dicarboxylic anhydride was condensed with spermidine and the free base was converted directly to the monomethanesulfonate salt: mp >240° C. (dec); IR (KBr) 3450, 1708, 1663 cm$^{-1}$; $^1$H NMR (300 MHz, TFA-d) δ 2.16 (4H, m), 2.52 (2H, m), 3.14 (3H, s), 3.48 (6H, m), 4.53 (4H, m), 7.96 (2H, m), 8.13 (2H, m), 8.30 (2H, m), 8.93 (2H, m), 9.32 (2H, m), 9.45 (2H, m), 10.05 (2H, m); MS m/e 696 (M+H+), 666 (M+H+—NO).

Example 51
Part A: 5-Nitrophenanthrene-1,10-dicarboxylic Anhydride

As described in example 50, the following compounds were prepared from dimethyl homophthalate and 2-bromo-3-nitrobenzaldehyde (Rahman, L. K. A.; Scrowston, R. M. *J. Chem. Soc. Perkin Trans.* 1 1984, 385):
Methyl α-[(2-bromo-3-nitrophenyl) methylene]-(2-carboxyphenyl)acetate: mp 164°–166° C.
Methyl α-[(2-bromo-3-nitrophenyl)methylene]-(2-methoxycarbonylphenyl)acetate: mp 165° C.
1,10-Di(methoxycarbonyl)-5-nitrophenanthrene: mp 184°–185° C.
5-Nitrophenanthrene-1,10-dicarboxylic anhydride: mp 246° C.; $^1$H NMR (300 MHz, TFA-d) δ 9.24 (1H, s), 8.83 (1H, d, J=7.7 Hz ), 8.67 (1H, d, J=8.8 Hz), 8.47 (1H, d, J=8.1 Hz ), 8.16 (1H, d, J=7.7 Hz), 8.00 (1H, t J=7.7 Hz ), 7.95 (1H, t, J=8.1 Hz); MS (NH$_3$, CI) 311 (M+NH$_4$), 281 (M+NH$_4$—NO); IR (KBr) 1783, 1746, 1521, 1376, 1153, 1071,1040, 775 cm$^{-1}$.

Part B: 4-[3-(5-Nitrophenanthrene-1,10-dicarboximido)-propylamino]-1-(5-nitrophenanthrene-1,10-dicarboximido)butane Hydromethanesulfonate 5-Nitrophenanthrene-1,10-dicarboxylic anhydride was condensed with spermidine and the free base was converted directly to the monomethanesulfonate salt (75%): mp 292° C. (dec); $^1$H NMR (300 MHz, DMSO-d$_6$) δ 9.12 (2H, s), 8.73 (2H, d, J=8.0 Hz), 8.61 (2H, d, J=7.5 Hz ), 8.38–8.34 (4H, m), 8.25 (1H, m), 8.03–7.98 (4H, m) 4.20 (4H, m), 3.22–3.00 (2H, m), 3.00–2.90 (2H, m), 2.30 (3H, s), 2.10–1.98 (2H, m), 1.80–1.60 (4H, m); IR (KBr) 3500–3400 (br), 3000–2700 (br), 1705, 1661, 1528, 1367, 1205, 780 cm$^{-1}$.

Example 52
Part A: 6-Nitrophenanthrene-1,10-dicarboxylic Anhydride

As described in example 50, the following compounds were prepared from dimethyl homophthalate and 2-bromo-4-nitrobenzaldehyde (Dandegaonker, S. H. *J. Ind. Chem. Soc.* 1969, 46, 148):
Methyl α-[(2-bromo-4-nitrophenyl)methylene]-(2-carboxyphenyl)acetate: mp 125°–128° C.
Methyl α-[(2-bromo-4-nitrophenyl)methylene]-(2-methoxycarbonylphenyl)acetate: mp 111°–113° C.
1,10-Di(methoxycarbonyl)-6-nitrophenanthrene: mp 184°–186° C.
6-Nitrophenanthrene-1,10-dicarboxylic anhydride: mp 290° C.; $^1$H NMR (300 MHz, DMSO-d$_6$) δ 9.79 (1H, d, J=1.8 Hz), 9.56 (1H, d, J=7.7 Hz), 9.20 (1H, s), 8.70 (1H, d, J=9.1 Hz), 8.63 (1H, d, J=7.4 Hz), 8.60 (1H, dd, J=8.8, 1.8 Hz), 8.12 (1H, t, J=7.7 Hz); MS (NH$_3$ CI) m/e 311 (M+NH$_4$), 264 (M+H—NO), 281 (M+NH$_4$—NO); IR (KBr) 1783, 1742, 1600, 1547, 1514, 1350 cm$^{-1}$.

Part B: (S,S)-1,2-bis-[2-(6-Nitrophenanthrene-1,10-dicarboximido)propylamino]ethane Dihydromethanesulfonate 6-Nitrophenanthrene-1,10-dicarboxylic anhydride was condensed with (S,S)-1,2-bis-(2-aminopropylamino)ethane (U.S. patent application Ser. No. 92/02134. ) The crude material was purified by flash chromatography on silica gel with 0.2% triethylamine, 5% methanol in dichloromethane. The material isolated from the column was dissolved in hot dichloromethane, treated with charcoal, and filtered through celite. The filtrate was diluted with diethyl ether to precipitate the free base: mp 112°–115° C. The free base was treated with methanesulfonic acid (2.1 equivalents) in dichloromethane to give the di-methanesulfonate salt (58%): mp 253°–255° C.; MS (NH$_3$ CI) m/e 725 (M+H), 707 (M+H—H$_2$O); IR (KBr) 3400–3300 (br), 3000–2500 (br), 1706, 1663, 1600, 1545, 1512, 1348, 1207, 784 cm$^{-1}$;

Elemental Analysis: Calculated for $C_{42}H_{40}N_6O_{14}S_2$: C, 55.02; H, 4.40; N, 9.17. Found: C, 55.40; H, 4.38; N, 9.07.

Example 53

Part A: Dimethyl 4-Acetamidohomophthalate

Dimethyl 4-acetamidohomophthalate was prepared from dimethyl 4-nitrohomophthalate by reduction and acetylation using standard procedures: $^1$H NMR (300 MHz, CDCl$_3$) δ 2.15 (s, 3H), 3.70 (s, 3H), 3.85 (s, 3H), 3.95 (s, 2H), 7.15 (d, 1H, J=8.0 Hz), 7.50 (br s, 1H), 7.70 (dd, 1H, J=8.0, 2.2 Hz), 7.99 (d, 1H, J=2.2 Hz); MS m/e 266 (M+H$^+$).

Part B: 3-Acetamidophenanthrene-1,10-dicarboxylic Anhydride

As described in example 50, the following compounds were prepared from dimethyl 4-acetamidohomophthalate and 2-bromobenzaldehyde:

Methyl α-[(2-bromophenyl)methylene]-(2-carboxy-4-acetamidophenyl)acetate: $^1$H NMR (300 MHz, DMSO-d$_6$) δ 2.05 (3H, s), 3.63 (3H, s), 6.68 (1H, d), 6.80 (1H, d, J=8 Hz), 7.04–7.20 (2H, m), 7.52–7.59 (1H, m), 7.65 (1H, d, J=8 Hz), 7.70 (1H, s), 8.25 (1H, d, J=2 Hz), 10.15 (1H, s), 13.10 (1H, br s).

Methyl α-[(2-bromophenyl)methylene]-(2-methoxycarbonyl-4-acetamidophenyl)acetate: $^1$H NMR (300 MHz, CDCl$_3$) δ 2.17 (3H, s), 3.77 (3H, s), 3.86 (3H, s), 6.68–6.71 (1H, m), 6.89–6.92 (2H, m), 6.94–6.99 (1H, m), 7.23–7.25 (1H, m), 7.53–7.58 (2H, m), 7.92 (1H, s), 8.11 (1H, s); MS m/e 434 (M+H$^+$).

3-Acetamidophenanthrene-1,10-dicarboxylic Anhydride

Methyl α-[(2-bromophenyl)methylene]-(2-methoxycarbonyl-4-acetamidophenyl)acetate was cyclized and converted directly to the anhydride without isolation of the diester intermediate: $^1$H NMR (300 MHz, DMSO-d$_6$) δ 2.20 (3H, s), 7.87 (1H, t), 8.01 (1H, t), 8.41 (1H, d), 8.68 (1H, d), 8.75 (1H, s), 8.95 (1H, s), 9.45 (1H, s), 10.70 (1H, s); MS m/e 323 (M+NH$_4^+$).

Part C: 3-Aminophenanthrene-1,10-dicarboxylic Anhydride

3-Acetamidophenanthrene-1,10-dicarboxylic anhydride was hydrolyzed under standard conditions to give the amine: $^1$H NMR (300 MHz, DMSO-d$_6$) δ 7.78 (1H, t), 7.90 (2H, s), 8.25 (2H, s), 8.30 (1H, d), 8.63 (1H, d), 8.65 (1H, s).

Part D: 4-[3-(3-Aminophenanthrene-1,10-dicarboximido)-propylamino]-1-(3-aminophenanthrene-1,10-dicarboximido)butane Trihydromethanesulfonate 3-Aminophenanthrene-1,10-dicarboxylic anhydride was condensed with spermidine to give the free base: $^1$H NMR (300 MHz, DMSO-d$_6$) δ 1.40–1.55 (2H, m), 1.60–1.75 (2H, m), 1.75–1.82 (2H, m), 2.55–2.70 (4H, m), 4.00–4.20 (4H, m), 6.10 (4H, s), 7.70–7.80 (2H, m), 7.80–7.90 (2H, m), 8.15 (2H, s), 8.25 (2H, d), 8.55–8.65 (2H, d and 4H, s). The free base was treated with methanesulfonic acid. (3.5 equivalents) to give the trimethanesulfonate salt: mp 280° C. (dec).

Example 54

Part A: 7-Methoxyphenanthrene-1,10-dicarboxylic Anhydride

As described in example 50, the following compounds were prepared from dimethyl homophthalate and 2-bromo-5-methoxybenzaldehyde (Handford, B. O.; Whalley, W. B. J. Chem. Soc. 1963, 3896):

Methyl α-[(2-bromo-5-methoxyphenyl)methylene]-(2-carboxyphenyl)acetate: mp 51°–53° C.

Methyl α-[(2-bromo-5-methoxyphenyl)methylene]-(2-methoxycarbonylphenyl)acetate: mp 75°–77° C.

1,10-Di(methoxycarbonyl)-7-methoxyphenanthrene: mp 148°–149° C.

7-Methoxyphenanthrene-1,10-dicarboxylic anhydride: mp 292°–293° C.; $^1$H NMR (300MHz, TFA-d) δ 9.18–9.15 (2H, d+s), 8.83 (1H, d), 8.74 (1H, d), 8.04 (1H, t), 7.75–7.73 (2H, d+s), 4.20 (3H, s); MS (NH$_3$ CI) 279 (M+H), 296 (M+NH$_4$); IR (KBr) 1775, 1734, 1599, 1290, 720 cm$^{-1}$.

Part B: 4-[3-(7-Methoxyphenanthrene-1,10-dicarboximido)-propylamino]-1-(7-methoxyphenanthrene-1,10-dicarboximido)butane Hydromethanesulfonate 7-Methoxyphenanthrene-1,10-dicarboxylic anhydride was condensed with spermidine and the free base was converted directly to the monomethanesulfonate salt (77%): mp 162°–165° C.; $^1$H NMR (300 MHz, DMSO-d$_6$) δ 9.18 (2H, d, J=8.4 Hz), 8.93 (2H, d, J=2.2 Hz), 8.90 (2H, d, J=9.2 Hz), 8.45 (2H, d, J=7.3 Hz), 7.94 (2H, dd, J=8.1, 8 Hz), 7.90 (2H, t, J=2.6 Hz), 7.59–7.55 (2H, dd, J=9.2, 2.6 Hz), 4.17–4.12 (4H, m), 3.97 (6H, s), 3.04–2.96 (4H, m), 2.29 (3H, s), 2.08–1.99 (2H, m), 1.75–1.65 (4H, m); IR (KBr) 3500 (br), 3100 (br), 1699, 1657, 1617, 1599, 1355, 1230, 1209, 780 cm$^{-1}$.

Example 55

Part A: 6,7-Dimethoxyphenanthrene-1,10-dicarboxylic Anhydride

As described in example 50, the following compounds were prepared from dimethyl homophthalate and 6-bromoveratraldehyde (Raiford, L.; Perry, R. P. J. Org. Chem. 1942, 7, 354):

Methyl α-[(2-bromo-4,5-dimethoxyphenyl)methylene]-(2-carboxyphenyl)acetate: mp 129°–130° C.; $^1$H NMR (300 MHz, CDCl$_3$) δ 8.15 (1H, dd, J=7..5, 1.4 Hz), 7.98 (1H, s), 7.47–7.39 (2H, d+t), 7.09 (1H, dd, J=7.3, 1.4 Hz), 6.99 (1H, s), 6.14 (1H, s), 3.83 (3H, s), 3.78 (3H, s), 3.21 (3H, s); MS (NH3 CI) m/e 440 (M+NH$_4$), 423 (M+H); IR (KBr) 3400–3300 (br), 1720, 1695, 1510, 1281, 1220 cm$^{-1}$.

Methyl α-[(2-bromo-4,5-dimethoxyphenyl)methylene]-(2-methoxycarbonylphenyl)acetate: mp 117°–119° C.; $^1$H NMR (300 MHz, CDCl$_3$) δ 8.07 (1H, dd, J=7.2, 2.2 Hz), 7.97 (1H, s), 7.46–7.36 (2H, m), 7.08 (1H, dd, J=7.1, 2.2 Hz), 6.99 (1H, s), 6.14 (1H, s), 3.86 (3H, s), 3.83 (3H, s), 3.78 (3H, s), 3.19 (3H, s); MS (NH$_3$ CI) m/e 454 (M+NH$_4$), 406 (M+H—OMe); IR (KBr) 1725, 1712, 1510, 1440, 1282, 1250, 1220, 1169 cm$^{-1}$.

1,10-Di(methoxycarbonyl)-6,7-dimethoxyphenanthrene: mp 192°–193° C.; $^1$H NMR (300 MHz, CDCl$_3$) δ 8.70 (1H, d, J=8.8 Hz), 8.28 (1H, s), 8.01 (1H, d, J=7.3 Hz), 7.96 (1H, s), 7.69 (1H, t, J=7.3 Hz), 7.30 (1H, s), 4.14 (3H, s), 4.05 (3H, s), 3.93 (3H, s); MS (CH$_4$ CI) m/e 355 (M+H), 323 (M+H—MeOH).

6,7-Dimethoxyphenanthrene-1,10-dicarboxylic anhydride: mp >324° C.; $^1$H NMR (300 MHz, TFA-d) δ 9.10 (2H, s+d, J=7.7 Hz), 8.72 (1H, d, J=7.3 Hz), 8.25 (1H, s), 8.00 (1H, t, J=7.7 Hz), 7.67 (1H, s), 4.25 (3H, s), 4.18 (3H, s) ; MS (NH$_3$ CI) m/e 309 (M+H), 326 (M+NH4); IR (KBr) 1761, 1720, 1601, 1525, 1511, 1275, 1265, 1217, 1004, 780 cm$^{-1}$.

Part B:
4-[3-(6,7-Dimethoxyphenanthrene-1,10-dicarboximido)propylamino]-1-(6,7-dimethoxyphenanthrene-1,10-dicarboximido)butane Hydromethanesulfonate 6,7-Dimethoxyphenanthrene-1,10-dicarboxylic anhydride was condensed with spermidine and the free base was converted directly to the monomethanesulfonate salt (59%): mp 254°-257° C.; $^1$H NMR (300 MHz, DMSO-d$_6$) δ 9.27 (2H, d), 8.90 (2H, S), 8.47 (2H, d), 8.31 (2H, s), 7.95 (2H, t), 7.88 (2H, s), 4.20-4.12 (4H, m), 4.11 (6H, s), 3.98 (6H, S), 3.06-2.90 (4H, m), 2.31 (3H, s), 2.08-1.95 (2H, m), 1.78-1.63 (4H, m); IR (KBr) 3600-3300 (br), 2900-3000 (br), 1695, 1653, 1599, 1512, 1420, 1385, 1342, 1265, 1216, 1166, 781 cm$^{-1}$.

Example 56

Part A: 6-Fluorophenanthrene-1,10-dicarboxylic Anhydride

As described in example 14, the following compounds were prepared from dimethyl homophthalate and 4-fluorobenzaldehyde:

Methyl α-[(4-fluorophenyl)methylene]-(2-carboxyphenyl)acetate: $^1$H NMR (300 MHz, CDCl$_3$) δ 8.23 (1H, m), 7.78 (1H, s), 7.50 (2H, m), 7.13 (1H, m), 6.93 (2H, dd), 6.82 (2H, t), 3.72 (3H, s); MS (CH$_4$ CI) m/e 269 (M+H—MeOH), 283 (M+H—H$_2$O), 297 (M+C$_2$H$_5$—MeOH), 300, 301 (M+H), 309 (M+C$_3$H$_5$—MeOH), 329 (M+C$_2$H$_5$).

6-Fluorophenanthrene-1,10-dicarboxylic anhydride: $^1$H NMR (300 MHz, CD$_3$COCD$_3$) δ 9.34 (1H, dd), 9.09 (1H, s), 8.76 (1H, dd), 8.67 (1H, dd), 8.54 (1H, dd), 8.15 (1H, dd), 7.76 (1H, td); MS (CH$_4$ CI) m/e 267 (M+H), 295 (M+C$_2$H$_5$), 307 (M+C$_3$H$_5$); HRMS Calculated for C$_{16}$H$_7$FO$_3$: 266.0379. Found: 266.0380.

Part B:
4-[3-(6-Fluorophenanthrene-1,10-dicarboximido)propylamino]-1-(6-fluorophenanthrene-1,10-dicarboximido)butane Hydromethanesulfonate 6-Fluorophenanthrene-1,10-dicarboxylic anhydride was condensed with spermidine and the free base was converted directly to the monomethanesulfonate salt: mp 300°-306° C. (dec).

Example 80

Part A: Naphtho[1,2-b]furan-5,6-dicarboxylic Anhydride

As described in example 14, the following compounds were prepared from dimethyl homophthalate and 3-furaldehyde:

Methyl α-[(3-furyl) methylene]-(2-carboxyphenyl)acetate: $^1$H NMR (300 MHz, CDCl$_3$) δ 8.19 (1H, d), 7.66 (1H, s), 7.58 (1H, t), 7.50 (1H, t), 7.25 (2H, overlap), 7.11 (1H, s), 5.39 (1H, s), 3.70 (3H, s); MS (CH$_4$ CI) m/e 273 (M+H), 301 (M+C$_2$H$_5$), 313 (M+C$_3$H$_5$).

Naphtho [1,2-b]furan-5,6-dicarboxylic anhydride: $^1$H NMR (300 MHz, CDCl$_3$) δ 8.95 (1H, s), 8.76 (1H, d), 8.66 (1H, d), 7.98 (1H, d), 7.93 (1H, t), 7.16 (1H, d); MS (CH$_4$ CI) m/e 239 (M+H), 267 (M+C$_2$H$_5$), 279 (M+C$_3$H$_5$); HRMS Calculated for C$_{14}$H$_6$O$_4$: 238.0266. Found: 238.0263.

Part B:
4-[3-(Naphtho[1,2-b]furan-5,6-dicarboximido)propylamino]-1-(naphtho[1,2-b]furan-5,6-dicarboximido)butane Hydromethanesulfonate Naphtho[1,2-b]furan-5,6-dicarboxylic anhydride was condensed with spermidine and the free base was converted directly to the mono-methanesulfonate salt: mp 273°-276° C. (dec).

Example 81

Part A:
2-Methyl-1H-naphth[1,2-d]imidazole-5,6-dicarboxylic Anhydride

Concentrated hydrochloric acid (16.9 mL, 203 mmol) was added dropwise to a suspension of 3-nitro-4-acetamido-1,8-naphthalic anhydride (Jones, L. A.; Kim, H. K.; Watson, R. J. Chem. Soc. C 1971, 3891; Mosebach, G.; Sachs, F. Chem. Ber. 1911, 44, 2852) (3.9 g, 13.5 mmol) and stannous chloride dihydrate (15.27 g, 67.7 mmol) in ethanol (25 mL) and the resulting orange suspension was heated at 50° C. for 50 min. The mixture was cooled to .room temperature and poured into water (85 mL). The suspended, brown solid was collected on a frit and washed with 0.1M aqueous sodium hydroxide (3×25 mL) and water (50 mL). The dried solid was heated at reflux in acetic acid (80 mL) for 2 h and the hot suspension was filtered to give a tan solid. This material was suspended in water (50 mL) and the mixture was neutralized with 0.1M aqueous sodium hydroxide. The suspended solid was collected, washed with water (25 mL), and dried to give 2.90 g (85%) of a light orange solid: mp 300° C. (lit. mp 340°-342° C.: Podrezova, T. N. Khim. Geterotsikl. Soedin. 1973, 566; Chem. Abstr. 1973, 79, 31988p); $^1$H NMR (DMSO-d$_6$, 300 MHz) δ 2.69 (s, 3H), 7.95 (dd, 1H, J=8.1, 7.3 Hz), 8.46 (dd, 1H, J=7.3, 1.1 Hz), 8.51 (s, 1H), 8.85 (dd, 1H, J=8.0, 1.1 Hz); MS (CI, CH$_4$) m/e (%) 253 (M+H$^+$, 100).

Part B:
4-[3-(2-Methyl-1H-naphth[1,2-d]imidazole-5,6-dicarboximido)propylamino]-1-(2-methyl-1H-naphth[1,2-d]imidazole-5,6-dicarboximido)butane Trihydromethanesulfonate 2-Methyl-1H-naphth[1,2-d]imidazole-5,6-dicarboxylic anhydride was condensed with spermidine to give the free base, which was converted directly to the trimethanesulfonate salt by treatment with methanesulfonic acid (3.2 equivalents) (28%): mp 260°-261° C. (dec); $^1$H NMR (DMSO-d$_6$, 300 MHz) δ 1.62-1.80 (br m, 4H), 1.98-2.10 (br m, 2H), 2.37 (s, 9H), 2.74 (s, 6H), 2.92-3.09 (br m, 4H), 4.08-4.20 (br m, 4H), 7.98 (t, 2H, J=7.7 Hz), 8.24-8.38 (br m, 2H), 8.50 (d, 2H, J=6.9 Hz), 8.58 (s, 2H), 8.83 (d, 2H, J=8.1 Hz), 12.5 (very broad, 2H); MS (CI, NH$_3$) m/e (%) 614 (M+H$^+$ free base, 17), 361 (8), 323 (30), 309 (30), 284 (24), 267 (50), 252 (100).

Example 82

Part A: 3-Acetamido-4-bromo-1,8-naphthalic Anhydride

Bromine (0.11 mL, 2.20 mmol) was added dropwise to a stirred suspension of 3-acetamido-1,8-naphthalic anhydride (Middleton, R. W.; Parrick, J.; Clarke, E. D.; Wardman, P. J. Heterocyclic Chem. 1986, 23, 849) (255 mg, 1.00 mmol) in glacial acetic acid (60 mL). The reaction mixture was heated at reflux for 4 h then allowed to cool to room temperature. Acetic anhydride (5.0 mL, 53 mmol) and glacial acetic acid (5 mL) were added. The mixture was heated at reflux for an additional 2 h then allowed to cool to room temperature. The precipitated solid was collected by suction filtration and washed successively with glacial acetic acid and hexanes to give 110 mg (33%) of a solid: mp 286°–288° C.; IR (KBr) 3402, 3090, 1776, 1737, 1696, 1620, 1595, 1573, 1504, 1448, 1413, 1389, 1275, 1148, 1015, 784 cm$^{-1}$; $^1$H NMR (300 MHz, DMSO-d$_6$) δ 10.16 (br s, 1H), 8.69 (s, 1H), 8.65 (d, 1H, J=8.4 Hz), 8.54 (d, 1H, J=7.7 Hz), 8.02 (dd, 1H, J=8.4, 7.7 Hz) 2.22 (s, 3H); MS (CI) m/e 334 (M+H), 254 (base).

Part B:
2-Methylnaphtho[2,1-d]thiazole-5,6-dicarboxylic Anhydride

Lawesson's reagent (0.78 g, 1.92 mmol) was added in one portion to a stirred suspension of 3-acetamido-4-bromo-1,8-naphthalic anhydride (1.00 g, 2.99 mmol) in toluene (30 mL). The reaction mixture was heated at reflux for 2.5 h at which time additional Lawesson's reagent (0.12 g, 0.29 mmol) was added. The mixture was heated at reflux for 1 h, allowed to cool to room temperature, and immediately purified using flash chromatography (elution with 9:1 CH$_2$Cl$_2$—MeOH) to give 270 mg (34%) of the solid product: mp 289°–292° C.; IR (KBr) 3073, 2930, 1780, 1737, 1596, 1412, 1302, 1262, 1195, 1166, 1149, 1074, 1050, 1022, 780 cm$^{-1}$; $^1$H NMR (300 MHz, DMSO-d$_6$) δ 8.89 (s, 1H), 8.68 (d, 1H, J=8.4 Hz), 8.56 (d, 1H, J=7.3 Hz), 8.02 (dd, 1H, J=8.4, 7.3 Hz), 2.99 (s, 3H); MS (CI) m/e 287 (M+NH$_4$, base), 270 (M+H).

Part C:
4-[3-(2-Methylnaphtho[2,1-d]thiazole-5,6-dicarboximido)propylamino]-1-(2-methylnaphtho[2,1-d]thiazole-5,6-dicarboximido)butane Hydromethanesulfonate 2-Methylnaphtho[2,1-d]thiazole-5,6-dicarboxylic anhydride was condensed with spermidine to give the free base (92%): mp 275°–278° C.; IR (KBr) 2954, 1695, 1661, 1593, 1434, 1333, 1175, 782 cm$^{-1}$; $^1$H NMR (300 MHz, TFA-d) δ 9.33 (d, 2H, J=11.7 Hz), 8.99 (m, 2H), 8.70 (d, 2H, J=8.5 Hz), 8.24 (m, 2H), 7.30 (br s, 1H), 4.49 (m, 4H), 3.43 (br s, 10H), 2.45 (m, 2H), 2.12 (m, 4H); MS (CI) m/e 648 (M+H, base). The free base was converted to the mono-methanesulfonate salt (93%): mp 318°–321° C. (dec); IR (KBr) 2959, 2782, 1698, 1656, 1613, 1591, 1452, 1433, 1333, 1285, 1208, 1193, 1058, 783 cm$^{-1}$; $^1$H NMR (300 MHz, DMSO-d$_6$) δ 8.79 (s, 2H), 8.52 (m, 4H), 8.26 (br s, 2H), 7.95 (m, 2H), 4.13 (m, 4H), 3.04 (m, 4H), 2.97 (s, 6H), 2.29 (s, 3H), 2.02 (m, 2H), 1.73 (m, 4H); MS (CI) m/e 648 (M+H, base).

Example 83

(R,R)-1,2-bis-[2-(2-Methylnaphtho[2,1-d]thiazole-5,6-dicarboximido)propylamino]ethane Dihydromethanesulfonate 2-Methylnaphtho[2,1-d]thiazole-5,6-dicarboxylic anhydride was condensed with (R,R)-1,2-bis-(2-aminopropylamino) ethane (U.S. patent application Ser. No. 92/02134) to give the free base (50%): mp 238°–241° C.; IR (KBr) 2970, 2931, 1697, 1661, 1615, 1591, 1452, 1421, 1329, 1284, 1237, 1197, 1173, 1078, 782, 750 cm$^{-1}$; $^1$H NMR (300 MHz, TFA-d) δ 9.23 (s, 2H), 8.88 (d, 2H, J=7.7 Hz), 8.64 (d, 2H, J=8.1 Hz), 8.20 (dd, 2H, J=8.1, 7.7 Hz), 5.84 (m, 2H), 4.43 (dd, 2H, J=13.6, 10.2 Hz), 3.88 (m, 4H), 3.60 (m, 2H), 3.41 (s, 6H), 1.76 (d, 6H, J=7.3 Hz); MS (CI) m/e 677 (M+H), 308 (base). The free base was converted to the dimethanesulfonate salt (35% mp >215° C. (dec); IR (KBr) 2934, 2729, 1702, 1661, 1616, 1591, 1452, 1421, 1382, 1329, 1285, 1195, 1058, 784 cm$^{-1}$; $^1$H NMR (300 MHZ, TFA-d) δ 9.24 (S, 2H), 8.88 (d, 2H, J=7.7 Hz), 8.66 (d, 2H, J=8.4 Hz), 8.19 (dd, 2H, J=8.4, 7.7 Hz ), 5.83 (m, 2H), 4.39 (m, 2H), 3.90 (m, 4H), 3.41 (s, 6H), 2.91 (s, 6H), 1.75 (d, 6H, J=6.9 Hz); MS (CI) m/e 677 (M+H), 245 (base).

Example 90

Part A: Naphtho[2,1-b]furan-5,6-dicarboxylic Anhydride

As described in example 14, the following compounds were prepared from dimethyl homophthalate and 2-furaldehyde:
Methyl α-[(2-furyl)methylene]-(2-carboxyphenyl)acetate: $^1$H NMR (300 MHz, CDCl$_3$) δ 8.20 (1H, d), 7.65 (1H, s), 7.60 (1H, t), 7.51 (1H, t), 7.29 (2H, m), 6.24 (1H, m), 5.74 (1H, d), 3.74 (1H, d), 3.74 (3H, s). Naphtho[2,1-b]furan-5,6-dicarboxylic anhydride: $^1$H NMR (300 MHz, CDCl$_3$) δ 8.84 (1H, s), 8.65 (1H, d), 8.59 (1H, d), 8.10 (1H, d), 7.91 (1H, t), 7.45 (1H, d); MS (CH$_4$ CI) m/e 239 (M+H), 267 (M+C$_2$H$_5$), 279 (M+C$_3$H$_5$); HRMS Calculated for C$_{14}$H$_6$O$_4$: 238.0266. Found: 238.0261.

Part B:
4-[3-(Naphtho[2,1-b]furan-5,6-dicarboximido)propylamino]-1-(naphtho[2,1-b]furan-5,6-dicarboximido)butane Hydromethanesulfonate Naphtho[2,1-b]furan-5,6-dicarboxylic anhydride was condensed with spermidine and the free base was converted directly to the mono-methanesulfonate salt: mp 160°–165° C.

Example 100

4-[3-(7,12-Dihydro-7,12-dioxobenz[a]anthracene-4,5-dicarboximido)propylamino]-1-(7,12-dihydro-7,12-dioxobenz[a]anthracene-4,5-dicarboximido)butane Hydromethanesulfonate 7,12-Dihydro-7,12-dioxobenz[a]anthracene-4,5-dicarboxylic anhydride, 33, (Kasai, T.; Ando, H.; Tsuruoka, S. Kogyo Kagaku Zasshi 1968, 71, 1871, Chem. Abstr. 1969, 70, 77657x; Akiyoshi, S.; Tsuge, O. Kogyo Kagaku Zasshi 1956, 59, 455, Chem. Abstr. 1958, 52, 3754b; Peters, A. T.; Rowe, F. M. J. Soc. Dyers Colour. 1943, 59, 52) was condensed with spermidine to give the free base (25%): mp 257°–259° C.; MS m/e 766 (M+H$^+$); $^1$H NMR (TFA-d, 300 MHz) δ 52.35 (br m, 4H), 2.70 (br m, 2H), 3.70 (br m, 4H), 4.50–4.65 (m, 4H), 8.00–8.20 (m, 4H), 8.21 (m, 2H), 8.39–8.60 (m, 4H), 8.91 (d, J=8.1 Hz, 2H), 9.52 (s, 1H), 9.54 (s, 1H), 10.00 (d, J=9.0 Hz, 2H). The free base was converted to the mono-methanesulfonate salt (81%): mp 266°–268° C.; MS m/e 766 (M+H$^+$); $^1$H NMR (TFA-d, 300 MHz) δ 2.35 (br m, 4H), 2.70 (br m, 2H), 3.28 (s, 3H), 3.70 (br m, 4H), 4.50–4.65 (m, 4H), 8.00–8.20 (m, 4H), 8.21 (m, 2H), 8.39–8.60 (m, 4H), 8.91 (d, J=8.1 Hz, 2H), 9.52 (s, 1H), 9.54 (s, 1H), 10.0 (d, J=9.0 Hz, 2H).

Example 101

(R,R)-1,2-bis-[2-(7,12-Dihydro-7,12-dioxobenz[a]anthracene-4,5-dicarboximido)propylamino]ethane Dihydromethanesulfonate 7,12-Dihydro-7,12-dioxobenz[a]anthracene-4,5-dicarboxylic anhydride was condensed with (R,R)-1,2-bis-(2-aminopropylamino) ethane (U.S. patent application Ser. No. 92/092134.) The crude material was purified by flash chromatography on silica gel with 5% methanol in dichloromethane, increasing to 25% methanol in dichloromethane (20%): mp >300° C.; $^1$H NMR (DMSO-d$_6$, 300 MHz) δ 1.60 (d, J=6.6 Hz, 6H), 3.31 (m, 4H), 3.45 (br m, 2H), 3.90 (m, 2H), 5.52 (m, 2H), 8.00 (m, 4H), 8.14 (t, J=7.4 Hz, 2H), 8.25 (m, 4H), 8.66 (d, J=7.2 Hz, 2H), 9.11 (s, 2H), 9.89 (d, J=7.5 Hz, 2H); $[\alpha]_D^{25}$ −16.35° (c=0.104 g/dL, DMSO). The free base was converted to the di-methanesulfonate salt (60%): mp 208°-210° C.; MS m/e 795 (M+H$^+$); $^1$H NMR (DMSO-d$_6$, 300 MHz) δ 1.60 (d, J=6.6 Hz, 6H), 2.28 (s, 6H), 3.31 (m, 4H), 3.45 (br m, 2H), 3.90 (m, 2H), 5.52 (m, 2H), 8.00 (m, 4H), 8.14 (t, J=7.4 Hz, 2H), 8.25 (m, 4H), 8.66 (d, J=7.2 Hz, 2H), 9.11 (s, 2H), 9.89 (d, J=7.5 Hz, 2H); $[\alpha]_D^{25}$ −35.28° (c=0.326 g/dL, DMSO).

Example 110

(R,R)-1-[2-(5-Azaphenanthrene-1,10-dicarboximido)propylamino]-2-[2-(3-nitronaphthalene-1,8-dicarboximido)propylamino]ethane Dihydromethanesulfonate 3-Nitro-1,8-naphthalic anhydride (Anselre, F.; Zuckmayer, F. *Chem. Ber.* 1899, 32, 3283) (75 mg, 0.31 mmol) and 5-azaphenanthrene-1,10-dicarboxylic anhydride (77 mg, 0.31 mmol) were added simultaneously to a solution of (R,R)-1,2-bis-(2-aminopropylamino)ethane (U.S. patent application Ser. No. 92/02134) (54 mg, 0.31 mmol) in 3 mL of THF. The mixture was heated at reflux overnight and the dark suspension was cooled to room temperature. The solvent was removed under reduced pressure and the residue was chromatographed on silica gel. Elution with 5% methanol in dichloromethane gave 29 mg (15%) of the free base: $^1$H NMR (300 MHz, CDCl$_3$) δ 9.42 (d, 1H), 9.13 (m, 2H), 8.98 (d, 1H), 8.78 (s, 1H), 8.60 (dd, 2H), 8.40 (dd, 1H), 8.28 (d, 1H), 7.83 (m, 2H), 7.65 (dd, 1H), 5.22 (m, 2H), 3.41 (m, 2H), 2.92 (m, 2H), 2.77 (m, 4H), 1.90 (br s, 2H), 1.43 (d, 3H), 1.42 (d, 3H); MS (CI, NH$_3$) m/e 631 (M+H$^+$). The free base was converted to the di-methanesulfonate salt by treatment with methanesulfonic acid (6.0 μL, 0.09 mmol) in dichloromethane (2 mL). After being stirred overnight, the reaction mixture was concentrated under reduced pressure to give 35 mg of the salt: mp 167°-172° C. (dec).

Example 111

Part A:

4-(3-Aminopropylamino)-1-(3-nitronaphthalene-1,8-dicarboximido)butane Dihydromethanesulfonate Formalin (3.4 mL, 45.0 mmol) was added to a solution of spermidine (6.53 g, 45.0 mmol) in ethanol (50 mL) and the resulting mixture was stirred at room temperature for 13 h (McManis, J. S.; Ganem, B. *J. Org. Chem.* 1980, 45, 2042). This mixture was diluted with ethanol (100 mL) and 3-nitro-1,8-naphthalic anhydride (10.94 g, 45.0 mmol) was added. The brown mixture was heated at reflux for 4 h, cooled somewhat, and methanesulfonic acid (7.3 mL, 112.5 mmol) and water (10 mL) were added. This mixture was heated at reflux for 14 h, filtered hot, and the filtrate allowed to cool to room temperature. The precipitated solid was collected on a frit, washed with ethanol (2×20 mL), and dried. This orange solid was heated at reflux in ethanol (150 mL) for 30 rain and the hot suspension was filtered. The light brown solid was washed with hot ethanol (50 mL) and dried to give 10.09 g (39%) of the product: mp 143°-147° C.; $^1$H NMR (DMSO-d$_6$, 300 MHz) δ 1.65-1.80 (br m, 4H), 1.88 (pentet, 2H, J=7.0 Hz), 2.35 (s, 6H), 2.84-3.06 (br m, 6H), 4.13 (t, 2H, J=6.2 Hz), 7.70-7.85 (br m, 3H), 8.10 (dd, 1H, J=8.1, 7.7 Hz), 8.31-8.45 (br m, 2H), 8.72 (dd, 1H, J=7.3, 1.1 Hz), 8.83 (dd, 1H, J=8.1, 0.8 Hz), 8.99 (d, 1H, J=2.2 Hz), 9.54 (d, 1H, J=2.2 Hz); MS (CI, NH$_3$) m/e (%) 371 (M+H$^+$ free base, 65), 341 (100), 284 (18).

Part B:

4-[3-(3-Nitro-5-azaphenanthrene-1,10-dicarboximido)propylamino]-1-(3-nitronaphthalene-1,8-dicarboximido)butane Hydromethanesulfonate Triethylamine (0.42 mL, 3.0 mmol) was added to a suspension of the mono-imide from part A (1.12 g, 2.0 mmol) and 3-nitro-5-azaphenanthrene-1,10-dicarboxylic anhydride (0.59 g, 2.0 mmol) in ethanol (20 mL). The resulting suspension was heated at reflux for 15 h, cooled, and methanesulfonic acid (0.19 mL, 3.0 mmol) was added. The mixture was heated at reflux for 8 h and filtered hot. The solid was washed with ethanol (10 mL) and dried. The crude salt was heated at reflux in ethanol (25 mL) for 7.5 h and filtered hot. The solid was washed with ethanol (10 mL) and dried to give 1.07 g (72%) of the bis-imide salt: mp 210°-212° C.; $^1$H NMR (DMSO-d$_6$, 300 MHz) δ 1.65-1.81 (m, 4H), 2.02-2.12 (m, 2H), 2.32 (s, 3H), 2.94-3.15 (m, 4H), 4.12 (br t, 2H, J=7.5 Hz), 4.20 (br t, 2H, J=7.5 Hz), 8.04 (dd, 1H, J=8.4, 4.8 Hz), 8.08 (dd, 1H, obscured J=8.0 Hz), 8.29-8.40 (br m, 1H), 8.70 (d, 1H, J=7.4 Hz), 8.81 (d, 1H, J=8.4 Hz), 8.95-9.00 (m, 2H), 9.14 (d, 1H, J=2.2 Hz), 9.29 (s, 1H), 9.36 (dd, 1H, J=4.4, 1.4 Hz), 9.52 (d, 1H, J=2.2 Hz), 10.16 (d, 1H, J=2.2 Hz); MS (CI, NH$_3$) m/e (%) 647 (M+H$^+$ free base, 100), 618 (6), 352 (26), 351 (29).

Example 112

4-[3-(3-Amino-5-azaphenanthrene-1,10-dicarboximido)propylamino]-1-(3-nitronaphthalene-1,8-dicarboximido)butane Dihydromethanesulfonate As in example 111, 3-amino-5-azaphenanthrene-1,10-dicarboxylic anhydride hydrochloride was condensed with the mono-imide, except that 2.5 equivalents of triethylamine and 3 equivalents of methanesulfonic acid were used to give the dimethanesulfonate salt of the bis-imide (69%): mp 247°-252° C. (dec); $^1$H NMR (DMSO-d$_6$, 300 MHz) δ 1.58-1.76 (br m, 4H), 1.94-2.06 (br m, 2H), 2.30 (s, 6H), 2.89- 3.08 (br m, 4H), 4.04-4.15 (m, 4H), 7.76 (dd, 1H, J=8.1, 4.4 Hz), 7.97 (d, 1H, J=2.2 Hz), 8.05 (dd, 1H, J=8.1, 7.7 Hz ), 8.22-8.32 (br m, 2H), 8.54 (d, 1H, J=2.2 Hz), 8.56 (s, 1H), 8.64-8.70 (m, 2H), 8.78 (d, 1H, J=8.4 Hz), 8.94 (d, 1H, J=2.6 Hz), 9.08 (dd, 1H, J=4.4, 1.8 Hz), 9.49 (d, 1H, J=2.6 Hz); MS (CI, NH$_3$) m/e (%) 647 (7), 617 (M+H$^+$ free base, 100), 587 (20), 352 (12), 321 (13), 264 (28).

Example 113

(R,R)-1-[2-(7-Azaphenanthrene-1,10-dicarboximido)-propylamino]-2-[2-(3-nitronaphthalene-1,8-dicarboximido)propylamino]ethane Dihydromethanesulfonate As in example 110, 3-nitro-1,8-naphthalic anhydride and 7-azaphenanthrene-1,10-dicarboxylic anhydride were condensed with (R,R)-1,2-bis-(2-aminopropylamino)ethane (U.S. patent application Ser. No. 92/02134) to give the free base (14%): $^1$H NMR (300 MHz, CDCl$_3$) δ 9.45 (s, 1H), 9.19 (d, 1H), 9.02 (d, 1H), 8.93 (m, 3H), 8.67 (d, 2H), 8.41 (d, 1H), 8.33 (d, 1H), 7.92 (t, 1H), 7.87 (t, 1H), 5.25 (m, 2H), 3.42 (m, 2H), 2.93 (m, 2H), 2.75 (m, 4H), 1.98 (br s, 2H), 1.47 (d, 3H), 1.42 (d, 3H). The free base was converted to the di-methanesulfonate salt (78%): mp 193°-205° C. (dec); MS (CI, NH$_3$) m/e 631 (M+H+ freebase).

Example 114

4-[3-(8-Azaphenanthrene-1,10-dicarboximido)-propylamino]-1-(3-nitronaphthalene-1,8-dicarboximido)butane Hydromethanesulfonate As in example 121, 8-azaphenanthrene-1,10-dicarboxylic anhydride was condensed with the monoimide to give the mono-methanesulfonate salt of the bis-imide (53%), containing a small amount of the symmetrical bis-imide: mp 255°-258° C. (dec); $^1$H NMR (DMSO-d$_6$, 300 MHz) δ 1.61-1.80 (br m, 4H), 2.01-2.12 (m, 2H), 2.32 (s, 3H), 2.92-3.12 (br m, 4H), 4.06-4.21 (m, 4H), 7.97 (dd, 1H, J=8.4, 4.4 Hz), 8.03-8.14 (m, 2H), 8.25-8.38 (br m, 2H), 8.60 (d, 1H, J=7.3 Hz), 8.69 (d, 1H, J=7.3 Hz), 8.80 (d, 1H, J=8.1 Hz), 8.86 (s, 1H), 8.96 (d, 1H, J=2.2 Hz), 9.19 (d, 1H, J=3.7 Hz), 9.34 (d, 1H, J=8.0 Hz), 9.44 (d, 1H, J=8.1 Hz ), 9.50 (d, 1H, J=2.2 Hz); MS (CI, NH$_3$) m/e (%) 608 (10), 602 (M+H+ free base, 100), 572 (7), 313 (6), 306 (14).

Example 115

4-[3-(3-Nitro-8-azaphenanthrene-1,10-dicarboximido)-propylamino]-1-(3-nitronaphthalene-1,8-dicarboximido)butane Hydromethanesulfonate As in example 111, 3-nitro-8-azaphenanthrene-1,10-dicarboxylic anhydride was condensed with the monoimide to give the mono-methanesulfonate salt of the bis-imide (71%), containing a small amount of the symmetrical bis-imide: mp 219°-223° C. (dec); $^1$H NMR (DMSO-d$_6$, 300 MHz) δ 1.61-1.82 (br m, 4H), 2.02-2.14 (br m, 2H), 2.32 (s, 3H), 2.95.-3.15 (br m, 4H), 4.08-4.25 (br m, 4H), 8.00-8.11 (m, 2H), 8.32-8.45 (br m, 1H), 8.70 (d, 1H, J=7.7 Hz), 8.80 (d, 1H, J=8.1 Hz ), 8.97 (d, 1H, J=2.2 Hz), 9.01 (s, 1H), 9.11 (d, 1H, J=1.8 Hz), 9.28 (d, 1H, J=4.4 Hz), 9.52 (d, 1H, J=2.2 Hz), 9.70 (d, 1H, J=7.7 Hz ), 10.09 (d, 1H, J=1.8 Hz ); MS (CI, NH$_3$) m/e (%) 698 (12), 647 (M+H+ free base, 100), 617 (34), 352 (50), 311 (23), 294 (28), 264 (13).

Example 116

(R,R)-1-[2-(3-Nitro-8-azaphenanthrene-1,10-dicarboximido)propylamino]-2-[2-(3-nitronaphthalene1,8-dicarboximido)propylamino]ethane Dihydromethanesulfonate 3-Nitro-8-azaphenanthrene-1,10-dicarboxylic anhydride was condensed with (R,R)-1-[2-aminopropylamino]-2-[2-(3-nitronaphthalene-1,8-dicarboximido)propylamino]ethane (U.S. patent application Ser. No. 07/919,227.) The crude solid was chromatographed on silica gel using a graduated solvent system starting with 2% methanol in dichloromethane and ending with 10% methanol in dichloromethane to give the free base (9%). The free base was converted directly to the di-methanesulfonate salt (33%): mp 185°-186° C.; $^1$H NMR (DMSO-d$_6$, 300 MHz) δ 10.11 (s, 1H), 9.73 (d, 1H), 9.53 (s, 1H), 9.28 (d, 1H), 9.11 (s, 1H), 9.02 (s, 1H), 8.96 (d, 1H), 8.81 (d, 1H), 8.69, (d, 1H), 8.08 (m, 2H), 5.47 (m, 2H), 3.93-3.28 (m, 8H), 2.25 (s, 6H), 1.59 (m, 6H); MS (CI, NH$_3$) m/e 676 (M+H+ free base).

Example 140

4-[3-(2-Methyl-1H-naphth[1,2-d]imidazole-5,6-dicarboximido)propylamino]-1-(3-nitronaphthalene-1,8-dicarboximido)butane Dihydromethanesulfonate As in example 111, 2-methyl-1H-naphth[1,2-d]imidazole-5,6-dicarboxylic anhydride was condensed with the mono-imide, except 2 equivalents of methanesulfonic acid were used to give the dimethanesulfonate salt of the bis-imide (63%), containing a small amount of the symmetrical bis-imide: mp 232°-234° C. (dec); $^1$H NMR (DMSO-d$_6$, 300 MHz) δ 1.59-1.75 (br m, 4H), 1.95-2.05 (br m, 2H), 2.30 (s, 6H), 2.68 (s, 3H), 2.89-3.05 (br m, 4H), 4.07 (br t, 2H, J=7.5 Hz), 4.12 (br t, 2H, J=6.0 Hz), 7.93 (dd, 1H, J=8.1, 7.7 Hz), 8.04 (dd, 1H, J=8.1, 7.6 Hz), 8.21-8.32 (br m, 1H), 8.46 (dd, 1H, J=7.3, 0.7 Hz), 8.54 (s, 1H), 8.66 (dd, 1H, J=7.7, 0.7 Hz), 8.74-8.82 (m, 2H), 8.92 (d, 1H, J=2.6 Hz), 9.48 (d, 1H, J=2.2 Hz); MS (CI, NH$_3$) m/e (%) 605 (M+H+ free base, 44), 596 (20), 352 (29), 314 (100), 309 (58), 285 (30), 252 (28).

Tables 1-8 show compounds of this invention which are exemplified herein or which may be prepared using methods disclosed herein.

TABLE I

Azaphenanthrene Compounds.

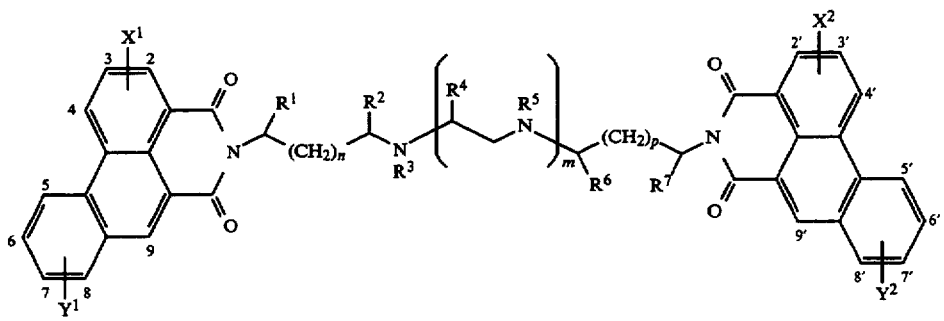

| Ex | N posn | X¹ | Y¹ | X² | Y² | R¹ | R² | R³ | R⁴ | R⁵ | R⁶ | R⁷ | n | m | p | mp |
|---|---|---|---|---|---|---|---|---|---|---|---|---|---|---|---|---|
| 1 | 5 | 5' | H | H | H | H | H | H | H | — | — | H | H | 2 | 0 | 1 | 252–257 |
| 2 | 5 | 5' | 3-NO₂ | H | 3'-NO₂ | H | H | H | H | — | — | H | H | 0 | 0 | 0 | 272–275 |
| 3 | 5 | 5' | 3-NO₂ | H | 3'-NO₂ | H | H | H | H | — | — | H | H | 0 | 0 | 1 | 263–265 |
| 4 | 5 | 5' | 3-NO₂ | H | 3'-NO₂ | H | H | H | H | — | — | H | H | 1 | 0 | 1 | 285–286 |
| 5 | 5 | 5' | 3-NO₂ | H | 3'-NO₂ | H | H | H | H | — | — | H | H | 2 | 0 | 1 | 298–301 |
| 6 | 5 | 5' | 3-NO₂ | H | 3'-NO₂ | H | H | H | H | H | H | H | H | 0 | 1 | 0 | 284.5–287 |
| 7 | 5 | 5' | 3-NO₂ | H | 3'-NO₂ | R | (S)-Me | H | H | H | H | H | (S)-Me | 0 | 1 | 0 | 220–222 |
| 8 | 5 | 5' | 3-NO₂ | H | 3'-NO₂ | H | (R)-Me | H | H | H | H | H | (R)-Me | 0 | 1 | 0 | 211–215 |
| 9 | 5 | 5' | 3-NH₂ | H | 3'-NH₂ | H | H | H | H | — | — | H | H | 2 | 0 | 1 | 285–288 |
| 10 | 5 | 5' | H | 7-Me | H | 7'-Me | H | H | H | — | — | H | H | 2 | 0 | 1 | 198–200 |
| 11 | 5 | 5 | H | 7-NO₂ | H | 7'-NO₂ | H | H | H | — | — | H | H | 2 | 0 | 1 | 228–230 |
| 12 | 5 | 5' | 3-NO₂ | 7-Me | 3'-NO₂ | 7'-Me | H | H | H | — | — | H | H | 2 | 0 | 1 | >280 |
| 13 | 5 | 5' | 3-NO₂ | 7-Me | 3'-NO₂ | 7'-Me | (R)-Me | H | H | H | H | H | (R)-Me | 0 | 1 | 0 | 221–223.5 |
| 14 | 6 | 6' | H | H | H | H | H | H | H | — | — | H | H | 2 | 0 | 1 | 190–195 |
| 15 | 7 | 7' | H | H | H | H | H | H | H | — | — | H | H | 2 | 0 | 1 | 265–272 |
| 16 | 7 | 7' | 3-NO₂ | H | 3'-NO₂ | H | H | H | H | — | — | H | H | 2 | 0 | 1 | 195–200 |
| 17 | 8 | 8' | H | H | H | H | H | H | H | — | — | H | H | 2 | 0 | 1 | 243–247 |
| 18 | 8 | 8' | 3-NO₂ | H | 3'-NO₂ | H | H | H | H | — | — | H | H | 2 | 0 | 1 | 212–215 |
| 19 | 8 | 8' | 3-NO₂ | H | 3'-NO₂ | H | H | H | H | H | H | H | H | 0 | 1 | 0 | 267–270 |
| 20 | 5 | 5' | 3-NO₂ | H | 3'-NO₂ | H | H | (S)-Me | H | H | H | (S)-Me | H | 0 | 1 | 0 | >275 |
| 21 | 5 | 5' | 3-NO₂ | H | 3'-NO₂ | H | (R)-Me | H | H | (R)-Me | H | H | (R)-Me | 0 | 1 | 0 | 245–246 |
| 22 | 5 | 5' | 3-NO₂ | 7-Me | 3'-NO₂ | 7'-Me | H | H | H | — | — | H | H | 0 | 0 | 1 | 271–273 |
| 23 | 5 | 5' | 3-NO₂ | 7-Me | 3'-NO₂ | 7'-Me | H | H | H | H | H | H | H | 0 | 1 | 0 | 265–267 |
| 24 | 5 | 5' | 3-NO₂ | 7-Me | 3'-NO₂ | 7'-Me | (R)-Et | H | H | H | H | H | (R)-Et | 0 | 1 | 0 | 243–244 |
| 25 | 5 | 5' | 3-NO₂ | 7-Me | 3'-NO₂ | 7'-Me | (R)-Me | H | H | (S)-Me | H | H | (R)-Me | 0 | 1 | 0 | 246–247 |
| 26 | 5 | 5' | 3-NO₂ | 7-Me | 3'-NO₂ | 7'-Me | H | (S)-Me | H | H | H | (S)-Me | H | 0 | 1 | 0 | 250–253 |
| 27 | 5 | 6' | 3-NO₂ | H | H | H | (R)-Me | H | H | H | H | H | (R)-Me | 0 | 1 | 0 | |
| 28 | 5 | 7' | 3-NO₂ | H | H | H | (R)-CH₂OH | H | H | H | H | H | (R)-Me | 0 | 1 | 0 | |
| 29 | 5 | 8' | 3-NH₂ | H | 3'-NO₂ | H | H | (R)-Me | H | (R)-Me | H | (R)-Me | H | 0 | 1 | 0 | |
| 30 | 5,8 | 5',8' | H | H | H | H | (R)-Me | H | H | — | — | H | (R)-Me | 1 | 0 | 1 | |
| 31 | 5,8 | 5',8' | 3-NO₂ | H | 3'-NO₂ | H | (S)-CH₂—CH₂SMe | H | H | H | H | H | (S)-CH₂—CH₂SMe | 0 | 1 | 0 | |
| 32 | 5,8 | 5',8' | 3-NO₂ | 7-Me | 3'-NO₂ | 7'-Me | (S)-CH₂—NH₂ | H | H | H | H | H | (S)-CH₂—NH₂ | 0 | 1 | 0 | |
| 33 | 6,8 | 6',8' | H | H | H | H | (R)-Et | H | H | H | H | H | (R)-Me | 0 | 1 | 0 | |
| 34 | 6,8 | 6',8' | 3-NO₂ | H | 3'-NO₂ | H | (R)-Me | H | H | H | H | H | (R)-CH₂—CH₂SMe | 0 | 1 | 0 | |
| 35 | 5 | 5' | 3-NO₂ | H | H | 6'-NH₂ | H | (S)-Me | H | — | — | (S)-Me | H | 1 | 0 | 1 | |
| 36 | 8 | 8' | H | 7-SO₂Me | H | 7'-SO₂Me | H | H | Et | H | Et | H | H | 0 | 1 | 0 | |
| 37 | 5 | 5' | H | 7-CN | H | 7'-CN | (S)-Me | H | H | — | — | H | (S)-Me | 0 | 0 | 0 | |
| 38 | 5 | 5' | 3-NO₂ | H | H | 8'-NH₂ | (R)-CH₂—CH=CH₂ | H | H | H | H | H | (R)-Me | 0 | 1 | 0 | |
| 39 | 5 | 5' | 3-NO₂ | H | H | 8'-OMe | H | H | H | H | H | H | (S)-Me | 0 | 1 | 0 | |

TABLE II

Phenanthrene Compounds.

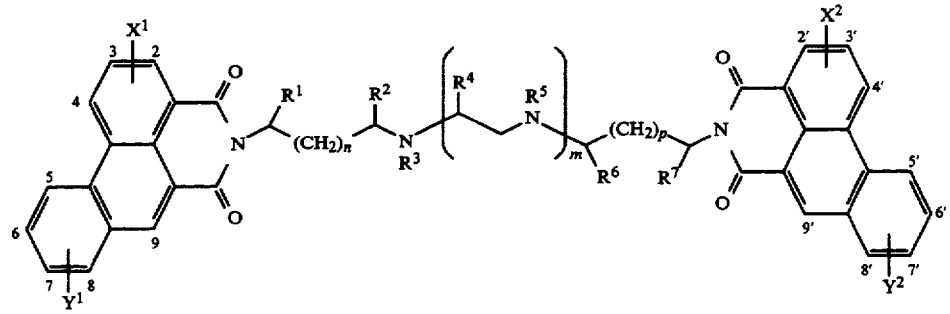

| Ex | X¹ | Y¹ | X² | Y² | R¹ | R² | R³ | R⁴ | R⁵ | R⁶ | R⁷ | n m p | mp |
|---|---|---|---|---|---|---|---|---|---|---|---|---|---|
| 40 | H | H | H | H | H | H | H | — | — | H | H | 2 0 1 | |
| 41 | H | 6-Me | H | 6'-Me | H | H | H | — | — | H | H | 2 0 1 | 165-170 |
| 42 | H | 8-Me | H | 8'-Me | H | H | H | — | — | H | H | 2 0 1 | 273-275 |
| 43 | H | 9-Me | H | 9'-Me | H | H | H | — | — | H | H | 2 0 1 | 271-274 |
| 44 | H | 6-CF₃ | H | 6'-CF₃ | H | H | H | — | — | H | H | 2 0 1 | 310-312 |
| 45 | H | 9-CF₃ | H | 9'-CF₃ | H | H | H | — | — | H | H | 2 0 1 | 235-237 |
| 46 | 6-Me | 9-Me | 6'-Me | 9'-Me | H | H | H | — | — | H | H | 2 0 1 | 219-222 |
| 47 | H | 6-Et | H | 6'-Et | H | H | H | — | — | H | H | 2 0 1 | 197-199 |
| 48 | H | 9-Ph | H | 9'-Ph | H | H | H | — | — | H | H | 2 0 1 | 158-161 |
| 49 | H | 6-CN | H | 6'-CN | H | H | H | — | — | H | H | 2 0 1 | >320 |
| 50 | 3-NO₂ | H | 3'-NO₂ | H | H | H | H | — | — | H | H | 2 0 1 | >240 |
| 51 | H | 5-NO₂ | H | 5'-NO₂ | H | H | H | — | — | H | H | 2 0 1 | 292 |
| 52 | H | 6-NO₂ | H | 6'-NO₂ | (S)-Me | H | H | H | H H | H | (S)-Me | 0 1 0 | 253-255 |
| 53 | 3-NH₂ | H | 3'-NH₂ | H | H | H | H | — | — | H | H | 2 0 1 | 280 |
| 54 | H | 7-OMe | H | 7'-OMe | H | H | H | — | — | H | H | 2 0 1 | 162-165 |
| 55 | 6-OMe | 7-OMe | 6'-OMe | 7'-OMe | H | H | H | — | — | H | H | 2 0 1 | 254-257 |
| 56 | H | 6-F | H | 6'-F | H | H | H | — | — | H | H | 2 0 1 | 300-306 |
| 57 | 3-NO₂ | 6-CF₃ | 3'-NO₂ | 6'-CF₃ | H | H | H | — | — | H | H | 0 0 0 | |
| 58 | 3-NO₂ | 6-CN | 3'-NO₂ | 6'-CN | H | H | H | — | — | H | H | 1 0 1 | |
| 59 | H | 8-CN | H | 8'-CN | (R)-Me | H | H | — | — | H | (R)-Me | 0 0 0 | |
| 60 | H | 8-CF₃ | H | 8'-CF₃ | (S)-CH₂—CH₂SMe | H | H | — | — | H | (S)-CH₂—CH₂SMe | 1 0 1 | |
| 61 | 3-NO₂ | 8-CN | 3'-NO₂ | 8'-CN | (R)-CH₂—CH₂NH₂ | H | H | H | H H | H | (R)-CH₂—CH₂NH₂ | 0 1 0 | |
| 62 | 3-NO₂ | 8-CF₃ | 3'-NO₂ | 8'-CF₃ | (S)-Et | H | H | H | H H | H | (S)-Et | 0 1 0 | |
| 63 | 3-NO₂ | 6-NO₂ | 3'-NO₂ | 6'-NO₂ | (R)-Me | H | H | H | H H | H | (R)-CH₂—NH₂ | 0 0 0 | |
| 64 | H | 8-NO₂ | H | 8'-NO₂ | (R)-Et | H | H | H | H H | H | (S)-CH₂—OH | 0 1 0 | |
| 65 | 3-NO₂ | 8-NO₂ | 3'-NO₂ | 8'-NO₂ | (S)-Et | H | H | (S)-Et | H H | H | (S)-Et | 0 1 0 | |
| 66 | H | 6-CN | H | 6'-CF₃ | (S)-Me | H | H | H | H H | H | (S)-Me | 0 1 0 | |
| 67 | H | 6-CN | H | 8'-CF₃ | H | (R)-Me | H | H | H | (R)-Me | H | 0 1 0 | |
| 68 | 3-NO₂ | 6-CN | H | 8'-CN | (R)-Me | H | H | H | H H | H | (R)-Me | 0 1 0 | |
| 69 | H | 6-SO₂Me | H | 6'-SO₂Me | H | (S)-Me | H | (S)-Me | H | (S)-Me | H | 0 1 0 | |
| 70 | H | 6-CN | H | 6'-F | (R)-CH₂—OH | H | H | (R)-Me | H H | H | (R)-CH₂—OH | 0 1 0 | |
| 71 | H | 6-CN | H | 6'-SO₂Me | H | H | H | — | — | H | H | 2 0 1 | |
| 72 | 3-NO₂ | 6-NH₂ | 3'-NO₂ | 6'-NH₂ | (R)-Me | H | H | — | — | H | H | 0 0 0 | |
| 73 | 3-NO₂ | 8-NH₂ | 3'-NO₂ | 6'-NH₂ | (S)-CH₂—OMe | H | H | H | H H | H | (R)-Me | 0 1 0 | |
| 74 | 3-NO₂ | H | H | 6'-NH₂ | (R)-Me | H | H | H | H H | H | (R)-i-Pr | 0 0 2 | |
| 75 | 3-NO₂ | H | H | 8'-NH₂ | H | H | CH₂—CH=CH₂ | H | H H | H | (R)-Me | 0 1 0 | |
| 76 | H | 6-CN | H | 8'-NH₂ | (R)-CH₂—Ph | H | H | H | H H | H | (R)-CH₂—CH₂NH₂ | 0 1 0 | |
| 77 | H | 8-CN | H | 8'-NH₂ | (R)-Me | (R)-Me | H | H | H | (R)-Me | (R)-Me | 0 1 0 | |
| 78 | 3-NO₂ | 6-CN | H | 6'-NH₂ | (R)-Me | H | H | (S)-CH₂—CH₂SMe | H H | H | (R)-Me | 0 1 0 | |
| 79 | 3-NO₂ | 8-NO₂ | H | 8'-SO₂Me | H | (R)-Me | H | — | — | (R)-Me | H | 0 0 0 | |

TABLE III

Five-membered Ring Heterocycles I.

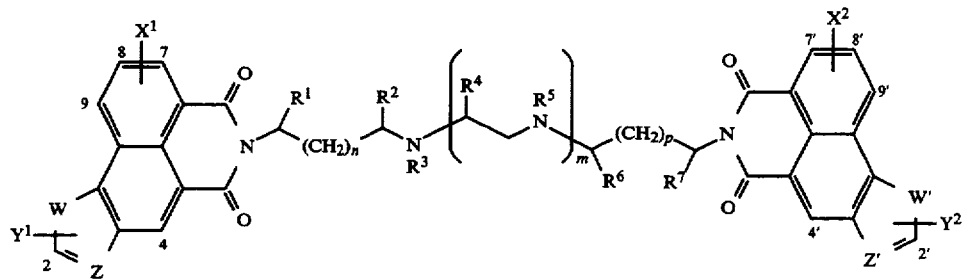

| Ex | W | Z | X¹ | Y¹ | W' | Z' | X² | Y² | R¹ | R² | R³ | R⁴ | R⁵ | R⁶ | R⁷ | n | m | p | mp |
|----|---|---|----|----|----|----|----|----|----|----|----|----|----|----|----|---|---|---|-----|
| 80 | O | CH | H | H | O | CH | H | H | H | H | H | — | — | H | H | 2 | 0 | 1 | 273–276 |
| 81 | NH | N | H | 2-Me | NH | N | H | 2'-Me | H | H | H | — | — | H | H | 2 | 0 | 1 | 260–261 |
| 82 | S | N | H | 2-Me | S | N | H | 2'-Me | H | H | H | — | — | H | H | 2 | 0 | 1 | 318–321 |
| 83 | S | N | H | 2-Me | S | N | H | 2'-Me | (R)-Me | H | H | H | H | H | (R)-Me | 0 | 1 | 0 | >215 |
| 84 | O | CH | 8-NO₂ | H | O | CH | 8'-NO₂ | H | (R)-CH₂—OH | H | H | H | H | H | (R)-Me | 0 | 1 | 0 | |
| 85 | O | C | H | 3-CN | O | C | H | 3'-CN | H | (R)-Me | H | (R)-Me | H | (R)-Me | H | 0 | 1 | 0 | |
| 86 | S | N | 8-NO₂ | 2-Me | S | N | 8'-NO₂ | 2'-Me | (R)-Me | H | H | — | — | H | (R)-Me | 1 | 0 | 1 | |
| 87 | O | C | H | 3-OMe | O | C | H | 3'-OMe | (R)-Et | H | H | H | H | H | (R)-Me | 0 | 1 | 0 | |
| 88 | NH | N | 8-NO₂ | H | NH | N | H | 2'-NH₂ | H | (S)-Me | H | (S)-Me | H | (S)-Me | H | 0 | 1 | 0 | |
| 89 | NH | N | 8-NO₂ | 2-Me | O | CH | H | H | (S)-CH₂—OMe | H | H | H | H | H | (R)-Me | 0 | 1 | 0 | |

TABLE IV

Five-membered Ring Heterocycles II.

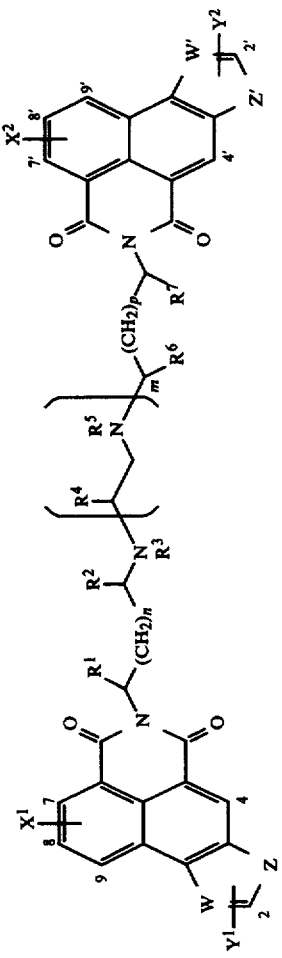

| Ex | W | Z | X¹ | Y¹ | W' | Z' | X² | Y² | R¹ | R² | R³ | R⁴ | R⁵ | R⁶ | R⁷ | n | m | p | mp |
|---|---|---|---|---|---|---|---|---|---|---|---|---|---|---|---|---|---|---|---|
| 90 | CH | O | H | H | CH | O | H | 2'-CN | H | H | H | — | — | H | H | 2 | 0 | 1 | 160-165 |
| 91 | N | S | H | 2-CN | N | S | H | 2'-Me | H | H | H | — | — | H | H | 2 | 0 | 1 | |
| 92 | N | O | H | 2-Me | N | O | H | 2'-NO₂ | (R)-Me | H | H | H | H | (R)-Me | (R)-Me | 0 | 1 | 0 | |
| 93 | CH | O | H | 2-NO₂ | CH | O | H | 2'-NH₂ | H | (R)-Me | H | H | H | (R)-Me | H | 0 | 1 | 0 | |
| 94 | N | S | H | 2-NH₂ | N | S | H | 2'-Me | (S)-Me | H | H | — | — | H | H | 0 | 0 | 1 | |
| 95 | N | S | 8-NO₂ | 2-Me | N | S | 8'-NO₂ | H | (R)-Me | H | H | H | H | H | (S)-Me | 1 | 1 | 0 | |
| 96 | CH | O | 8-NO₂ | H | CH | O | 8'-NO₂ | 2'-Me | H | (R)-CH—CH₂NH₂ | H | H | H | (R)-CH₂—CH₂NH₂ | H | 0 | 1 | 0 | |
| 97 | CH | O | H | H | N | O | 8'-NO₂ | H | (R)-Me | H | H | H | H | (R)-Me | H | 1 | 0 | 0 | |
| 98 | CH | O | H | 2-CN | CH | O | 8'-CN | H | H | H | H | (S)-CH₂—OH | H | H | H | 1 | 0 | 0 | |
| 99 | N | S | 8-CN | 2-Me | N | S | H | 2'-Me | H | H | H | H | H | H | H | 0 | 1 | 0 | |

TABLE V

Pentacyclic Chromophores.

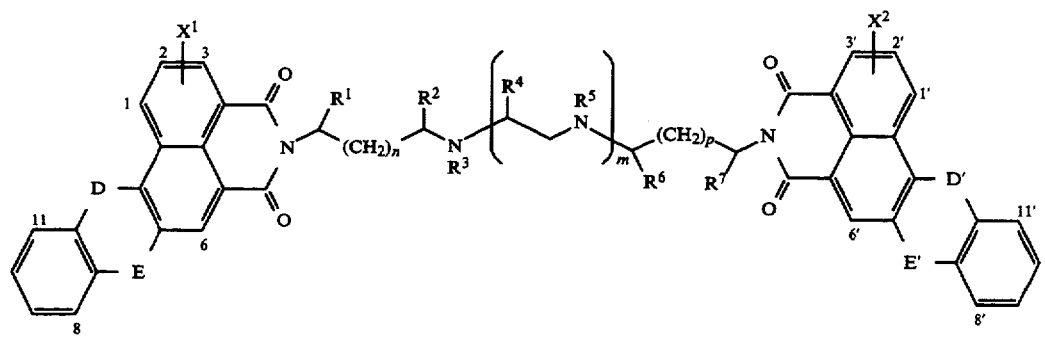

| Ex | D | E | X¹ | D' | E' | X² | R¹ | R² | R³ | R⁴ | R⁵ | R⁶ | R⁷ | n | m | p | mp |
|---|---|---|---|---|---|---|---|---|---|---|---|---|---|---|---|---|---|
| 100 | C=O | C=O | H | C=O | C=O | H | H | H | H | — | — | H | H | 2 | 0 | 1 | 266–268 |
| 101 | C=O | C=O | H | C=O | C=O | H | (R)-Me | H | H | H | H | H | (R)-Me | 0 | 1 | 0 | 208–210 |
| 102 | NH | C=O | H | NH | C=O | H | H | H | H | — | — | H | H | 1 | 0 | 1 | |
| 103 | C=O | NH | H | C=O | NH | H | H | H | H | — | — | H | H | 0 | 0 | 1 | |
| 104 | S | C=O | H | S | C=O | H | H | (S)-CH₂—OH | H | — | — | H | H | 1 | 0 | 0 | |
| 105 | C=O | S | H | C=O | S | H | H | H | H | H | H | H | H | 0 | 1 | 0 | |
| 106 | C=O | C=O | H | NH | C=O | H | (R)-Me | H | H | (R)-Me | H | H | (R)-Me | 0 | 1 | 0 | |
| 107 | C=O | C=O | 2-NO₂ | C=O | C=O | 2'-NO₂ | (S)-Me | H | H | H | H | H | (S)-Me | 0 | 1 | 0 | |
| 108 | C=O | C=O | H | NH | C=O | 2'-NO₂ | (R)-Et | H | H | (R)-Et | H | H | (S)-Et | 0 | 1 | 0 | |
| 109 | S | C=O | H | S | C=O | 2'-NO₂ | (R)-Me | H | H | — | — | H | (R)-Me | 1 | 0 | 1 | |

TABLE VI

Unsymmetrical Chromophores I.

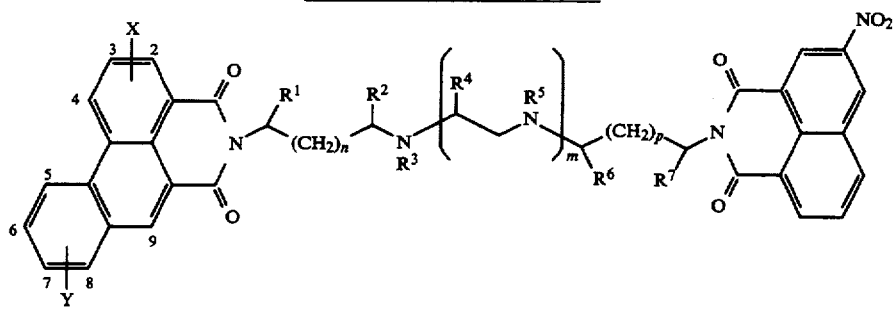

| Ex | N posn | X | Y | R¹ | R² | R³ | R⁴ | R⁵ | R⁶ | R⁷ | n | m | p | mp |
|---|---|---|---|---|---|---|---|---|---|---|---|---|---|---|
| 110 | 5 | H | H | (R)-Me | H | H | H | H | H | (R)-Me | 0 | 1 | 0 | 167–172 |
| 111 | 5 | 3-NO₂ | H | H | H | H | — | — | H | H | 1 | 0 | 2 | 210–212 |
| 112 | 5 | 3-NH₂ | H | H | H | H | — | — | H | H | 1 | 0 | 2 | 247–252 |
| 113 | 7 | H | H | (R)-Me | H | H | H | H | H | (R)-Me | 0 | 1 | 0 | 193–205 |
| 114 | 8 | H | H | H | H | H | — | — | H | H | 1 | 0 | 2 | 255–258 |
| 115 | 8 | 3-NO₂ | R | H | H | H | — | — | H | H | 1 | 0 | 2 | 219–223 |
| 116 | 8 | 3-NO₂ | H | (R)-Me | H | H | H | H | H | (R)-Me | 0 | 1 | 0 | 185–186 |
| 117 | 5 | 3-NO₂ | 7-Me | (R)-Me | H | H | H | H | H | (R)-Me | 0 | 1 | 0 | 229–230 |
| 118 | 6 | H | H | (R)-Me | H | H | H | H | H | (R)-Me | 0 | 1 | 0 | 198–200 |
| 119 | 6 | 3-NO₂ | H | (R)-Me | H | H | H | H | H | (R)-Me | 0 | 1 | 0 | 201–202 |
| 120 | — | H | 6-F | (R)-Me | H | H | H | H | H | (R)-Me | 0 | 1 | 0 | 202–204 |
| 121 | — | H | 6-CF₃ | (R)-Me | H | H | H | H | H | (R)-Me | 0 | 1 | 0 | 210–212 |
| 122 | — | H | 6-OMe | (R)-Me | H | H | H | H | H | (R)-Me | 0 | 1 | 0 | 204–205 |
| 123 | 5 | 3-NO₂ | H | (R)-Me | H | H | H | H | H | (R)-Me | 0 | 1 | 0 | 202–207 |
| 124 | 5 | H | H | H | H | H | — | — | H | H | 1 | 0 | 2 | 262–266 |
| 125 | 8 | H | H | (R)-Me | H | H | H | H | H | (R)-Me | 0 | 1 | 0 | |
| 126 | 7 | 3-NO₂ | H | (R)-Me | H | (R)-Me | H | H | H | (R)-Me | 0 | 1 | 0 | |
| 127 | 5 | H | 8-NH₂ | H | (S)-Et | H | — | — | (S)-Et | H | 1 | 0 | 1 | |
| 128 | 5 | 3-NO₂ | 6-NH₂ | (R)-CH₂—CH₂SMe | H | H | H | H | H | (R)-CH₂—CH₂SMe | 0 | 1 | 0 | |
| 129 | 5,8 | H | H | (R)-CH₂—CH₂NH₂ | H | H | H | H | H | (R)-CH₂—CH₂NH₂ | 0 | 1 | 0 | |
| 130 | 5,7 | H | H | (S)-CH₂—CH₂SMe | H | H | H | H | (R)-CH₂—NH₂ | H | 0 | 1 | 0 | |
| 131 | — | H | 8-OMe | (S)-CH₂—CH₂SMe | H | H | H | H | H | H | 0 | 1 | 0 | |
| 132 | — | H | 8-CN | (R)-CH₂—OH | H | H | H | H | H | (R)-CH₂—OH | 0 | 1 | 0 | |

TABLE VI-continued
Unsymmetrical Chromophores I.

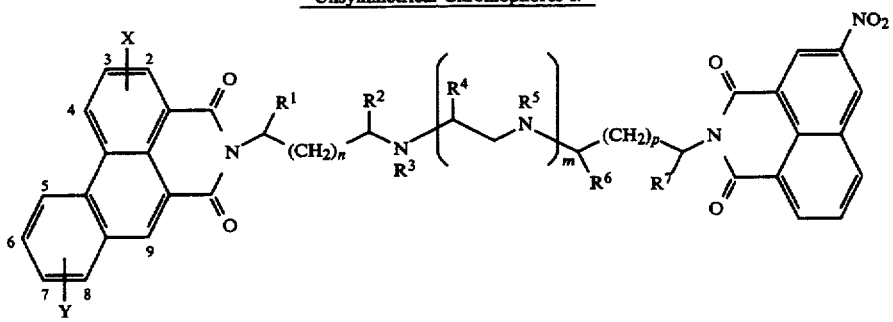

| Ex | N posn | X | Y | R¹ | R² | R³ | R⁴ | R⁵ | R⁶ | R⁷ | n | m | p | mp |
|---|---|---|---|---|---|---|---|---|---|---|---|---|---|---|
| 133 | 8 | 3-NO₂ | 6-Me | (R)-Me | H | H | (S)-CH₂—OMe | H | H | (R)-Me | 0 | 1 | 0 | |
| 134 | 5 | 3-NH₂ | H | (R)-Me | H | H | H | H | H | (R)-Me | 0 | 1 | 0 | |
| 135 | 6 | 3-CN | H | H | (S)-Me | H | (S)-Me | H | (S)-Me | H | 1 | 1 | 1 | |
| 136 | 7 | 3-SO₂Me | H | (S)-CH₂—OMe | H | H | H | H | H | (R)-Me | 0 | 1 | 0 | |
| 137 | 7 | H | 8-NH₂ | (R)-Me | H | H | — | — | H | (R)-Me | 0 | 0 | 0 | |
| 138 | 6 | 3-F | H | H | H | H | H | H | H | H | 0 | 1 | 0 | |
| 139 | 5 | H | 7-CF₃ | H | H | H | — | — | H | H | 1 | 0 | 1 | |

TABLE VII
Unsymmetrical Chromophores II.

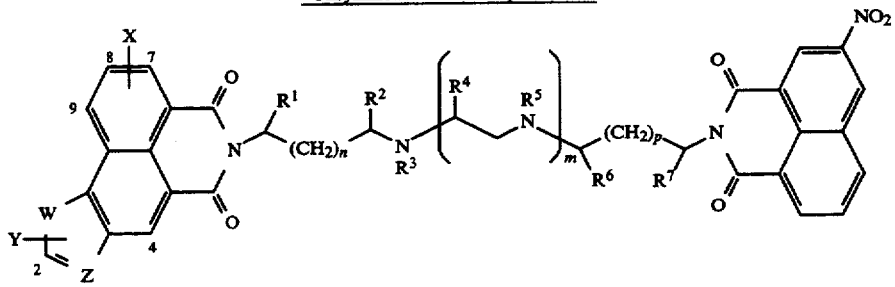

| Ex | W | Z | X | Y | R¹ | R² | R³ | R⁴ | R⁵ | R⁶ | R⁷ | n | m | p | mp |
|---|---|---|---|---|---|---|---|---|---|---|---|---|---|---|---|
| 140 | NH | N | H | 2-Me | H | H | H | — | — | H | H | 1 | 0 | 2 | 232–234 |
| 141 | NH | N | H | 2-NH₂ | H | H | H | H | H | H | H | 0 | 1 | 0 | |
| 142 | S | N | H | 2-Me | H | (R)-Me | H | H | H | H | H | 0 | 1 | 0 | |
| 143 | NH | N | 8-NO₂ | 2-Me | (R)-Me | H | H | H | H | H | (R)-Me | 0 | 1 | 0 | |
| 144 | S | N | 8-CN | H | (S)-Me | H | H | — | — | H | (S)-Me | 1 | 0 | 0 | |
| 145 | O | CH | H | H | H | (S)-CH₂—CH₂SMe | H | H | H | H | H | 0 | 1 | 0 | |

TABLE VIII
Unsymmetrical Chromophores III.

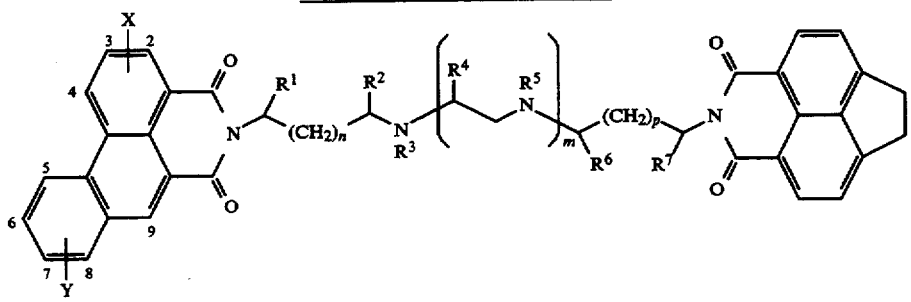

| Ex | N posn | X | Y | R¹ | R² | R³ | R⁴ | R⁵ | R⁶ | R⁷ | n | m | p | mp |
|---|---|---|---|---|---|---|---|---|---|---|---|---|---|---|
| 146 | 5 | H | H | (R)-Me | H | H | H | H | H | (R)-Me | 0 | 1 | 0 | |
| 147 | 5 | 3-NO₂ | H | H | H | — | — | H | H | H | 1 | 0 | 2 | |
| 148 | 5 | 3-NH₂ | H | H | H | — | — | H | H | (R)-Me | 1 | 0 | 2 | |
| 149 | 5 | 3-NO₂ | 7-Me | (R)-Me | H | H | H | H | H | (R)-Me | 0 | 1 | 0 | |

TABLE VIII-continued
Unsymmetrical Chromophores III.

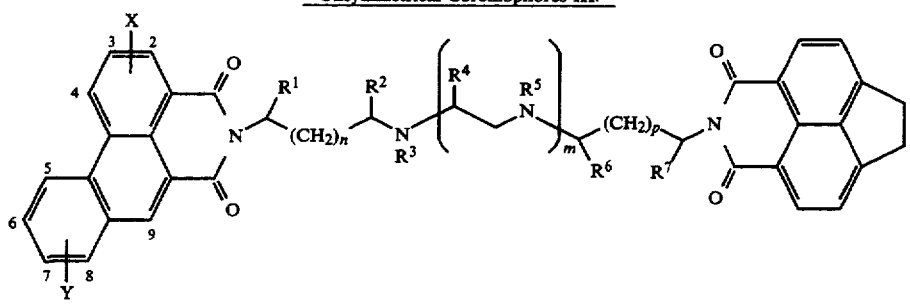

| Ex | N posn | X | Y | R¹ | R² | R³ | R⁴ | R⁵ | R⁶ | R⁷ | n | m | p mp |
|---|---|---|---|---|---|---|---|---|---|---|---|---|---|
| 150 | 5 | 3-NO₂ | 6-NH₂ | H | H | H | — | — | H | H | 1 | 0 | 2 |
| 151 | 5 | H | 7-NH₂ | (S)-Me | H | H | H | H | H | (S)-Me | 1 | 0 | 2 |
| 152 | 6 | H | H | H | H | H | (S)-Et | H | H | H | 0 | 1 | 0 |
| 153 | 6 | 3-NO₂ | H | (R)-Me | H | H | H | H | H | (R)-Me | 0 | 1 | 0 |
| 154 | 6 | 3-NH₂ | H | H | (R)-Me | H | — | — | (R)-Me | H | 0 | 0 | 0 |
| 155 | 6 | 3-CN | H | (R)-Me | H | H | (S)-Me | H | H | (R)-Me | 0 | 1 | 0 |
| 156 | 6 | 3-F | H | H | H | H | (R)-CH₂—OMe | H | H | H | 0 | 1 | 0 |
| 157 | 7 | H | H | (R)-Me | H | H | H | H | H | (R)-Me | 0 | 1 | 0 |
| 158 | 7 | 3-NO₂ | H | H | (S)-Me | H | H | H | (S)-Me | H | 0 | 1 | 0 |
| 159 | 7 | 3-NO₂ | 6-NH₂ | (R)-Me | H | H | H | H | H | (R)-Me | 0 | 1 | 0 |
| 160 | 7 | 3-SO₂Me | H | H | H | H | — | — | H | H | 1 | 0 | 1 |
| 161 | 7 | H | 8-NH₂ | (R)-Me | H | H | H | H | H | (R)-Me | 0 | 1 | 0 |
| 162 | 8 | H | H | (R)-Me | H | H | (R)-Me | H | H | (R)-Me | 0 | 1 | 0 |
| 163 | 8 | 3-NO₂ | H | H | (S)-Et | H | — | — | (S)-Et | H | 1 | 0 | 1 |
| 164 | 8 | 3-NH₂ | H | (R)-CH₂—CH₂SMe | H | H | H | H | H | (R)-CH₂—CH₂SMe | 0 | 1 | 0 |
| 165 | 8 | 3-NO₂ | 6-Me | (R)-CH₂—CH₂NH₂ | H | H | H | H | H | (R)-CH₂—CH₂NH₂ | 0 | 1 | 0 |
| 166 | 5,8 | H | H | (S)-CH₂—CH₂SMe | H | H | H | H | (R)-CH₂—NH₂ | H | 0 | 1 | 0 |
| 167 | 5,8 | 3-NO₂ | H | (S)-CH₂—CH₂SMe | H | H | H | H | H | H | 0 | 1 | 0 |
| 168 | 5,8 | 3-NH₂ | H | (R)-CH₂—OH | H | H | H | H | H | (R)-CH₂—OH | 0 | 1 | 0 |
| 169 | 5,8 | 3-CN | H | (R)-Me | H | H | (S)-CH₂—OMe | H | H | (R)-Me | 0 | 1 | 0 |
| 170 | 5,7 | 3-NO₂ | H | (R)-Me | H | H | H | H | H | (R)-Me | 0 | 1 | 0 |
| 171 | 5,7 | 3-NO₂ | 6-NH₂ | H | (S)-Me | H | (S)-Me | H | (S)-Me | H | 1 | 1 | 1 |
| 172 | 5,7 | 3-NH₂ | H | (S)-CH₂—OMe | H | H | H | H | H | (R)-Me | 0 | 1 | 0 |
| 173 | 5,7 | 3-NH₂ | 6-NH₂ | (R)-Me | H | H | — | — | H | (R)-Me | 0 | 0 | 0 |
| 174 | 6,8 | H | H | H | H | H | H | H | H | H | 0 | 1 | 0 |
| 175 | 6,8 | 3-NO₂ | H | H | H | H | — | — | H | H | 1 | 0 | 1 |
| 176 | — | H | 6-F | H | H | H | H | H | H | H | 0 | 1 | 0 |
| 177 | — | H | 6-CF₃ | (R)-Me | H | H | H | H | H | (R)-Me | 0 | 1 | 0 |
| 178 | — | H | 8-OMe | (S)-Me | H | H | H | H | H | H | 0 | 1 | 0 |
| 179 | — | H | 6-OMe | (R)-Me | H | H | — | — | H | (R)-Me | 0 | 0 | 0 |

UTILITY

Representative compounds of the present invention have been tested in a variety of preclinical assays that are reliable predictive of clinical utility. The anti-tumor activity of the compounds of the present invention was evaluated in the animal tumor cell culture models as well as in the animal tumor models described below, including human tumor xenograft models.

The demonstrated effectiveness of the compounds of the present invention in the tumor models indicate that they may be useful for the treatment of leukemia and solid tumors in man, and, in particular, tumors of the breast, colon, and lung. This conclusion is further supported by published analyses correlating pre-clinical test results with clinical efficacy of anti-cancer agents. For example, see: Goldin and Venditti (1980) Cancer Research 76: 176–191; Goldin et al. (1981) Eur. J. Cancer 17: 129–142; Mattern et al. (1988) Cancer and Metastasis Review 7: 263–284; Jackson et al. (1990) Cancer Investigations 8: 39–47. Based on these published analyses, the exceptional high level of anti-tumor activity exhibited by the presently claimed compounds provide strong evidence that they have important therapeutic utility in the treatment of cancer in man.

In Vitro Growth Inhibitory Activity

Materials and Methods

The reagents for tissue culture were purchased from GIBCO (Grand Island, N.Y.). 5-Dimethylthiazol-2-yl)-2,5-diphenyl tetrazolium bromide (MTT) was purchased from Sigma Chemical Company (St. Louis, Mo.). All agents were prepared as 2 mg/ml stock solutions in DMSO. MTT was prepared as a 1 mg/ml stock solution in Dulbecco's phosphate buffered saline (PBS). All stocks were stored frozen in the dark at −20° C.

Cell Culture

Clone A human colon cancer cells were isolated from the heterogeneous DLD-1 colon tumor line and maintained as previously described (Dexter, D. L.; Barbosa, J. A.; Calabresi, P. *Cancer Research* 1979, 39, 1020; Dexter, D. L.; Spremulli, E. M.; Fligiel, A.; Barbosa, J. A.; Vogel, R.; Van Vorhees, A.; Calabresi, P. *Am. J. Med.* 1981, 71, 949.). Murine leukemia L1210 cells were maintained in RPMI-L medium as described (Chen, S.-F.; Ruben, R. L.; Dexter, D. L. *Cancer Research* 1986, 46, 5014.). All cell lines were incubated at 37° C. in a humidified atmosphere of 5% $CO_2$-95% air.

Exponentially growing L1210 cells ($1\times 10^3$), or Clone A cells ($8\times 10^2$) in 0.1 ml medium were seeded in a 96-well microtiter plate on day 0. On day one, 0.1 ml aliquots of medium containing graded concentrations of test compounds were added to the cell plates. After incubation at 37° C. in a humidified incubator for 72 hr, the plates containing L1210 cells were centrifuged briefly and 100 μl of the growth medium was removed. Cell cultures were incubated with 50 μl of MTT for 4 h at 37° C. (12). The resulting purple formazan precipitate was solubilized with 200 μl of 0.04N HCl in isopropyl alcohol. Absorbance was read in a Titertek Multiskan MCC scanning well spectrophotometer (Flow Laboratories) at a test wavelength of 570 nm and a reference wavelength of 630 nm. The absorbances were stored on a floppy disk on an IBM-XT and uploaded onto a VAX computer. $IC_{50}$ values were determined by a computer program that fit the data to the following equation:

$$Y = ((A_m - A_o)/(1 + (X/IC_{50})^n)) + A_o$$

where Am=absorbance of the control cells; $A_o$=absorbance of the cells in the presence of highest compound concentration; Y=observed absorbance; X=compound concentration; $IC_{50}$=dose of compound that inhibits the number of population doublings of cells to one half that of the number of population doublings of the control cells; and n equals the slope of the straight portion of the curve. The values reported in the table are from at least one experiment performed in eight replicates. If more than one experiment was performed, the number reported is the average of all the trials The results of these tests are shown in Table IX.

It Vivo Human Tumor Xenograft Models

The DLD-2 human colon tumor and MX-1 human mammary carcinoma, were originally obtained from a surgically-removed primary colon carcinoma or breast tumor respectively. The human tumor lines were maintained by serial passage in athymic nude mice. The MX-1 human mammary carcinoma is an established tumor Used by the NCI. The DLD-2 human colon tumor has been well characterized. (Dexter, D. L.; Spremulli, E. N.; Matook, G. M.; Diamond, I.; Calabresi, P. Cancer Research 1982, 42, 5010; Dexter, D. L.; Barbosa, J. A.; Calabresi, P. *Cancer Research* 1979, 39, 1020.)

The mice used in these experiments were outbred Swiss mice or CD-1 mice bearing the nude (nu/nu) gene. On Day 0, male and female mice weighing 22–30 g are inoculated with 0.2 mL of a 25% tumor mince. This mince is prepared by mincing fresh tumor tissue, grown subcutaneously in passage mice, in sterile physiological saline. Palpable tumors weighing approximately 50 mg appear in the mice within 7–10 days after inoculation. The mice are pair matched by tumor weight and sex into groups of ten each and the test compounds and vehicle control are administered intravenously (i.v.) once daily for nine consecutive days. A >20% decrease in body weight on Day 5 following compound administration is considered an indication of toxicity. Tumor measurements and body weights are recorded once a week. Fifteen to eighteen days after the initial injection the mice are weighed, sacrificed, and the tumors excised and weighed.

The efficacy of the test compounds is determined by the extent of tumor growth inhibition in treated versus vehicle-treated control mice. Initial tumor weights (mg) are calculated from the tumor dimensions (mm) obtained from caliper measurements, using the formula for a prolate ellipsoid (mg of tumor weight=(length-$\times$width$^2$)/2). Net tumor weights are calculated for each of the treated groups and the vehicle-treated control group by subtracting the initial tumor weight from the final tumor weight (Day 15–18). Results are expressed as a percentage decrease relative to the mean tumor weight for the control vehicle-treated group.

% Tumor Growth Inhibition =

$$\left(1 - \frac{\text{mean tumor weight of treated} \times 100}{\text{mean tumor weight of control}}\right)$$

The evaluation criteria of the National Cancer Institute for activity in in vivo cancer models were used. Tumor growth inhibition of 58–89% against the various xenografts is considered moderate activity, and inhibition of ≧90% is considered good to excellent activity. Actual tumor regressions (IR=incomplete regression; FR=full regression) indicate excellent to outstanding activity. Compounds demonstrating <58% growth inhibition are considered inactive.

The compounds of Examples 3, 5, 7, 8, 13, 17, 18, 111, 114, 115, and 118 were found to have moderate to excellent Tumor Growth Inhibition activity against DLD-2. The compounds of Examples 6, 8, 13, 19, 20, 25, 111, 112, 114, 115, 117 and 118 were found to have moderate to excellent Tumor Growth Inhibition activity against MX-1.

TABLE IX

| Ex | L1210 | Clone A | DLD-2 | MX-1 | Solubility |
|----|-------|---------|-------|------|------------|
| 1 | 0.134 | 0.060 | 16(25) | nt | 2.3 |
| 2 | 0.020 | 0.044 | 0(12.5) | nt | 0.01 |
| 3 | 0.006 | 0.004 | 92(20) | nt | 0.08 |
| 4 | 0.011 | 0.005 | 57(10) | nt | 0.45 |
| 5 | 0.006 | 0.013 | 82(10) | nt | 0.06 |
| 6 | 0.041 | 0.005 | nt | 81(12.5) | 0.33 |
| 7 | 0.048 | 0.028 | 83(12.5) | nt | 0.68 |
| 8 | 0.030 | 0.008 | 95(10) 2/9 IR | 7/9 IR 2/9 FR (5) | 4.0 |
| 9 | 0.182 | 0.166 | nt | nt | 11 |
| 10 | 0.588 | 0.346 | nt | nt | nd |
| 11 | 0.171 | 0.543 | nt | nt | nd |
| 12 | 0.027 | 0.009 | nt | nt | 0.05 |
| 13 | 0.065 | 0.030 | 90(12.5) 1/9 IR | 99(12.5) 7/9 IR | 7.1 |
| 14 | 0.008 | 0.003 | nt | nt | 0.9 |
| 15 | 0.002 | 0.002 | nt | nt | 0.81 |
| 16 | <0.01 | 0.002 | nt | nt | nd |
| 17 | 0.001 | 0.001 | 59(6.2) | nt | nd |
| 18 | 0.001 | 0.007 | 84(12.5) | nt | 0.02 |
| 19 | 0.013 | 0.009 | nt | 84(6) | 0.95 |
| 20 | 0.012 | nt | nt | 95(6.2) 1/9 IR | 3.33 |
| 21 | 0.042 | 0.005 | nt | nt | 7.70 |

TABLE IX-continued

| Ex | L1210 | Clone A | DLD-2 | MX-1 | Solubility |
|---|---|---|---|---|---|
| 22 | 0.020 | 0.003 | nt | 0(25) | 0.03 |
| 23 | 0.042 | 0.043 | nt | 0(25) | 0.12 |
| 24 | 0.130 | 0.022 | nt | nt | 0.15 |
| 25 | 0.048 | 0.010 | 97(25) | 99(25) 6/8 IR 1/8 FR | 4.82 |
| 26 | 0.018 | 0.012 | nt | 22(6.2) | nd |
| 40 | 0.098 | 0.412 | nt | nt | 0.06 |
| 41 | 0.317 | 0.804 | nt | nt | nd |
| 42 | 0.137 | 0.271 | nt | nt | 0.06 |
| 43 | 0.357 | 0.400 | nt | nt | 0.04 |
| 44 | 0.888 | 1.010 | nt | nt | 0.27 |
| 45 | 0.300 | 1.048 | nt | nt | nd |
| 46 | 0.414 | 0.958 | nt | nt | 0.04 |
| 47 | 0.378 | 0.763 | nt | nt | 0.15 |
| 48 | 0.773 | 1.462 | nt | nt | nd |
| 49 | 0.026 | 0.007 | nt | nt | nd |
| 50 | 0.126 | 0.032 | nt | nt | nd |
| 51 | 0.205 | 0.747 | nt | nt | nd |
| 52 | 0.082 | 0.044 | nt | nt | nd |
| 53 | 0.453 | 0.755 | nt | nt | nd |
| 54 | 0.198 | 0.615 | nt | nt | nd |
| 55 | 0.356 | 5.434 | nt | nt | nd |
| 56 | 0.365 | 0.222 | nt | nt | 0.04 |
| 80 | 0.389 | 0.635 | nt | nt | 0.42 |
| 81 | 0.201 | 22.22 | nt | nt | 7.6 |
| 82 | 0.082 | 0.068 | nt | nt | 4.5 |
| 83 | <0.01 | 0.004 | nt | nt | nd |
| 90 | 0.013 | 0.017 | nt | nt | nd |
| 100 | 0.014 | 0.070 | nt | 24(20) | 0.16 |
| 101 | 0.105 | 0.050 | nt | nt | nd |
| 110 | 0.183 | 0.006 | nt | nt | nd |
| 111 | 0.003 | 0.002 | 99(18) 2/7 IR | 99(20) 7/9 IR 1/9 FR | 0.24 |
| 112 | 0.020 | 0.007 | 48(12.5) | 98(25) 3/8 IR | 7.5 |
| 113 | 0.008 | 0.0003 | nt | nt | nd |
| 114 | <0.01 | 0.001 | 99(12.5) 4/8 IR | 98(12) 5/8 IR | 0.68 |
| 115 | 0.003 | 0.001 | 90(10) | 95(6) 1/8 IR | 0.15 |
| 116 | 0.012 | 0.003 | nt | nt | nd |
| 117 | 0.036 | 0.002 | nt | 8/8 IR(6) | 8.70 |
| 118 | 0.029 | 0.0008 | 99(6) 7/9 IR | 8/8 IR(3) | 65.1 |
| 119 | 0.044 | 0.003 | nt | nt | nd |
| 120 | 0.261 | 0.013 | nt | nt | nd |
| 121 | 0.397 | 0.032 | nt | nt | nd |
| 122 | 0.211 | 0.023 | nt | nt | nd |
| 123 | 0.013 | nt | nt | nt | 5.77 |
| 124 | 0.011 | nt | nt | nt | 0.29 |
| 140 | 0.425 | 0.101 | 0(50) | nt | 9 |

L1210 and Clone A are in vitro cell culture assays with the data expressed as an $IC_{50}$ in μg/mL.
DLD-2 and MX-1 are in vivo human tumor xenografts with the data expressed as percent tumor growth inhibition with the dose in mg/kg in parentheses. Any regressions are indicated.
Solubility is expressed as g/L in water.
nt: not tested.
nd: not determined.

Dosage Forms

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addtion, parenteral solutions can contain preservatives, such as benzalkonium chloride, methyl- or propyl-paraben, and chlorobutanol.

Suitable pharmaceutical carriers are described in Remington's Pharmaceutical Sciences, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstrach and 98.8 milligrams of lactose. Appropriate coatings may be applied to increase palatability or delay dissolution.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

We claim:

1. A compound of formula I:

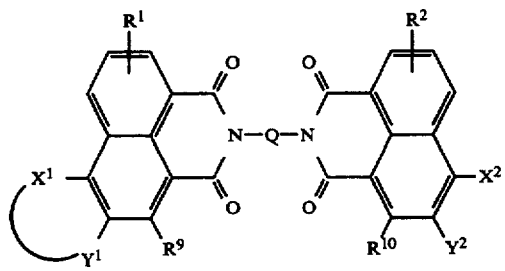

and pharmaceutically acceptable salts thereof,
and pharmaceutically acceptable salts thereof, wherein:

$R^1$, $R^2$, $R^3$, $R^9$ and $R^{10}$ are independently selected at each occurrence from the group:
   H, $C_1$-$C_4$ alkyl, $OR^4$, $N(R^4)_2$, $NO_2$, CN, F, Cl, Br, I, Ph, and $CF_3$, and $NHC(O)R^4$;

$R^4$ is independently selected at each occurrence from the group:
   H, $C_1$-$C_4$ alkyl, Ph, and $CH_2Ph$;

$X^1$ and $Y^1$ join together to form:
   a five membered heterocycle having 1 N or NH substituted with 1-2 $R^3$; a six membered heterocycle having 1 N and substituted with 1-2 $R^3$; or the group:

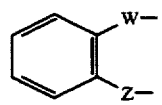

wherein one of W or Z is C=O and the other is C=O, NH, S or O;

$X^2$ and $Y^2$ are optionally present and when present may join together to form:
   a five membered heterocycle having 1 N or NH substituted with 1-2 $R^3$; a six membered heterocycle having 1 N and substituted with 1-2 $R^3$; or the group:

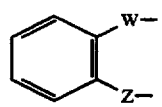

wherein one of W or Z is C=O and the other is C=O, NH, S or O; or when $X^2$ and $Y^2$ are not joined together and when $R^2$ is in the 4-position, then $X^2$ and $R^2$ may join together to form an ethylene bridge;

Q is:

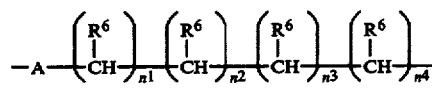

wherein A is $NR^8$ or

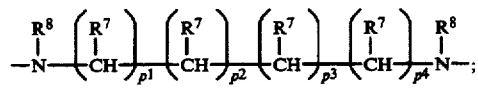

$R^5$, $R^6$, and $R^7$ are independently selected at each occurrence from the group:
   H, $C_1$-$C_3$ alkyl, allyl, or $CH_2G$, wherein G is OH, $OCH_3$, $CH_2SCH_3$, $(CH_2)_qNH_2$ and phenyl;

$R^8$ is independently selected at each occurrence from the group:
   H, $C_1$-$C_3$ alkyl and allyl;

$m^1$, $m^2$, $m^3$, and $m^4$ are independently 0-1, provided that at least two of $m^1$, $m^2$, $m^3$, and $m^4$ are 1;

$n^1$, $n^2$, $n^3$, and $n^4$ are independently 0-1, provided that at least two of $n^1$, $n^2$, $n^3$, and $n^4$ are 1;

$p^1$, $p^2$, $p^3$, and $p^4$ are independently 0-1, provided that at least two of $p^1$, $p^2$, $p^3$, and $p^4$ are 1; and q is independently at each occurrence 0-2.

2. A compound of claim 1 wherein:

$R^1$, $R^2$ and $R^3$ are independently selected at each occurrence from the group:
   H, $CH_3$, $NH_2$, $NO_2$, and CN;

$R^9$ and $R^{10}$ are H;

$X^1$ and $Y^1$ join together to form:
   a six membered heterocycle having 1 N and substituted with 1-2 $R^3$; or the group:

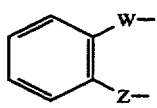

wherein one of W or Z is C=O and the other is C=O, NH, S or O;

$X^2$ and $Y^2$ are optionally present and when present may join together to form:
a six membered heterocycle 1 N and substituted with 1-2 $R^3$; or the group:

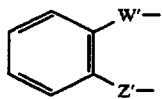

wherein one of W' or Z' is C=O and the other is C=O, NH, S or O; or when $X^2$ and $Y^2$ are not joined together and when $R^2$ is in the 4-position, then $X^2$ and $R^2$ may join together to form an ethylene bridge.

3. A compound of claim 2 wherein:
$R^1$ and $R^2$ are independently selected at each occurrence from the group:
H, $NH_2$ and $NO_2$;
$X^1$ and $Y^1$ join together to form:
a six membered heterocycle having 1 N and substituted with 1-2 $R^3$;
$X^2$ and $Y^2$ are optionally present and when present may join together to form:
a six membered heterocycle having 1 N and substituted with 1-2 $R^3$; or
when $X^2$ and $Y^2$ are not joined together and when $R^2$ is in the 4-position, then $X^2$ and $R^2$ may join together to form an ethylene bridge;
$R^5$ and $R^6$ are independently selected at each occurrence from the group:
H, $CH_3$, $CH_2CH_3$ and $CH_2CH_2SCH_3$;
$R^8$ is independently selected at each occurrence from the group:
H and $CH_3$; and
the sum of the values of $m^1$, $m^2$, $m^3$, $m^4$, $n^1$, $n^2$, $n^3$, and $n^4$ is 4–7.

4. A compound of claim 3 wherein:
$R^3$ is independently selected from the group:
H and $CH_3$;
$R^7$ is independently selected from the group:
H, $CH_3$, $CH_2CH_3$ and $CH_2CH_2SCH_3$; and
Q is selected from the group:

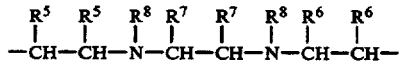

and

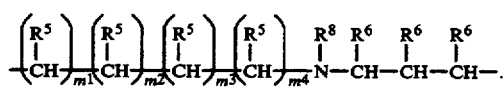

5. The compounds of claim 1 which are:
(R,R)-1,2-bis-[2-(3-Nitro-5-azaphenanthrene-1,10-dicarboximido)propylamino]ethane Dihydromethanesulfonate;

(S,S)-1,2-bis-[2-(3-Nitro-5-azaphenanthrene-1,10-dicarboximido)-1-methylethylamino]-ethane Dihydromethanesulfonate;

(S,S)-1,2-bis-[2-(3-Nitro-5-azaphenanthrene-1,10-dicarboximido)-1-methylethylamino]ethane Dihydromethanesulfonate;

(R,R)-1,2-bis-[2-(3-Nitro-7-methyl-5-azaphenanthrene-1,10-dicarboximido)propylamino]-(S)-1-methylethane Dihydromethanesulfonate;

4-[3-(3-Nitro-5-azaphenanthrene-1,10-dicarboximido)propylamino]-1-(3-nitronaphthalene-1,8-dicarboximido)butane Hydromethanesulfonate;

(R,R)-1-[2-(5-Azaphenanthrene-1,10-dicarboximido)-propylamino]-2-[2-(3-nitronaphthalene-1,8dicarboximido)propylamino]ethane Dihydromethanesulfonate;

4-[3-(8-Azaphenanthrene-1,10-dicarboximido)-propylamino]-1-(3-nitronaphthalene-1,8-dicarboximido)butane Hydromethanesulfonate;

(R,R)-1-[2-(3-Nitro-7-methyl-5-azaphenanthrene-1,10-dicarboximido)propylamino]-2-[2-(3-nitronaphthalene-1,8-dicarboximido) propylamino]ethane Dihydromethanesulfonate;

(R,R)-1-[2-(6-Azaphenanthrene-1,10-dicarboximido)-propylamino]-2-[2-(3-nitronaphthalene-1,8-dicarboximido)propylamino]ethane Dihydromethanesulfonate;

(R,R)-1-[3-Nitro-6-azaphenanthrene-1,10-dicarboximido)propylamino]-2-[2-(3-nitro naphthalene-1,8-dicarboximido)propylamino]ethane Dihydromethanesulfonate.

6. A pharmaceutical composition comprising a pharmaceutically acceptable carrier and a therapeutically effective amount of a compound of claim 1.

7. A pharmaceutical composition comprising a pharmaceutically acceptable carrier and a therapeutically effective amount of a compound of claim 2.

8. A pharmaceutical composition comprising a pharmaceutically acceptable carrier and a therapeutically effective amount of a compound of claim 3.

9. A pharmaceutical composition comprising a pharmaceutically acceptable carrier and a therapeutically effective amount of a compound of claim 4.

10. A pharmaceutical composition comprising a pharmaceutically acceptable carrier and a therapeutically effective amount of a compound of claim 5.

11. A method of treating a solid tumor carcinoma selected from the group: lung tumor, breast tumor and colon tumor in a mammal comprising administering to a mammal in need of such treatment, a tumor-inhibiting amount of a compound of claim 1.

12. A method of treating a solid tumor carcinoma selected from the group: lung tumor, breast tumor and colon tumor in a mammal comprising administering to a mammal in need of such treatment, a tumor-inhibiting amount of a compound of claim 2.

13. A method of treating a solid tumor carcinoma selected from the group: lung tumor, breast tumor and colon tumor in a mammal comprising administering to a mammal in need of such treatment, a tumor-inhibiting amount of a compound of claim 3.

14. A method of treating a solid tumor carcinoma selected from the group; lung tumor, breast tumor and colon tumor in a mammal comprising administering to a mammal in need of such treatment, a tumor-inhibiting amount of a compound of claim 4.

15. A method of treating a solid tumor carcinoma selected from the group: lung tumor, breast tumor and colon tumor in a mammal comprising administering to a mammal in need of such treatment, a tumor-inhibiting amount of a compound of claim 5.

* * * * *